(12) United States Patent
Fu et al.

(10) Patent No.: US 11,028,111 B2
(45) Date of Patent: Jun. 8, 2021

(54) COMPOUND FOR TREATING METABOLIC DISEASES AND PREPARATION METHOD AND USE THEREOF

(71) Applicant: Xi' An Biocare Pharma Ltd., Shaanxi (CN)

(72) Inventors: Guoqin Fu, Shaanxi (CN); Wei Ding, Shaanxi (CN); Bo Yin, Shaanxi (CN); Chao Yang, Shaanxi (CN); Cuiqin Wang, Shaanxi (CN); Yong Dou, Shaanxi (CN); Ruiling Wang, Shaanxi (CN)

(73) Assignee: XI' AN BIOCARE PHARMA LTD., Shaanxi (CN)

( * ) Notice: Subject to any disclaimer, the term of this patent is extended or adjusted under 35 U.S.C. 154(b) by 0 days.

(21) Appl. No.: 16/626,934

(22) PCT Filed: Aug. 15, 2018

(86) PCT No.: PCT/CN2018/100663
§ 371 (c)(1),
(2) Date: Dec. 27, 2019

(87) PCT Pub. No.: WO2019/119832
PCT Pub. Date: Jun. 27, 2019

(65) Prior Publication Data
US 2020/0131212 A1    Apr. 30, 2020

(30) Foreign Application Priority Data

Dec. 19, 2017 (CN) .......................... 201711371702.0

(51) Int. Cl.
*C07F 9/6574* (2006.01)
*A61P 1/16* (2006.01)
*A61P 9/12* (2006.01)
*C07F 9/22* (2006.01)

(52) U.S. Cl.
CPC ............ *C07F 9/65742* (2013.01); *A61P 1/16* (2018.01); *A61P 9/12* (2018.01); *C07F 9/222* (2013.01)

(58) Field of Classification Search
CPC .................................................. C07F 9/65742
USPC ....................................................... 546/282.4
See application file for complete search history.

(56) References Cited

U.S. PATENT DOCUMENTS

| 5,541,348 A | 7/1996 | Ayra et al. |
| 2016/0145296 A1 | 5/2016 | Or et al. |
| 2016/0159851 A1 | 6/2016 | Gonzalez et al. |

FOREIGN PATENT DOCUMENTS

| CN | 101747404 A | 6/2010 |
| CN | 104672290 A | 6/2015 |
| CN | 105593237 A | 5/2016 |
| CN | 107231795 A | 10/2017 |
| WO | 2016173524 A1 | 11/2016 |
| WO | 2017062763 A1 | 4/2017 |
| WO | 2017147137 A1 | 8/2017 |

OTHER PUBLICATIONS

International Search Report and Written Opinion issued in International Application No. PCT/CN2018/100663, dated Nov. 15, 2018, 19 pages.
Reddy, K.R., et al., "Stereoselective synthesis of nucleoside monophosphate HepDirect prodrugs," 2005, pp. 4321-4324, Tetrahedron Letters 46, ScienceDirect.
Yu, Z., et al., "Pharmacokinetics in Vitro and in Vivo of two novel prodrugs of oleanolic acid in rats and its hepatoprotective effects against liver injury induced by $CCl_4$," Mar. 28, 2016, pp. 1699-1710, vol. 13, Molecular Pharmaceutics.
Zhang, L., et al., "The progress of bile acids and metabolic syndrome," Mar. 2016, pp. 964-967, vol. 22(5), Medical Recapitulate (abstract only).
Chinese First Office Action issued in Chinese Patent Application No. 201810930184.X, dated Dec. 24, 2019, 27 pages.

*Primary Examiner* — Taofiq A Solola
(74) *Attorney, Agent, or Firm* — RatnerPrestia

(57) ABSTRACT

Provided are a compound for treating metabolic diseases having the structure as shown in formula (I) or formula (II), or a racemate, stereoisomer, geometric isomer, tautomer, solvate, hydrate, metabolite, pharmaceutically acceptable salt or prodrug thereof. The compound is an activator of FXR and/or a TGR5 receptor, and thus has the activity of activating FXR and/or a TGR5 receptor, and can be used in the preparation of drugs for treating chronic liver diseases, metabolic diseases or portal hypertension.

16 Claims, 7 Drawing Sheets

COMPOUND FOR TREATING METABOLIC DISEASES AND PREPARATION METHOD AND USE THEREOF

This application is the U.S. National Phase Application of PCT/CN2018/100663, filed Aug. 15, 2018, which claims the priority to Chinese Patent Application No. 201711371702.0, filed with China National Intellectual Property Administration on Dec. 19, 2017, and titled with "COMPOUND FOR TREATING METABOLIC DISEASES AND PREPARATION METHOD AND USE THEREOF", and the disclosures of which are hereby incorporated by reference.

FIELD

The present invention relates to the field of medicinal chemistry, in particular to a compound for treating metabolic diseases and preparation method and use thereof.

BACKGROUND

Bile acids have a variety of physiological functions. It not only plays an important role in absorption, transport and distribution of fat and fat-soluble vitamins, but also acts as a signaling molecule to activate nuclear receptors and then regulates the metabolism of bile acids and cholesterol. The enterohepatic circulation of bile acids is an important regulatory mechanism regulating the rate of bile acid synthesis. Bile acid is synthesized in the liver and enters the gallbladder, and then secreted into the small intestine, reabsorbed in the ileum and transported back to the liver via the portal circulation.

Cholestasis mainly occurs in patients in advanced pregnancy, with liver fibrosis, cirrhosis and biliary obstruction. The clinical manifestations include itching, choleplania, and elevated serum alkaline phosphatase (ALP). For drugs for cholestasis, clinically, the most commonly used one currently is ursodeoxycholic acid (UDCA). It is a steroidal compound, an analog of cholic acid, having a function of bile-draining, and is used to treat cholesterol gallstones and prevent the formation of drug-induced stones. However, UDCA has a poor agonistic effect on the bile acid nuclear receptor FXR, thus has limitations in the treatment of cholestasis, and some patients with cholestasis are not sensitive to UDCA.

Research showed that FXR receptor (farnesylxreceptor) is a member of the hormone nuclear receptor superfamily. It has a typical nuclear receptor structure, i.e. including a highly conserved DNA binding domain at the amino acid terminus, a carboxyl terminal ligand binding domain, a ligand-independent transcriptional activation domain at the amino terminus, and a ligand-dependent activation domain at the carboxyl terminus, etc. FXR is highly expressed in the enterohepatic system, kidney, and adrenal glands; besides, it has low expression levels in the heart, lung, fat, and stomach. The expression of many FXR target genes associated with bile acid anabolism in the liver, small intestine, and kidney has been confirmed. FXR is a bile acid sensor. Several research groups reported that bile acids are FXR endogenous ligands under physiological conditions. It was found that bile acids not only can bind directly to FXR, but also the interaction of the two can lead to the recruitment of coactivators and corepressors, which demonstrate that the bile acids are FXR endogenous ligands, and therefore FXR is also known as the bile acid receptor. As a receptor for bile acids, FXR can maintain the homeostasis of bile acids by regulating the expression of genes involved in bile acid metabolism. FXR is a key regulator of cholesterol homeostasis, triglyceride synthesis, and lipogenesis (Crawley, Expert Opinion Ther. Patents (2010), 20(8): 1047-1057). FXR-related diseases include side effects induced by drugs, treatment of liver disease, diabetes and vitamin D-related diseases, and hepatitis.

The TGR5 receptor (G protein-coupled bile acid receptor 5) is a class of G-protein coupled receptors that have been identified as a cell surface receptor that responds to bile acids. TGR5 differs from bile acid nuclear receptors in expression and function, and the TGR5 gene is ubiquitously expressed in humans and animals. It has 993 base pairs, encodes a protein comprising 330 amino acids containing seven G-protein coupled receptor domains. It is highly conserved in humans and animals. In humans, this gene is located on chromosome 2q35 and expressed in multiple tissues with the highest levels in the spleen and placenta, and abundant expression in the lung, liver, small intestine and bone marrow. In the rat liver, TGR5 receptor is expressed in the serosal membrane of hepatic sinusoidal endothelial cells, the apical membrane of bile duct and primary cilia, bile duct epithelial cells, and Kupffer cells.

TGR5 receptor agonists are closely related to bile acid metabolism, sugar and energy metabolism, inflammation, immunity and tumors, and therefore have great potential for the treatment of related diseases.

SUMMARY

In view of the above, the technical problem to be solved by the present disclosure is to provide a compound for the treatment of metabolic diseases, a preparation method and use thereof targeting FXR and/or TGR5 receptors.

The present disclosure provides a compound having a structure as shown in Formula (I), or a racemate, a stereoisomer, a geometric isomer, a tautomer, a solvate, a hydrate, a metabolite, a pharmaceutically acceptable salt or a prodrug thereof:

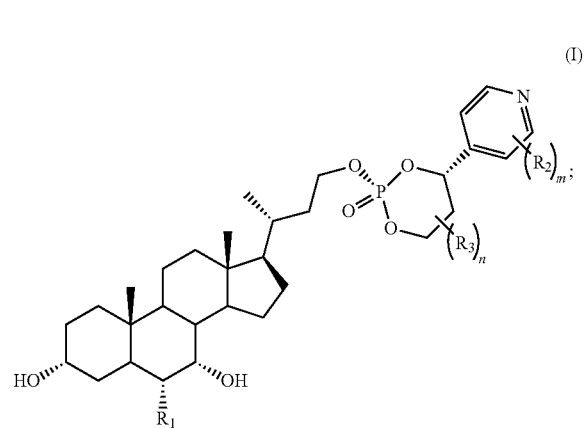

wherein $R_1$ is hydrogen, substituted or unsubstituted alkyl, or halogen. In some embodiments, $R_1$ is hydrogen, substituted or unsubstituted $C_{1-5}$ alkyl, or halogen; in other embodiments, $R_1$ is hydrogen, fluorine, chlorine, bromine, substituted or unsubstituted methyl, substituted or unsubstituted ethyl, substituted or unsubstituted propyl, or substituted or unsubstituted isopropyl. In certain specific examples of the present disclosure, $R_1$ is methyl, ethyl, propyl or isopropyl. In the embodiments of the present disclosure, when $R_1$ is a substituted alkyl, the alkyl may be a linear alkyl or a branched alkyl, the substituent of $R_1$ is D, F, Cl, Br, $C_{1-3}$ alkyl, cyano, hydroxy, nitro, amino or $C_{1-3}$ alkoxy.

Each of the $R_2$ is independently selected from the group consisting of a substituted or unsubstituted alkyl, halogen, hydroxyl, nitro, sulphonic acid group and carboxyl. In some embodiments, each of the $R_2$ is independently selected from the group consisting of $C_{1-5}$ alkyl, fluorine, chlorine, bromine, hydroxyl, nitro and carboxyl. In some embodiments, each of the $R_2$ is independently selected from the group consisting of fluorine, chlorine, bromine, nitro, cyano, substituted or unsubstituted methyl, substituted or unsubstituted ethyl, and substituted or unsubstituted isopropyl. In certain specific examples of the present disclosure, each of the $R_2$ is independently selected from the group consisting of fluorine, chlorine, nitro, substituted or unsubstituted methyl, and substituted or unsubstituted ethyl. In the embodiments of the present disclosure, when $R_2$ is a substituted alkyl, the alkyl may be a linear alkyl or a branched alkyl, the substituent of $R_2$ is D, F, Cl, Br, $C_{1-3}$ alkyl, cyano, hydroxyl, nitro, amino or $C_{1-3}$ alkoxy.

M is an integer from 0 to 4, i.e., m is 0, 1, 2, 3 or 4. In certain specific examples of the present disclosure, m is 0 or 1.

Each of the $R_3$ is independently selected from the group consisting of substituted or unsubstituted alkyl, halogen, hydroxyl and aryl; in some embodiments, each of the $R_3$ is independently selected from the group consisting of fluorine, chlorine, bromine, $C_{1-5}$ alkyl and $C_{6-10}$ aryl; in some embodiments, each of the $R_3$ is independently selected from the group consisting of fluorine, chlorine, bromine, substituted or unsubstituted methyl, and substituted or unsubstituted ethyl; in certain specific examples of the present disclosure, each of the $R_3$ is independently selected from the group consisting of fluorine, chlorine, bromine, methyl, ethyl, propyl, and isopropyl. In the embodiments of the present disclosure, when $R_3$ is a substituted alkyl, the alkyl may be a linear alkyl or a branched alkyl, the substituent of $R_3$ is D, F, Cl, Br, a $C_{1-3}$ alkyl, cyano, hydroxyl, nitro, amino or $C_{1-3}$ alkoxy.

n is an integer from 0 to 4, i.e., n is 0, 1, 2, 3 or 4. In certain specific examples of the present disclosure, n is 0 or 1.

In certain specific examples of the present disclosure, the structures of Formula (I) are specifically as follows:

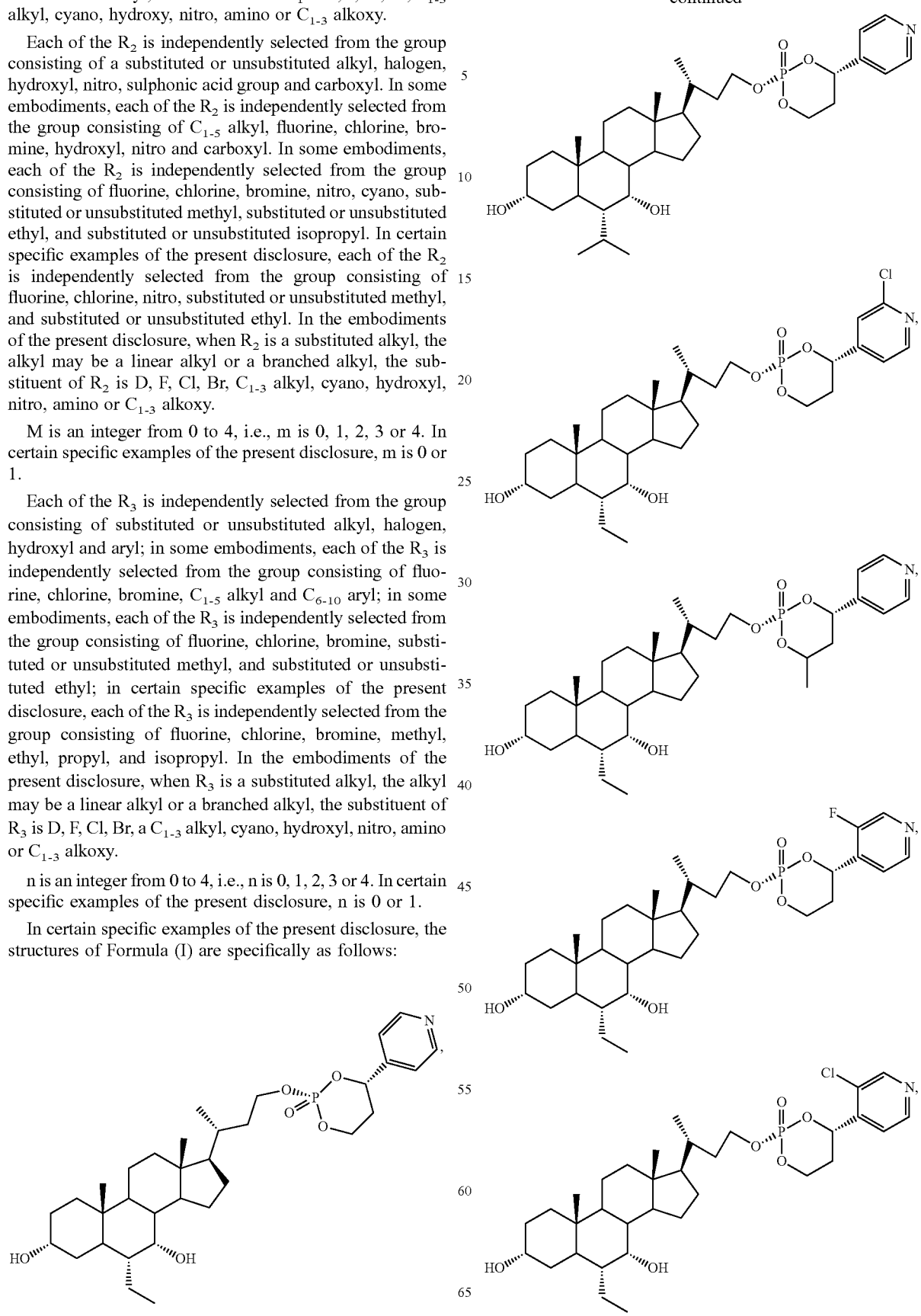

-continued

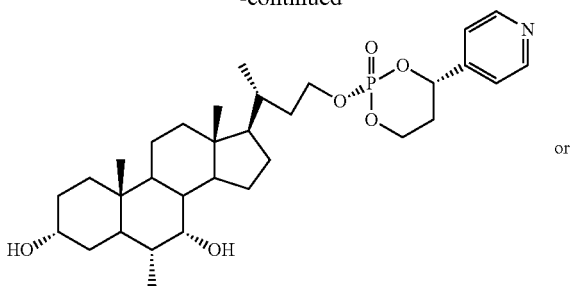

The present disclosure provides a compound for treating metabolic diseases, having a structure as shown in Formula (II), or a racemate, a stereoisomer, a geometric isomer, a tautomer, a solvate, a hydrate, a metabolite, a pharmaceutically acceptable salt or a prodrug thereof:

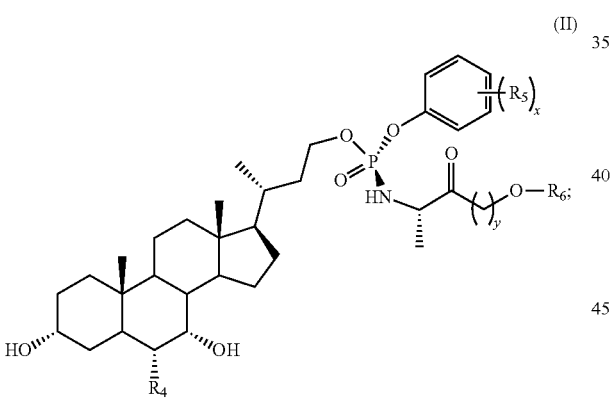

(II)

wherein $R_4$ is hydrogen, substituted or unsubstituted alkyl, or halogen; in some embodiments, $R_4$ is hydrogen, substituted or unsubstituted $C_{1-6}$ alkyl, or halogen; in other embodiments, $R_4$ is hydrogen, fluorine, chlorine, bromine, substituted or unsubstituted methyl, substituted or unsubstituted ethyl, substituted or unsubstituted propyl, or substituted or unsubstituted isopropyl. In certain specific examples of the present disclosure, $R_4$ is methyl, ethyl, propyl or isopropyl. In the embodiments of the present disclosure, when $R_4$ is a substituted alkyl, the alkyl may be a linear alkyl or a branched alkyl, the substituent of $R_4$ is D, F, Cl, Br, $C_{1-3}$ alkyl, cyano, hydroxy, nitro, amino or $C_{1-3}$ alkoxy.

Each of the $R_5$ is independently selected from the group consisting of substituted or unsubstituted alkyl, halogen, hydroxyl, cyano, nitro, sulfonyl hydroxide, and carboxyl; in some embodiments, each of the $R_5$ is independently selected from the group consisting of $C_{1-5}$ alkyl, fluorine, chlorine, bromine, hydroxyl, cyano, nitro and carboxyl. In some embodiments, each of the $R_5$ is independently selected from the group consisting of fluorine, chlorine, bromine, nitro, cyano, substituted or unsubstituted methyl, substituted or unsubstituted ethyl, and substituted or unsubstituted isopropyl. In certain specific examples of the present disclosure, each of the $R_5$ is independently selected from the group consisting of fluorine, chlorine, nitro, substituted or unsubstituted methyl, and substituted or unsubstituted ethyl. In the embodiments of the present disclosure, when $R_5$ is a substituted alkyl, the alkyl may be a linear alkyl or a branched alkyl, the substituent of $R_5$ is D, F, Cl, Br, $C_{1-3}$ alkyl, cyano, hydroxyl, nitro, amino or $C_{1-3}$ alkoxy.

$R_6$ is substituted or unsubstituted $C_{1-5}$ alkyl, aryl, heteroaryl, or cyclohexyl; in some embodiments, $R_6$ is substituted or unsubstituted methyl, substituted or unsubstituted ethyl, substituted or unsubstituted propyl, substituted or unsubstituted isopropyl, phenyl, pyridyl or cyclohexyl. In the embodiments of the present disclosure, when $R_6$ is a substituted alkyl, the alkyl may be a linear alkyl or a branched alkyl, the substituent of $R_6$ is D, F, Cl, Br, $C_{1-3}$ alkyl, cyano, hydroxy, nitro, amino or $C_{1-3}$ alkoxy.

X is an integer from 0 to 4, i.e., x is 0, 1, 2, 3 or 4. In certain specific examples of the present disclosure, x is 0 or 1.

Y is 0 or 1.

In certain specific examples of the present disclosure, the structures of Formula (II) are specifically as follows:

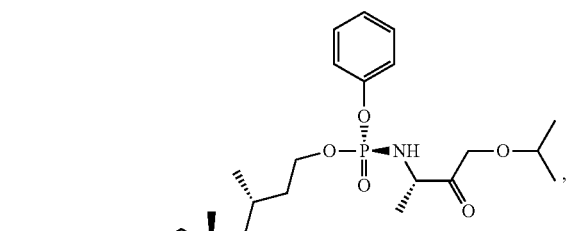

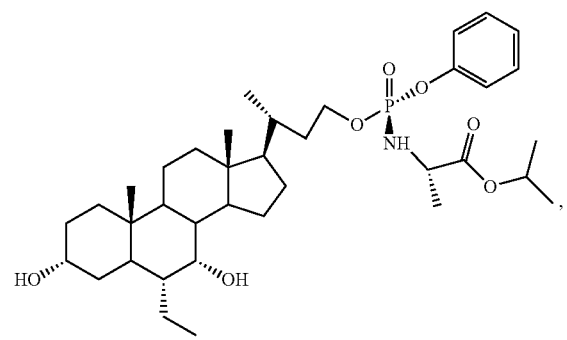

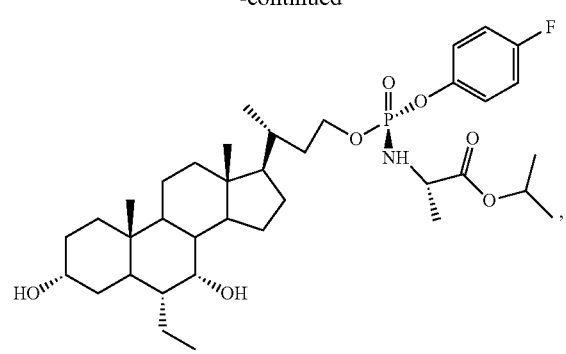
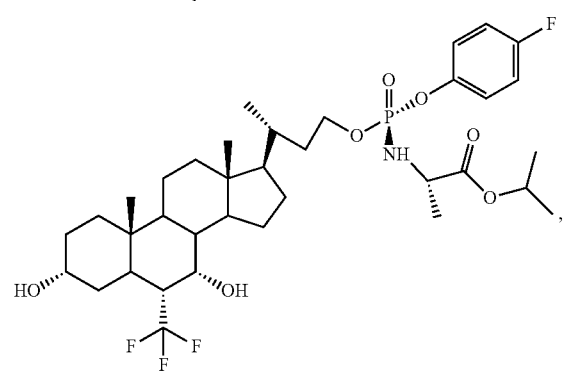
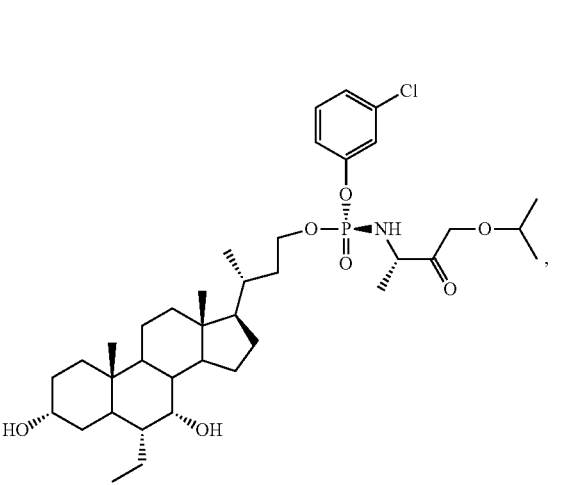
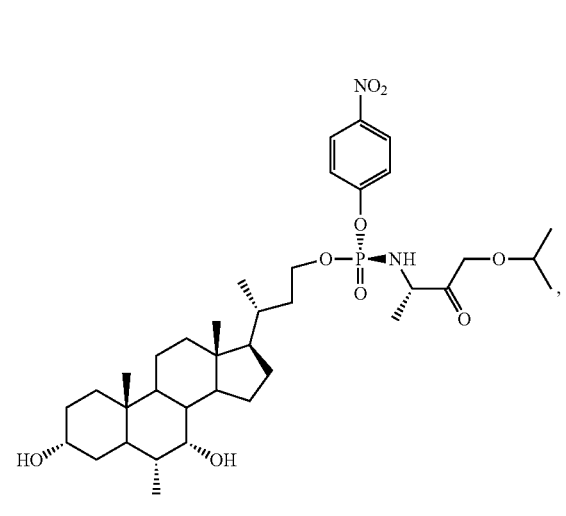
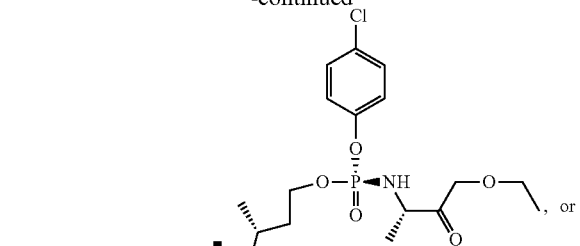
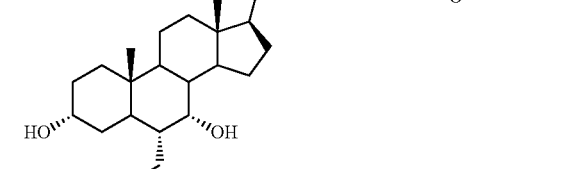
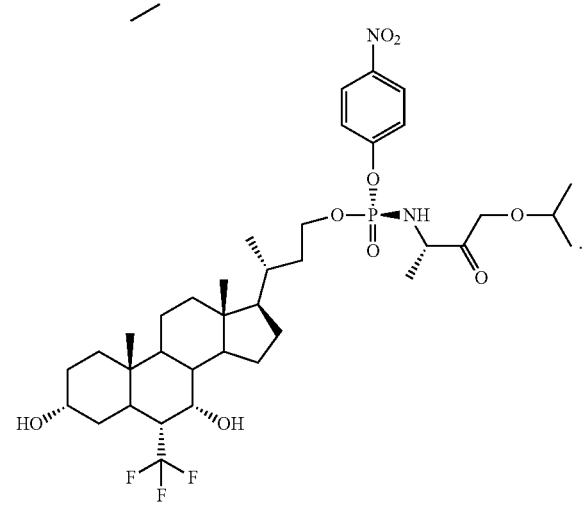
The present disclosure also provides a method of producing the compounds as shown in Formula (I), comprising the following steps:
reacting Compound (10) with Compound (16) to obtain a compound as shown in Formula (I);
(10)
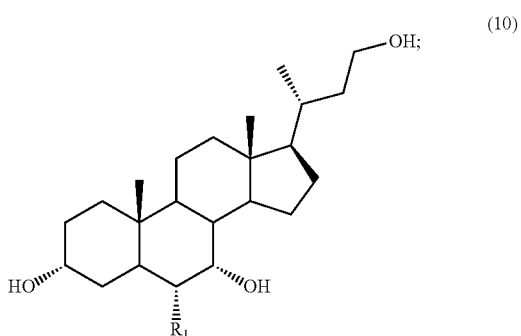
(16)
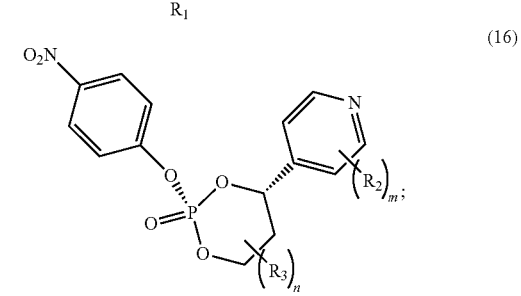

-continued

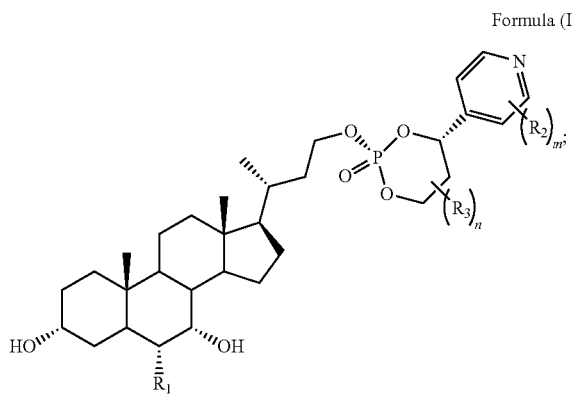

Formula (I)

wherein R$_1$, R$_2$, R$_3$, m, and n are defined as above, which are not described herein again.

In certain specific examples of the present disclosure, the reaction is carried out under the catalysis of tert-butylmagnesium chloride, the solvent of the reaction is 1,4-dioxane.

In certain specific examples of the present disclosure, the temperature of the reaction is 60 to 80° C., and the duration of the reaction is 1 to 3 hours.

In certain specific examples of the present disclosure, the synthetic route of Compound (10) is as follow:

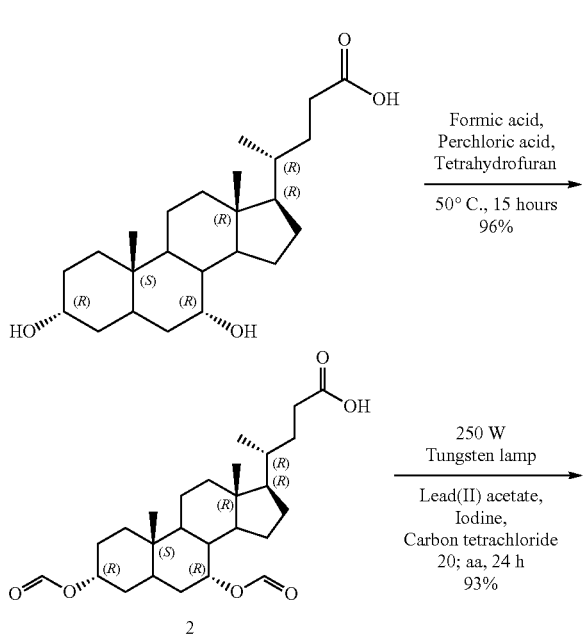

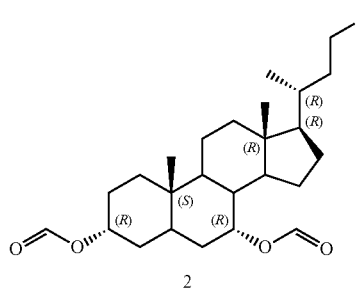

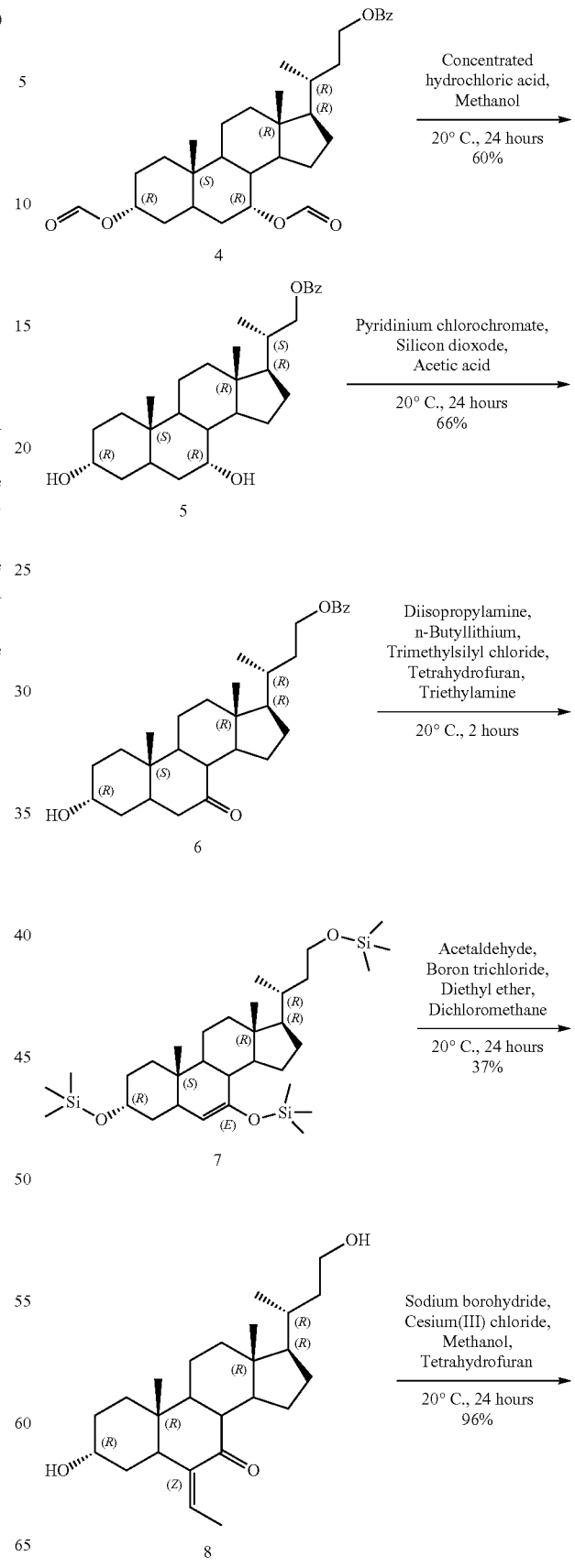

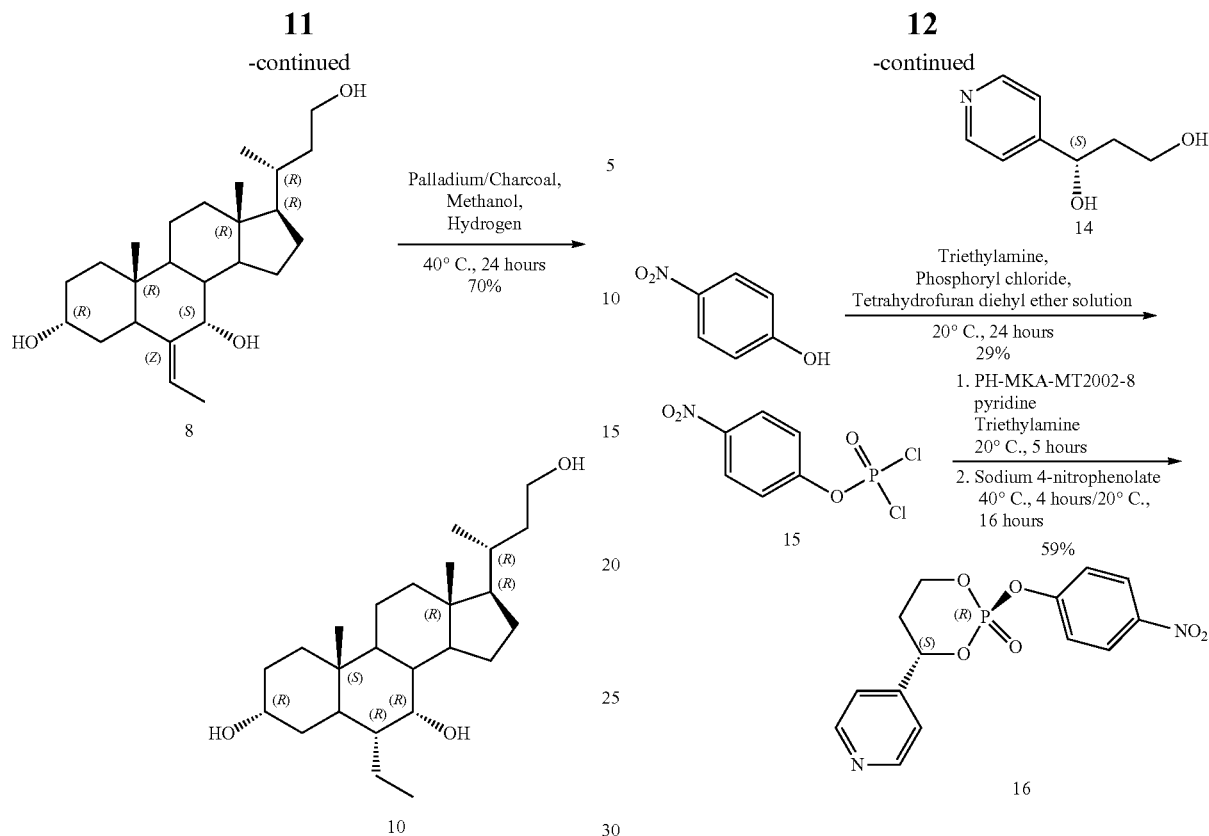

In certain specific examples of the present disclosure, the synthetic route of Compound (16) is as follows:

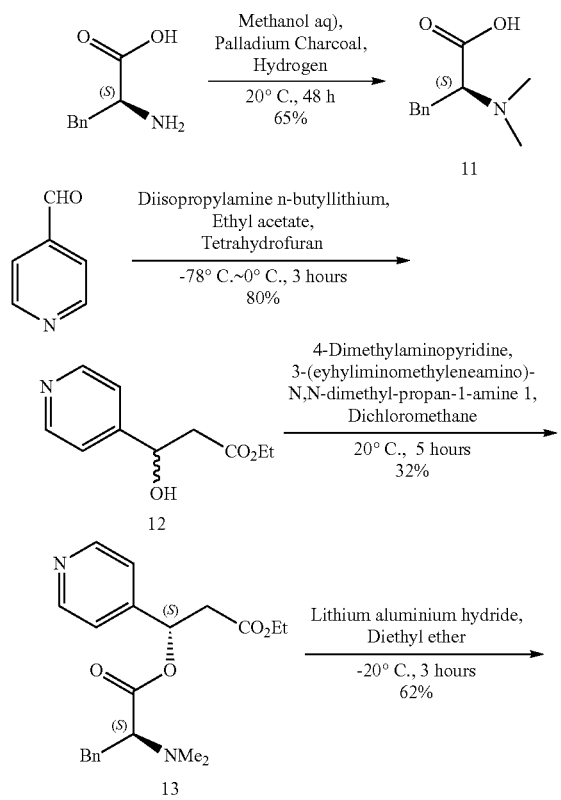

The present disclosure provides a pharmaceutical composition, comprising the above-mentioned compound for treating metabolic diseases or a compound produced by the above-mentioned preparation method, and a pharmaceutically acceptable carrier, excipient, diluent, adjuvant, vehicle or a combination thereof.

The pharmaceutical composition of the present disclosure may be administered orally, by injection, by spray inhalation, topically, rectally, nasally, sublingually, or by an implantable kit.

The dosage form of the pharmaceutical composition of the present disclosure may be an oral dosage form, such as a capsule, a tablet, a pill, a powder, a granule, an aqueous suspension or a solution.

The oral dosage form provided by the present disclosure may be provided as a compressed tablet, a grinded tablet, a chewable lozenge, a fast dissolving tablet, a re-compressed tablet, or an enteric-coated tablet, a sugar-coated tablet or a film-coated tablet. The enteric-coated tablet is a compressed tablet coated with a substance which is resistant to gastric acid but dissolves or disintegrates in the intestine, thereby preventing the active ingredient from contacting the acidic environment of the stomach. The enteric coatings include, but are not limited to, fatty acids, fats, phenyl salicylate, waxes, shellac, ammoniated shellac, and cellulose acetate phthalate. The sugar-coated tablet is a compressed tablet surrounded by a sugar coating which can be used to mask an unpleasant taste or odor and to prevent oxidation of the tablet. The film-coated table is a compressed tablet covered with a thin film or layer of a water-soluble substance. The film coatings include, but are not limited to, hydroxyethyl cellulose, carboxymethylcellulose sodium, polyethylene glycol 400, and cellulose acetate phthalate. The film coating has the same general characteristics as the sugar coating. The compressed tablet is a compressed tablet prepared over more than one compression cycle, including a multilayer tablet, and a press-coated or dry-coated tablet. The tablet dosage form can be prepared from an active ingredient in powder, crystalline or granular form, alone or in combination with one or more carriers or excipients described by the present disclosure. The carrier and excipients include adhesives, disintegrants, controlled-release polymers, lubricants, diluents, and/or colorants. The pharmaceutical composition provided by the present disclosure may be provided in a soft capsule or a hard capsule, which may be prepared from gelatin, methyl cellulose, starch, or calcium alginate. Liquid dosage forms for oral administration include, but are not limited to, pharmaceutically acceptable emulsions, microemulsions, solutions, suspensions, syrups and elixirs. In addition to the active compound, the liquid dosage form may comprise a conventional inert diluent such as water or other solvents, solubilizers and emulsifiers, such as ethanol, isopropanol, ethyl carbonate, ethyl acetate, benzyl alcohol, benzyl benzoate, propylene glycol, 1,3-butanediol, dimethylformamide, fats (especially cottonseed, groundnut, corn, microbe, olive, ramie and sesame oil), glycerin, tetrahydro-2-furanmethanol, polyethylene glycol, sorbitan fatty acid ester, and mixtures thereof. In addition to inert diluents, the oral compositions may also contain adjuvants such as wetting agents, emulsifiers or suspending agents, sweetening, flavoring and aromatic agents.

The pharmaceutical compositions of the disclosure may be in a form of suppository, or be administered rectally in a suitable enemas, or in a form of injection.

Adjuvants in the above-mentioned dosage forms can be selected according to the common knowledge of a person having ordinary skill in the art.

The above-mentioned compounds, the compounds prepared by the above-mentioned method, or the above-mentioned pharmaceutical compositions of the present disclosure are used, but not limited to, in the manufacture of a medicament for treatment or amelioration of FXR and/or TGR5 mediated diseases.

In certain specific examples of the present disclosure, the FXR and/or TGR5 mediated disease is selected from, but not limited to, a chronic liver disease, a metabolic disease, portal hypertension, and the like.

In certain specific examples of the present disclosure, the chronic liver disease is selected from the group consisting of primary biliary cholestatic cirrhosis, primary sclerosing cholangitis, a liver fibrosis-related disease, drug-induced cholestasis, progressive familial intrahepatic cholestasis, cholestasis of pregnancy, an alcoholic liver disease and a non-alcoholic fatty liver disease; the portal hypertension is a portal hypertension with increased portal pressure caused by liver fibrosis, cirrhosis, splenomegaly or another reason; the metabolic disease includes hypercholesterolemia, dyslipidemia, cholesterol gallstones, and hypertriglyceridemia.

The compound or composition of the present disclosure may also be used in combination with other drugs or compounds for treatment or amelioration of diseases such as chronic liver diseases, metabolic diseases or portal hypertension. The compound of the present disclosure may be administered as a separate active agent or in combination with other therapeutic agents, including other compounds which have the same or similar therapeutic activity and are determined to be safe and effective for such combination administration. In one aspect, the present disclosure provides a method of treating, preventing or improving a disease or condition, comprising administering a safe and effective amount of a combination drug which contains a compound disclosed by the present disclosure and one or more therapeutically active agents. In some embodiments, the combination drug comprises one or two other therapeutic agents.

In another aspect, the present disclosure provides a method for activating a FXR and/or TGR5 receptor, comprising administering to a subject or sample in need thereof a therapeutically effective amount of the compound disclosed by the present disclosure, the compound produced by the preparation method of the present disclosure, or the pharmaceutical composition disclosed by the present disclosure. The "therapeutically effective amount" or "effective amount" of the compound of the present disclosure may range from 2.5 mg/kg to 100 mg/kg. In some embodiments, the "therapeutically effective amount" or "effective amount" of the compound of the present disclosure may range from 0.4 mg/kg to 4 mg/kg; in other embodiments, the "therapeutically effective amount" or "effective amount" of the compound of the present disclosure may range from 0.2 mg/kg to 25 mg/kg.

In another aspect, the present disclosure provides a method for preventing, treating or ameliorating a FXR and/or TGR5 receptor mediated disease, comprising administering to a subject in need thereof a therapeutically effective amount of the compound disclosed by the present disclosure, the compound produced by the preparation method of the present disclosure, or the pharmaceutical composition disclosed by the present disclosure.

In certain specific examples of the present disclosure, the FXR and/or TGR5 receptor mediated disease is, but not limited to a chronic liver disease, a metabolic disease, or portal hypertension.

In certain specific examples of the present disclosure, the chronic liver disease is one or more of primary biliary cholestatic cirrhosis, primary sclerosing cholangitis, a liver fibrosis-related disease, drug-induced cholestasis, progressive familial intrahepatic cholestasis, cholestasis of pregnancy, an alcoholic liver disease, and a non-alcoholic fatty liver disease; the portal hypertension is selected from the group consisting of liver fibrosis, cirrhosis, and splenomegaly or increased portal pressure caused by other reasons; the metabolic diseases include hypercholesterolemia, dyslipidemia, cholesterol gallstones, and hypertriglyceridemia.

The term "therapeutically effective amount" or "therapeutically effective dose" as used in the present disclosure refers to an amount of a compound or composition of the present disclosure that is capable of eliciting a biological or medical response in an individual (such as reducing or inhibiting enzyme or protein activity, or activating receptors, or antagonizing receptors, or improving symptoms, alleviating symptoms, slowing or delaying disease progression, or preventing disease, etc.).

The compound disclosed by the present disclosure may contain asymmetric or chiral centers and therefore may exist in different stereoisomeric forms. The present disclosure includes all stereoisomeric forms of the compound as shown in Formulas (I) or (II), not limited to diastereomers, enantiomers, atropisomers, and geometric (or conformational) isomers, as well as mixtures thereof, such as racemic mixtures, as an integral part of the present disclosure.

In the structures disclosed by the present disclosure, when the any stereochemistry of a particular chiral atom is not indicated, all stereoisomers of the structure are considered within the present invention, and are included in the present invention as compounds disclosed herein. When stereochemistry is indicated by a solid wedge or dashed line for a particular configuration, the stereoisomer of the structure is clear and defined herein.

The compound of Formula (I) or (II) may exist in different tautomeric forms, and all such tautomers, such as the tautomers described by the present disclosure, are included within the scope of the present invention.

The compound of Formula (I) or (II) may exist in the form of a salt. In some embodiments, the salt refers to a pharmaceutically acceptable salt. In other embodiments, the salt may also be an intermediate used to prepare and/or purify the compound as shown in Formula (I) or (II) and/or to separate enantiomers of the compound of Formula (I) or (II).

Unless otherwise stated, all technical and scientific terms used in the present disclosure have the same meaning as commonly interpreted by a person having ordinary skill in the art. All patents and publications involved in the present disclosure are hereby entirely incorporated by reference. The terms "comprising", "including" are open-ended expressions, that is, includes the content indicated in the present disclosure but does not exclude other contents.

"Stereoisomer" refers to a compound that has the same chemical structure but differs in the way the atoms or groups are spatially aligned. Stereoisomers include enantiomers, diastereomers, conformational isomers (rotomers), geometric isomers (cis/trans) isomers, atropisomers, etc.

"Chirality" is a molecule that has properties that cannot overlap with its mirror image; while "achirality" refers to a molecule that can overlap with its mirror image.

"Enantiomer" refers to two isomers of a compound that are not superimposable but are mutually mirrored.

"Diastereomer" refers to a stereoisomer that has two or more chirality centers and whose molecules are not mutually mirrored. Diastereomers have different physical properties such as melting point, boiling point, spectral properties and activity. The mixture of diastereomers can be separated by high resolution analytical procedures such as electrophoresis and chromatography, such as HPLC.

The stereochemical definitions and rules used in the present disclosure generally follow SP Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of plane polarized light. When describing optically active compounds, the prefixes D and L or R and S are used to indicate the absolute configuration of the molecule with respect to one or more of its chiral centers. The prefixes d and l or (+) and (−) are symbols used to specify the rotation of the plane polarized light, wherein (−) or I indicates that the compound is levorotatory, and compound prefixed with (+) or d is dextrorotatory. A specific stereoisomer is an enantiomer, and a mixture of such isomers is referred to as a mixture of enantiomers. A 50:50 mixture of enantiomers is referred to as a racemic mixture or a racemate, which may occur when there is no stereoselectivity or stereospecificity in a chemical reaction or process.

Any asymmetric atom (e.g., carbon, etc.) of the compounds disclosed by the present disclosure may exist and be enriched in racemic or enantiomerical form, such as exist in the (R)-, (S)- or (R,S)-configuration. In certain embodiments, each asymmetric atom has at least 50% enantiomer, at least 60% enantiomer, at least 70% enantiomer, at least 80% enantiomer, at least 90% enantiomer, at least 95% enantiomer, or at least 99% enantiomer in the (R)- or (S)-configuration.

The term "unsubstituted" represents that the specified group does not have a substituent. The term "substituted" represents that one or more hydrogen atoms which may be substituted in a given structure are substituted by a specific substituent. Unless otherwise showed, a substituted group may have one substituent at each substitutable position of the group. When more than one position in the given formula can be substituted by one or more substituents selected from a specific group, substitution may happen at various positions, either identically or differently. The substituents of the present disclosure include, but not limited to, D, —OH, —NH$_2$, F, Cl, Br, a C$_{1-3}$ alkyl, cyano, hydroxy, nitro, or C$_{1-3}$ alkoxy.

The descriptions used in the present disclosure "each . . . independently" and " . . . each independently" and " . . . independently" are interchangeable and should be interpreted broadly. It may refers to that the specific substituents represented by the same symbols in different groups do not affect each other, or that the specific substituents represented by the same symbols in the same group do not affect each other.

The term "halogen" refers to fluorine (F), chlorine (Cl), bromine (Br) or iodine (I).

The term "alkoxy" represents that alkyl attached to the remainder of the molecule through an oxygen atom, wherein the alkyl has the meaning as described by the present disclosure. Unless otherwise specifically stated, the alkoxy contains 1 to 12 carbon atoms. In some embodiments, the alkoxy contains 1 to 6 carbon atoms; in other embodiments, the alkoxy contains 1 to 4 carbon atoms; in still other embodiments, the alkoxy contains 1 to 3 carbon atoms. The alkoxy may be alternatively substituted with one or more substituents described by the present disclosure.

As described by the present disclosure, a bond from a substituent to a central ring forming a ring system (as shown in Formula a) represents the alternative substitution of a substituent at all substitutable positions on the ring system. Formula a represents that all positions on the pyridine ring may be alternatively substituted by the substituent R, for example, as shown in Formula b to Formula d.

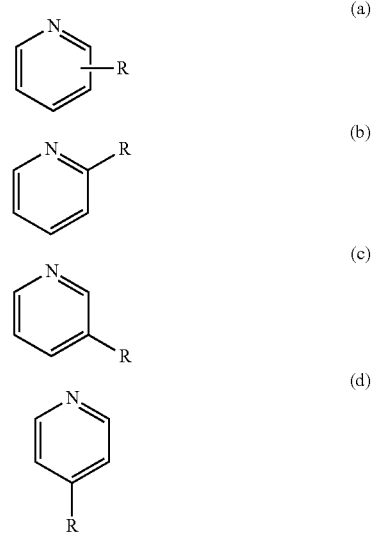

As described by the present disclosure, a substituent with a lower subscript and attached to a central ring forms a ring system (as shown in Formula e), which represents that all substitutable positions on the ring system may be substituted with the substituent.

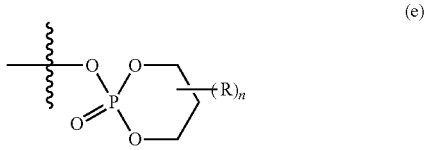
(e)

Wherein, when n is 0, it represents that there is no substituent, that is, it is unsubstituted.

When n is 1, it represents that any one of the substitutable positions on the ring system is alternatively substituted with the substituent.

When n is greater than 1, such as 2, 3 or 4, it represents that there are more than one substituent, such as 2 substituents, 3 substituents or 4 substituents, different or the same substitution position may be substituted with each substituent, and each substituent may be the same or different.

The above-mentioned wavy line represents a connection bond.

The term "pharmaceutically acceptable" refers to the substance or composition must be chemically and/or toxicologically compatible with other ingredients in the formulation and/or a mammal treated therewith.

The "pharmaceutically acceptable salt" of the present disclosure can be synthesized from a parent compound, a basic or acidic moiety by conventional chemical methods. Generally speaking, such salts can be prepared by reacting the free acid form of these compounds with a stoichiometric amount of a suitable base (such as hydroxides, carbonates, bicarbonates, etc. of Na, Ca, Mg or K) or by reacting the free base form of these compounds with a stoichiometric amount of a suitable acid. This type of reaction is usually carried out in water or an organic solvent or a mixture of the two. Generally, where appropriate, it is required to use a non-aqueous medium such as diethyl ether, ethyl acetate, ethanol, isopropanol or acetonitrile. A list of other suitable salts can be found in, for example "Remington's Pharmaceutical Sciences", 20$^{th}$ Edition, Mack Publishing Company, Easton, Pa., (1985); and "Handbook of Pharmaceutical Salts: Properties, Selection, and Use)", Stahl and Wermuth (Wiley-VCH, Weinheim, Germany, 2002).

Besides, the compounds, including their salts, disclosed by the present disclosure may also be obtained in the form of their hydrates or in the form of their solvents (e.g., ethanol, DMSO, etc.) for their crystallization. The compounds disclosed by the present disclosure may form solvates either intrinsically or by design with pharmaceutically acceptable solvents (including water); therefore, the present disclosure is intended to include both solvated and unsolvated forms.

In addition, the compounds disclosed by the present disclosure may be administered in the form of a prodrug. In the present disclosure, the "prodrug" of the compound disclosed by the present disclosure is a functional derivative which can ultimately release the compound disclosed by the present disclosure in vivo when administered to a patient.

The term "prodrug" as used in the present disclosure represents a compound converted to the compound as shown in Formula (I) or Formula (II) in vivo. Such conversion is affected by the hydrolysis of the prodrug in the blood or by enzymatic conversion to the parent structure in the blood or tissue. The prodrug compounds of the present disclosure may be esters. In the art, esters may be used as prodrugs are phenyl esters, aliphatic ($C_1$-$C_{24}$) esters, acyloxymethyl esters, carbonate esters, carbamate esters, and amino acid esters. For example, a compound of the present disclosure comprises hydroxyl, i.e., it can be acylated to obtain a compound in the form of a prodrug. Other prodrug forms include phosphate esters, and these phosphate esters are obtained by phosphorylation of hydroxy on the parent.

"Metabolite" refers to a product obtained by metabolism of a specific compound or a salt thereof in vivo. The metabolite of a compound can be identified by techniques well known in the art, and the activity can be characterized by experimental methods as described by the present disclosure. Such products may be generated by oxidation, reduction, hydrolysis, amidation, deamidation, esterification, defatting, enzymatic cleavage or the like of the administered drugs. Accordingly, the present disclosure includes a metabolite of the compound, such as the metabolites produced by intimately contacting a compound of the present disclosure with a mammal for a period of time.

The "solvate" as used in the present disclosure refers to an association of one or more solvent molecules with a compound of the present disclosure. The solvents may be used to form a solvate include but not limited to, water, isopropanol, ethanol, methanol, dimethyl sulfoxide, ethyl acetate, acetic acid, and aminoethanol. The term "hydrate" refers to an association in which the solvent molecule is water. When the solvent is water, the term "hydrate" may be used. In some examples, a molecule of the compound of the present disclosure may be combined with a water molecule, such as a monohydrate; in other examples, a molecule of the compound of the present disclosure may be combined with more than one water molecule, such as dihydrate; also in other examples, a molecule of the compound of the present disclosure may be combined with less than one water molecule, such as a hemihydrate. It should be noted that the hydrate of the present disclosure retain the bioavailability of the compound in non-hydrated form.

"Pharmaceutically acceptable excipient" as used in the present disclosure is intended to refer to a pharmaceutically acceptable material, mixture or vehicle that is compatible with the administered dosage form or pharmaceutical composition. Each excipient should be compatible with the other ingredients in the pharmaceutical composition when mixed to avoid interactions that would greatly reduce the efficacy of the compounds of the present disclosure and interactions that would result in compositions not pharmaceutically acceptable when administered to a patient. In addition, each excipient should be pharmaceutically acceptable, for example, having sufficiently high purity. Suitable pharmaceutically acceptable excipients will vary depending upon the specific chosen dosage form. In addition, pharmaceutically acceptable excipients can be selected based on their particular function in the composition. For example, certain pharmaceutically acceptable excipients may be selected which can help to produce a uniform dosage form. Certain pharmaceutically acceptable excipients may be selected which can help to produce a stable dosage form. Certain pharmaceutically acceptable excipients may be selected which can help to carry or transport a compound of the present disclosure from one organ or part of the body to another organ or part of the body when administered to a patient. Certain pharmaceutically acceptable excipients may be selected which can help to improve patient compliance. Suitable pharmaceutically acceptable excipients include the following types of excipients: diluents, fillers, adhesives, disintegrants, lubricants, glidants, granulating agents, coating agents, wetting agents, solvents, cosolvents, suspending agents, emulsifiers, sweeteners, flavoring agents, taste masking agents, colorants, anti-caking agents, humectants, chelating agents, plasticizers, tackifiers, antioxidants, preservatives, stabilizers, surfactants, and buffers. A technical person can realize that certain pharmaceutically acceptable excipients may provide more than one function and provide alternative functions depending on how much of the excipients is in the formulation and which other excipients are in the formulation.

The term "aryl group" represents a monocyclic, bicyclic or tricyclic all-carbon ring system containing 6 to 14 ring atoms, or 6 to 12 ring atoms, or 6 to 10 ring atoms, wherein at least one ring is aromatic and having one or more attachment points attached to the remainder of the molecule. Examples of the aryl groups may include phenyl, naphthyl, and anthracenyl. The aryl may be independently and optionally substituted with one or more substituents described by the present disclosure.

The term "heteroaryl" represents a monocyclic, bicyclic or tricyclic ring containing 5 to 12 ring atoms, or 5 to 10 ring atoms, or 5 to 6 ring atoms, wherein at least one of the rings is aromatic and at least one simple aromatic ring contains one or more heteroatoms and having one or more attachment points attached to the remainder of the molecule. Examples of heteroaryl includes but not limited to, furyl, pyridyl, pyrimidinyl, pyrazinyl, pyridazinyl, indolyl, etc.

Compared with the conventional art, the present disclosure provides compounds for treating metabolic diseases, which have a structure as shown in Formula (I) or Formula (II), or a racemate, a stereoisomer, a geometric isomer, a tautomer, a solvate, a hydrate, a metabolite, a pharmaceutically acceptable salt or a prodrug thereof. The above-mentioned compounds provided by the present disclosure target FXR and TGR5, and can regulate bile acid, cholesterol homeostasis, triglyceride synthesis and lipogenesis in vivo. Therefore, it can be used for the treatment of various diseases caused by metabolism of bile acid, cholesterol, and triglyceride. And the compounds of the present disclosure are compounds targeting the liver, having a higher potency than the compounds of the same type, low side effects, and overcome the adverse reactions of other similar compounds in current clinical use.

DETAILED DESCRIPTION

Figure 1:
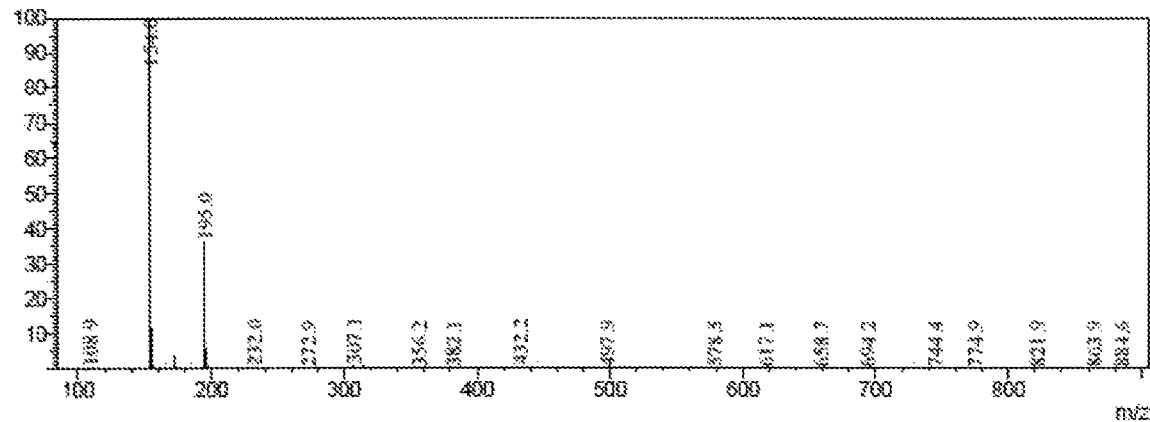
FIG. 1 is a mass spectrum of Compound 14 in Example 1.

In order to further illustrate the present disclosure, the compounds for treating metabolic diseases and preparation method and use thereof provided by the present disclosure are described in detail below with reference to the examples. The proportions of the solvents in the following examples are volume ratios unless otherwise stated. For example, ethyl acetate:petroleum ether=1:5 represents that the volume ratio of ethyl acetate to petroleum ether is 1:5.

Example 1 Synthesis of Compound 1 (i.e. Compound 1-H)

1. Synthesis of Compound 2

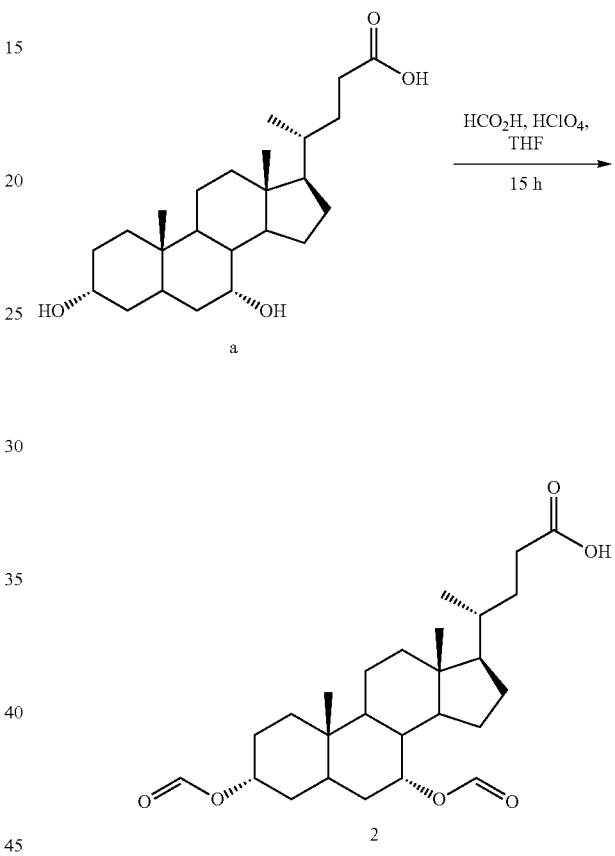

300 mL of tetrahydrofuran was added into a 1000 mL round-bottom flask, then 30 g of chenodeoxycholic acid (as shown in Formula a) (76.42 mmol) was added, and 3 mL of perchloric acid was added, and 100 mL of formic acid was added with stirring at room temperature. The temperature was controlled to be 50° C. and the reaction was carried out under stirring for 15 hours. The solvent was removed by concentration under reduced pressure. The residue was diluted with 4 L of water, the solid was collected by filtration, and 2 L of dichloromethane was added to dissolve the solid. The solution was dried with anhydrous sodium sulfate, filtered and then concentrated under reduced pressure. The crude product was dispersed and stirred with 4 L of petroleum ether, and a white solid was collected by filtration to obtain 32.8 g of Compound 2, with a yield of 98%.

2. Synthesis of Compound 3

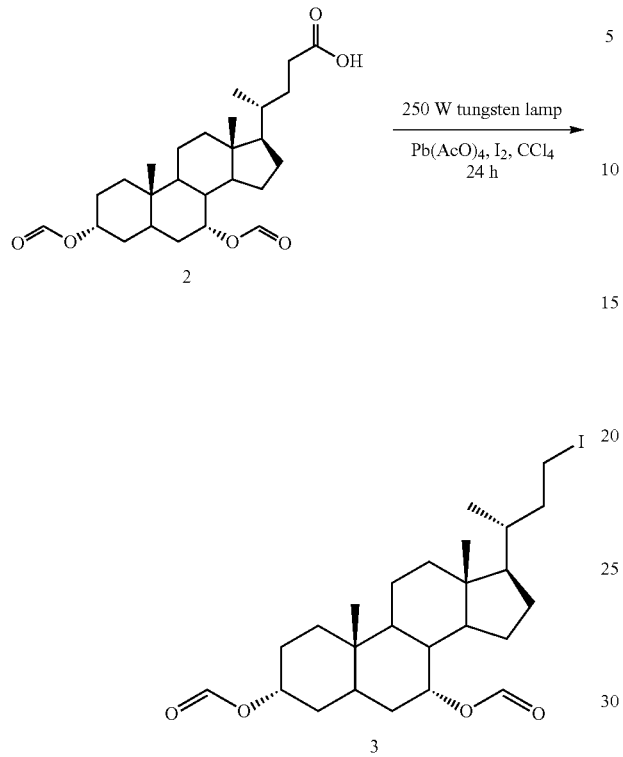

Under protection of argon, 100 g of Compound 2 (222.92 mmol), 3 L of carbon tetrachloride, 199.1 g of lead acetate (446.41 mmol), and 113.64 g of iodine (447.40 mmol) were sequentially added into a 5 L round-bottom flask. The obtained reaction solution was stirred at 20° C. for 24 hours under irradiation of a tungsten lamp (250 watts). 3 L of saturated sodium thiosulfate was added to quench the reaction. The solid was removed by filtration. The filtrate was extracted twice with dichloromethane, 3 L each time. The organic phases were combined, 2 L of saturated sodium thiosulfate were added respectively, washed twice, and then washed once with 2 L of water and once with 2 L of saturated aqueous solution of sodium chloride. The organic phase was dried with anhydrous sodium sulfate, filtered and concentrated under reduced pressure. 110 g of light yellow solid Compound 3 was obtained, with a yield of 93%.

3. Synthesis of Compound 4

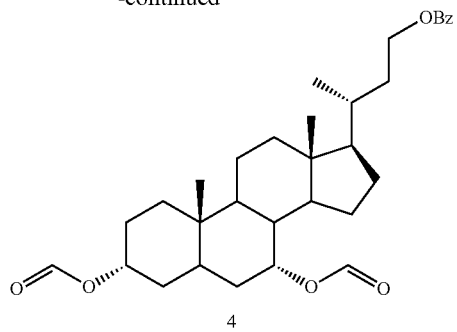

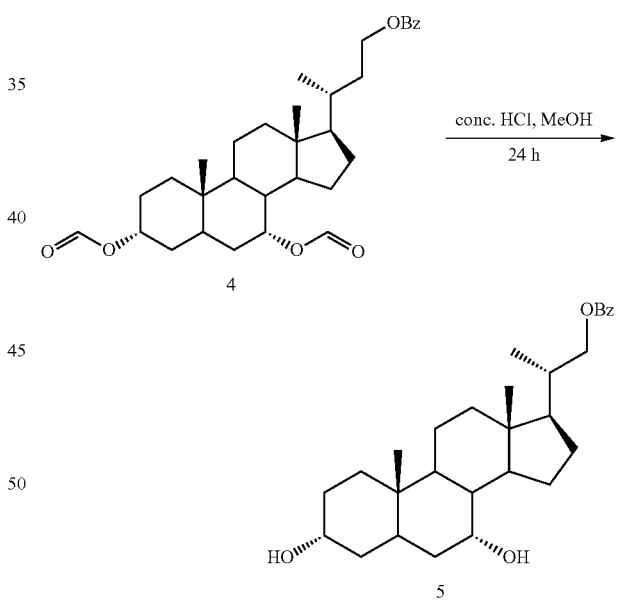

Compound 3 (250 g, 471.27 mmol), 150.9 g of potassium benzoate (941.88 mmol), 2 L of N,N-dimethylformamide were added sequentially into a 3 L round-bottom flask at room temperature. The reaction solution was stirred at 80° C. for 15 hours and concentrated under reduced pressure. The residue was dissolved in 3 L of dichloromethane. The solution was washed twice with 1.6 L of water, and then once with 1.6 L of saturated sodium thiosulfate and once with 1.6 L of saturated sodium chloride sequentially. The organic phase was dried with anhydrous sodium sulfate, filtered and concentrated under reduced pressure. 310 g of brown Compound 4 was obtained and used for the next reaction without purification.

4. Synthesis of Compound 5

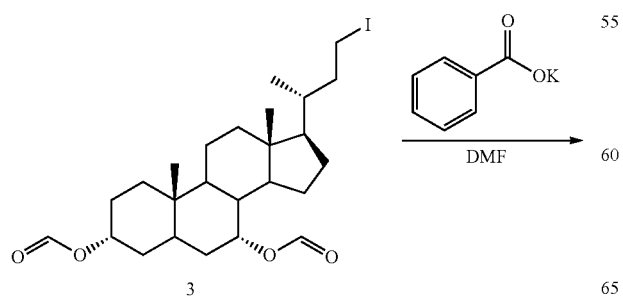

1 L of methanol was added into a 2 L round-bottom flask, and 35 g of crude Compound 4 was dissolved in the methanol (1000 mL), then 20 mL of concentrated hydrochloric acid was added. The reaction solution was stirred at 20° C. for 24 hours, and concentrated under reduced pressure. The residue was dissolved in 3 L of dichloromethane. The solution was washed twice with 800 mL of a saturated aqueous solution of sodium bicarbonate and once with 800 mL of a saturated aqueous solution of sodium chloride. The organic phase was dried with anhydrous sodium sulfate, filtered and concentrated. The residue was purified by silica gel column chromatography (dichloromethane:methanol=80:1). 22.8 g of Compound 5 was obtained (a yield of 60%, a yellow solid).

5. Synthesis of Compound 6

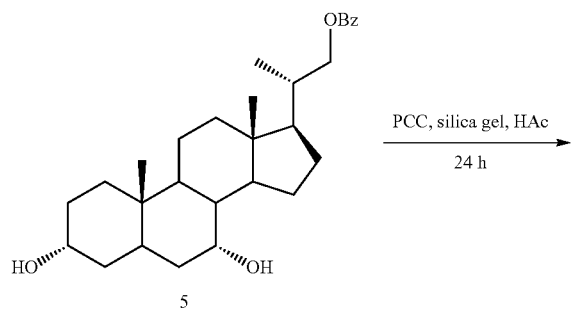

1 L of chloroform was added into a 2 L round-bottom flask, and 35 g (74.68 mmol) of Compound 5 was dissolved in chloroform solvent, then a mixture of pyridinium chlorochromate (17.687 g, 82.30 mmol) and silica gel (140 g) were added, and then 35 mL of acetic acid was added dropwise. The reaction solution was stirred at 20° C. for 24 hours, and the reaction solution was diluted with a mixed solution of 4 L of dichloromethane and 40 mL of methanol. A solid was obtained by filtration. The filtrate was respectively washed twice with 1.2 L of water and once with 1.2 L of a saturated sodium chloride solution. The organic phase was dried with anhydrous sodium sulfate, filtered and concentrated. The residue was purified by silica gel column chromatography (dichloromethane:methanol=100:1) to obtain 23 g of Compound 6 (a yield of 60%, a yellow solid).

6. Synthesis of Compound 7

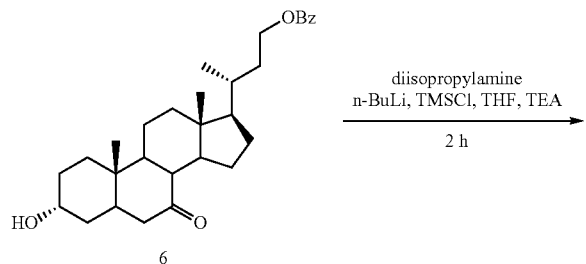

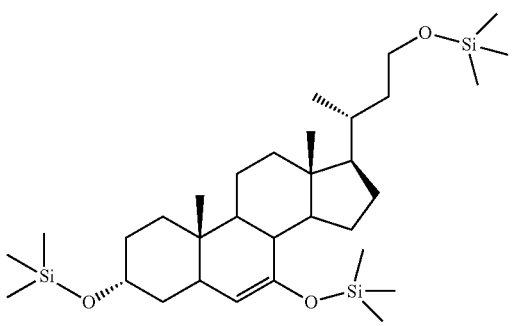

1.2 L of tetrahydrofuran was added into a 5 L three-neck flask, diisopropylamine (182 g, 1.80 mol) was dissolved in tetrahydrofuran, 2.5 M n-butyllithium in tetrahydrofuran solution (721 mL) was added dropwise at −78° C., stirred at −78° C. for half an hour after the completion of the addition. Then trimethylsilyl chloride (160.3 g, 1.50 mol) was added dropwise at −78° C., and stirred at −78° C. for half an hour. Then, a mixed solution of Compound 6 (70 g, 0.15 mol) and tetrahydrofuran (900 mL) was added dropwise to the above-mentioned solution at −78° C., and stirred at −78° C. for half an hour. Triethylamine (272.3 g, 2.70 mol) was added dropwise at −78° C. Then the temperature was raised to 20° C., and stirring was carried out for 2 hours. 2.1 L of a saturated aqueous solution of sodium bicarbonate was added to quench the reaction. The reaction solution was extracted with 6 L of ethyl acetate. The organic phases were combined, respectively washed twice with 1.2 L of water, five times with a saturated aqueous solution of ammonium chloride, and once with 1.2 L of a saturated aqueous solution of sodium chloride. The organic phase was dried with anhydrous sodium sulfate, filtered and concentrated. 145 g of crude Compound 7 was obtained and used directly for the next step of reaction.

7. Synthesis of Compound 8

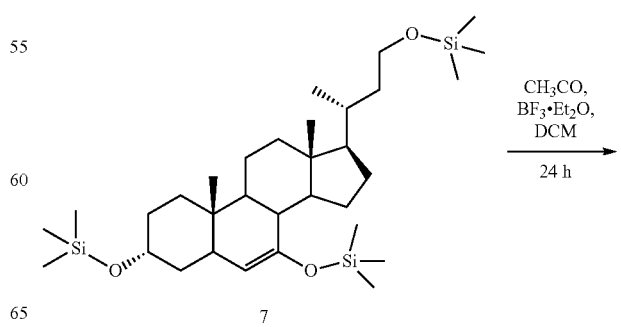

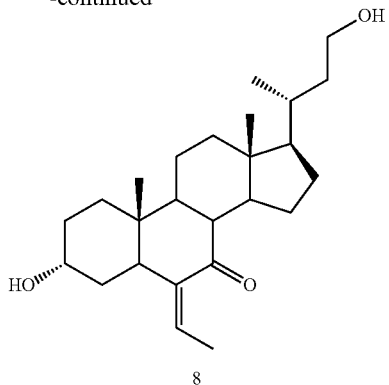

Under protection of argon, a mixed solution of Compound 7 (40 g, 69.07 mmol) and dichloromethane (600 mL) was added into a three-neck flask. Acetaldehyde (6.506 g, 147.86 mmol) was added to the solution, and boron trifluoride-diethyl etherate (69.99 g, 492.89 mmol) was added dropwise at −60° C. The reaction solution was stirred at 20° C. for 24 hours. The pH of the reaction solution was adjusted to 7 to 8 with a saturated aqueous solution of sodium hydrogen carbonate. The reaction solution was diluted with 100 mL of water, and then extracted three times with 700 mL of dichloromethane, and the organic phases were combined. The organic phase was respectively washed twice with 1 L of water, once with 1 L of a saturated aqueous solution of sodium chloride, and then dried with anhydrous sodium sulfate, filtered and concentrated. The residue was purified by silica gel column chromatography (dichloromethane:methanol=100:1) to obtain 10 g of Compound 8 (a yield of 37%, a white solid).

8. Synthesis of Compound 9

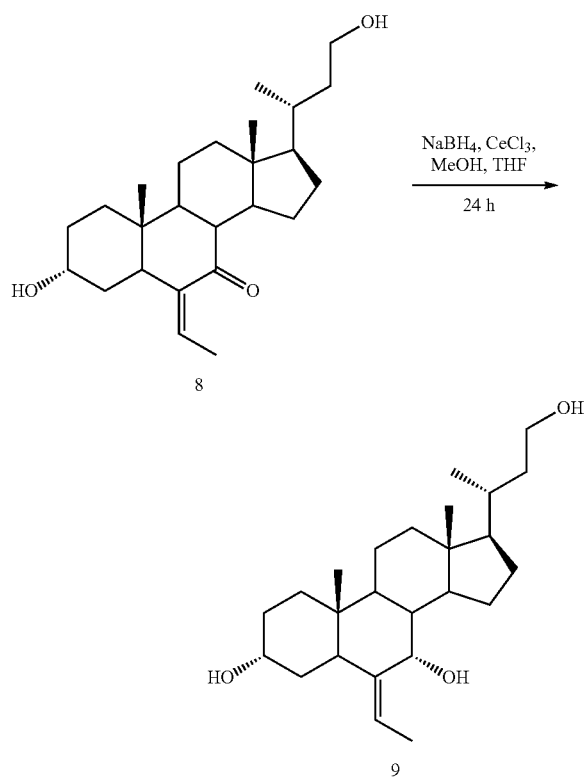

Under protection of nitrogen, 100 mL of tetrahydrofuran, Compound 8 (5 g, 12.87 mmol), methanol 25 mL, cerium (III) chloride (19.17 g, 51.46 mmol), and sodium borohydride (1.85 g, 51.39 mmol) were added into a 250 mL three-neck flask. The solution was reacted at 20° C. for 24 hours. Then 3 L of a saturated aqueous solution of ammonium chloride was added to quench the reaction. The reaction solution was concentrated under reduced pressure. The residue was diluted with 300 mL of water and extracted three times with 600 mL of dichloromethane, and the organic phases were combined. The organic phase was respectively washed once with 300 mL of a saturated aqueous solution of sodium bicarbonate, once with 300 mL of a saturated aqueous solution of sodium chloride, and then dried with anhydrous sodium sulfate, filtered and concentrated. 4.8 g of Compound 9 was obtained (a yield of 96%, a yellow solid).

9. Synthesis of Compound 10

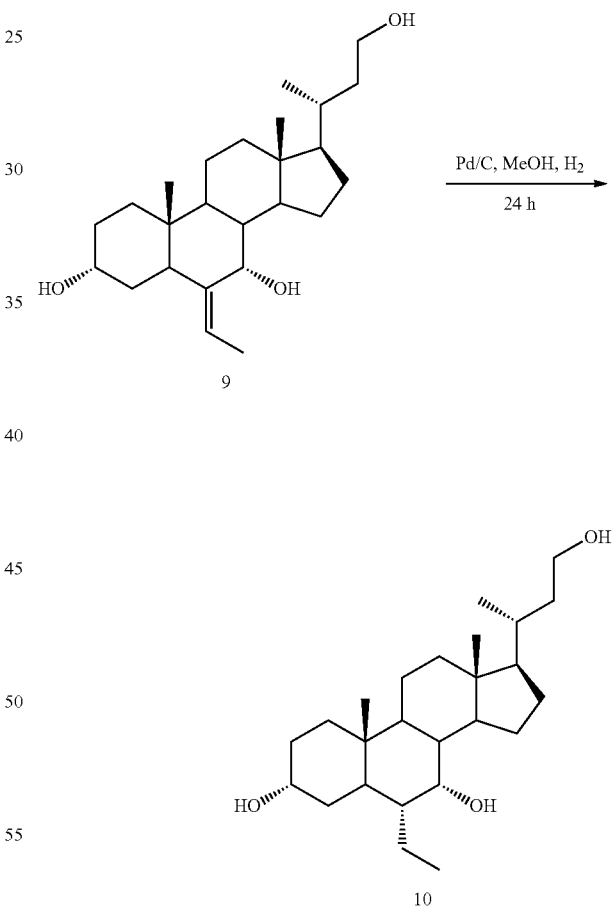

80 mL of methanol, Compound 9 (8 g, 20.48 mmol) and 10% Pd/C (4 g, 3.77 mmol) were added into a 250 mL round-bottom flask, and hydrogen was introduced and reacted at 40° C. for 24 hours. The reaction solution was filtered and concentrated. The residue was purified by silica gel column chromatography (dichloromethane:methanol=100:1) to obtain 5.6 g of Compound 10 (a yield of 70%, a white solid).

10. Synthesis of Compound 11

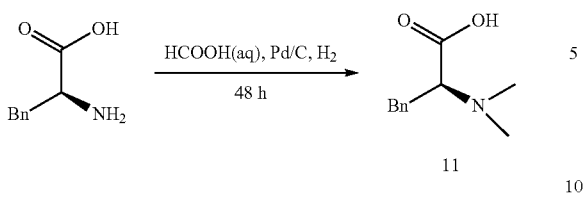

Under protection of argon, a mixed solution of (2S)-2-amino-3-phenylpropionic acid (250 g, 1.51 mol) and 3.5 L of water were added into a 5 L three neck flask, then formic acid (491.75 g, 6.04 mol) was added. 4% Pd/C (250 g, 94.34 mmol) was added at 20° C. Hydrogen was introduced and the reaction was carried out at 20° C. for 48 hours. The resultant was filtered and concentrated. The crude product was recrystallized from methanol, and the solid was collected by filtration to obtain 190 g of Compound 11 (a yield of 65%, a white solid).

$^1$H-NMR: (CD3OD, 400 MHz, ppm): 7.25-7.40 (m, 5H), 3.86 (t, J=6.9 Hz, 1H), 3.37-3.31 (m, 1H), 3.24 (dd, J=14.6, 6.8 Hz, 1H), 2.85 (s, 6H).

11. Synthesis of Compound 12

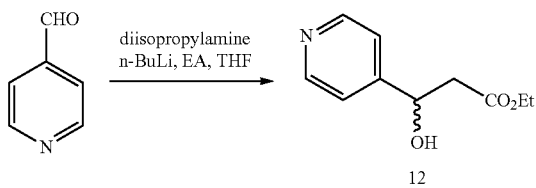 [SMILES: O=Cc1ccncc1 ; CCOC(=O)CC(O)c1ccncc1]

Under protection of nitrogen, 700 mL of a mixed solution of tetrahydrofuran and diisopropylamine (188.6 g) was added into a 3 L three neck flask. n-Butyllithium (2.5 M tetrahydrofuran, 746 mL) was added dropwise within 30 minutes at −78° C. The temperature of the reaction was raised to 20° C., and the reaction was carried out under stirring for 20 minutes. Then, a mixed solution of ethyl acetate (164.4 g, 1.87 mol) and tetrahydrofuran (200 mL) was added dropwise at −78° C. within 30 minutes, and the solution was stirred at −78° C. for 1 hour. A mixed solution of 4-pyridinecarboxaldehyde (100 g, 933.62 mmol) and 250 mL of tetrahydrofuran were added dropwise at −78° C. within 25 minutes. The temperature of the reaction was raised to 0° C., and the reaction was carried out under stirring for 1.5 hours. 3.6 L of 1N hydrochloric acid was added to quench the reaction. The solution was extracted three times with 1 L of ethyl acetate. The organic phases were combined, dried with anhydrous sodium sulfate, filtered, and the filtrate was concentrated. The residue was purified by silica gel column chromatography (ethyl acetate: petroleum ether=1:1) to obtain yellow oily Compound 12 (a yield of 80%, 146 g).

12. Synthesis of Compound 13

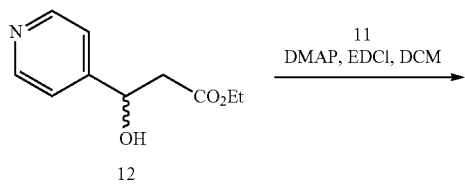

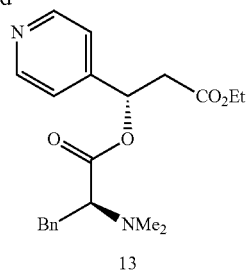

Under protection of nitrogen, a mixed solution of Compound 12 (29.7 g, 153.69 mmol) and dichloromethane (300 mL) was added to a 1 L three-neck flask, and then N-(3-dimethylaminopropyl)-N'-ethylcarbodiimide hydrochloride (36.9 g, 192.49 mmol), 4,4-dimethylaminopyridine (1.56 g, 12.77 mmol), Compound 11 (25 g, 128.06 mmol) were added. The reaction solution was stirred at 20° C. for 5 hours, and after the completion of the reaction, the solution was diluted with 300 mL of dichloromethane. The reaction mixture was washed twice with 500 mL of a saturated aqueous solution of sodium carbonate, once with 500 mL of water, and once with 500 mL of a saturated aqueous solution of sodium chloride. The organic phase was dried with anhydrous sodium sulfate, filtered and concentrated. The residue was purified by silica gel column chromatography (ethyl acetate:petroleum ether=1:5). The obtained crude product was purified again by Flash-Prep-HPLC, petroleum ether (containing 0.1% triethylamine)/ethyl acetate (containing 0.1% triethylamine)=35:65, to increase the polarity to ethyl acetate (containing 0.1% triethylamine), to obtain yellow solid Compound 13 (a yield of 32%, 15 g).

13. Synthesis of Compound 14

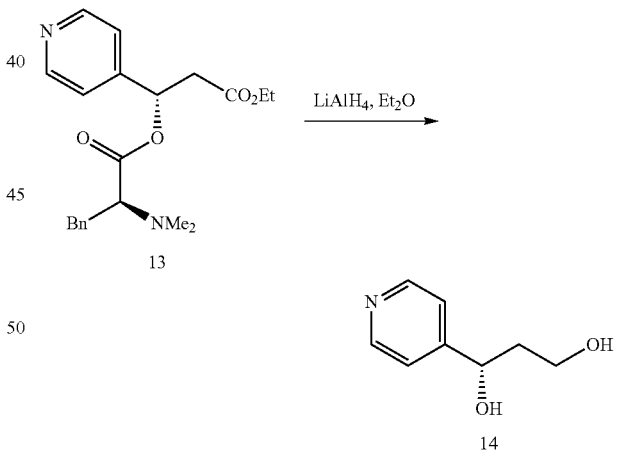

Under protection of nitrogen, 900 mL of diethyl ether was added into a 2 L three-neck flask, the temperature was decreased to −20° C., and lithium aluminum hydride (18.5 g, 487.48 mmol) was added. Then, a mixed solution of Compound 13 (30 g, 80.98 mmol) and diethyl ether (300 mL) was added dropwise at −20° C. The reaction solution was stirred at −20° C. for 3 hours. 400 mL of ethyl acetate was added to quench the reaction. Then, 40 mL of a saturated aqueous solution of sodium sulfate and 150 mL of methanol were added, stirred at 20° C. for 1 hour, filtered and concentrated. The residue was purified by silica gel column chromatography (dichloromethane:methanol=20:1). The crude product was recrystallized from ethyl acetate to obtain white solid Compound 14 (PH-MKA-MT2002-8, 7.74 g, a yield of 62%).

LCMS: (ES, m/z): 154[M+H]$^+$.

The mass spectrum is as shown in FIG. 1.

The liquid phase data is as shown in Table 1 below:

TABLE 1

Compound 14 liquid phase data

| Peak position | Peak area |
|---|---|
| 0.64 min | 810059 |

14. Synthesis of Compound 15

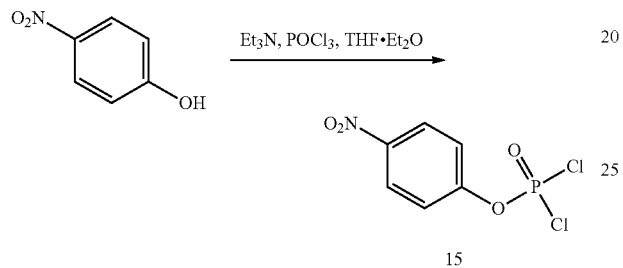

Under protection of argon, 400 mL of tetrahydrofuran and 250 mL of diethyl ether were added to a 3 L three-neck flask. Phosphoryl chloride (77.2 g, 503.49 mmol, 1.00 eq.) was added to the three-neck flask. A mixed solution of sodium 4-nitrophenolate (70 g, 503.20 mmol), triethylamine (50.96 g, 503.61 mmol), tetrahydrofuran (400 mL) and diethyl ether (250 mL) was slowly added to the reaction system at −78° C. The temperature of the reaction was raised to 20° C. and the reaction was carried out for 24 hours. The solid was filtered and the filtrate was concentrated. The crude product was purified by vacuum distillation (5 mmHg), and the fraction at 180° C. was collected to obtain bright yellow oily Compound 15 (38 g, a yield of 29%).

P-NMR: (CDCl$_3$, 121.5 MHz, ppm): 3.35

15. Synthesis of Compound 16

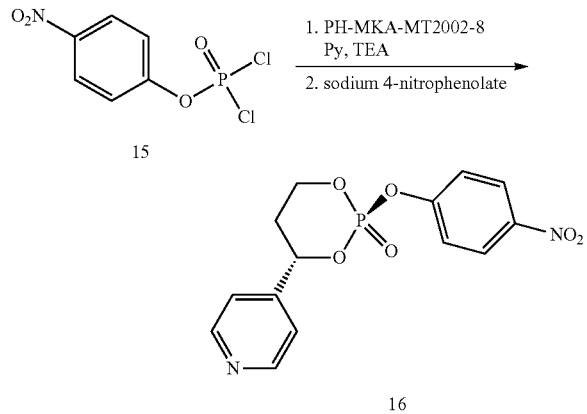

Under protection of nitrogen, a mixed solution of Compound 14 (27 g, 176.27 mmol), pyridine (210 mL) and triethylamine (3.024 g, 29.88 mmol) was added into a 1000 mL three-neck flask. A mixed solution of Compound 15 (45 g, 175.79 mmol) and pyridine (360 mL) was added dropwise at 0° C. to 5° C. The reaction solution was stirred at 20° C. for 5 hours. After the disappearance of the raw material, sodium 4-nitrophenolate (113.4 g, 704.35 mmol, 4.00 equiv) was added. After the completion of the addition, the solution was stirred at 40° C. for 4 hours, and then stirred at 20° C. for 16 hours. The reaction solution was concentrated. The residue was dissolved in 1.5 L of hydrochloric acid (2 mol/L), and washed twice with 1.5 L of ethyl acetate. The separated aqueous phase was adjusted to a pH of 7 to 8 with sodium bicarbonate, and then extracted three times with 1.2 L of dichloromethane. The organic phase was dried with anhydrous sodium sulfate, filtered and concentrated. The residue was purified by Flash-Prep-HPLC to obtain off-white solid Compound 16 (35 g, a yield of 59%).

LC-MS: (ES, m/z): 337[M+H]$^+$.

$^1$H-NMR: (DMSO, 400 MHz, ppm): 8.62-8.62 (m, 2H), 8.35-8.31 (m, 2H), 7.59-7.57 (m, 2H), 7.44-7.42 (m, 2H), 5.91 (dd, J=10.1, 3.7 Hz, 1H), 4.71-4.56 (m, 2H), 2.32-2.17 (m, 2H).

P-NMR: (DMSO, 162 MHz, ppm): −14.08.

Figure 2:
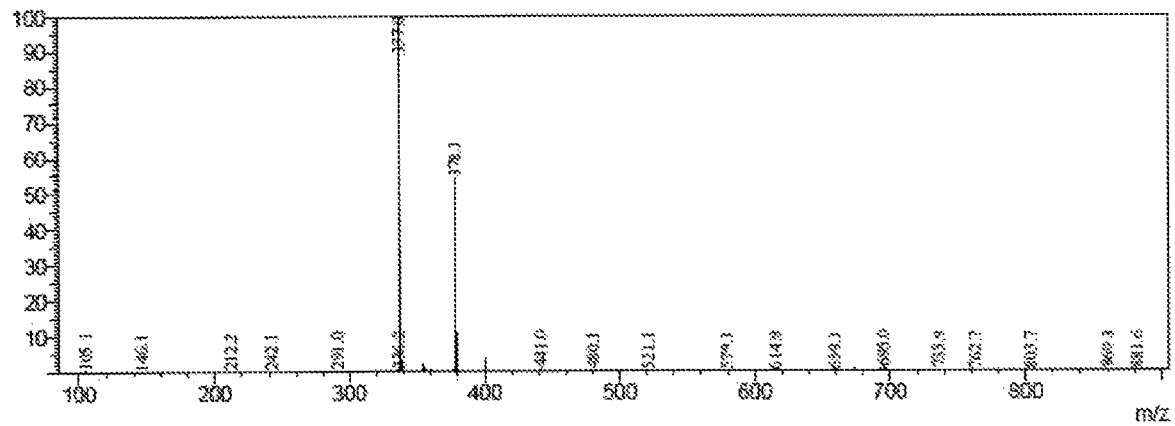
FIG. 2 is a mass spectrum of Compound 16 in Example 1.

The mass spectrum is as shown in FIG. 2.

The liquid phase data is as shown in Table 2 below:

TABLE 2

Compound 16 liquid phase data

| Peak position | Peak area |
|---|---|
| 1.088 | 5970276 |
| 1.278 | 14725 |

Figure 3:
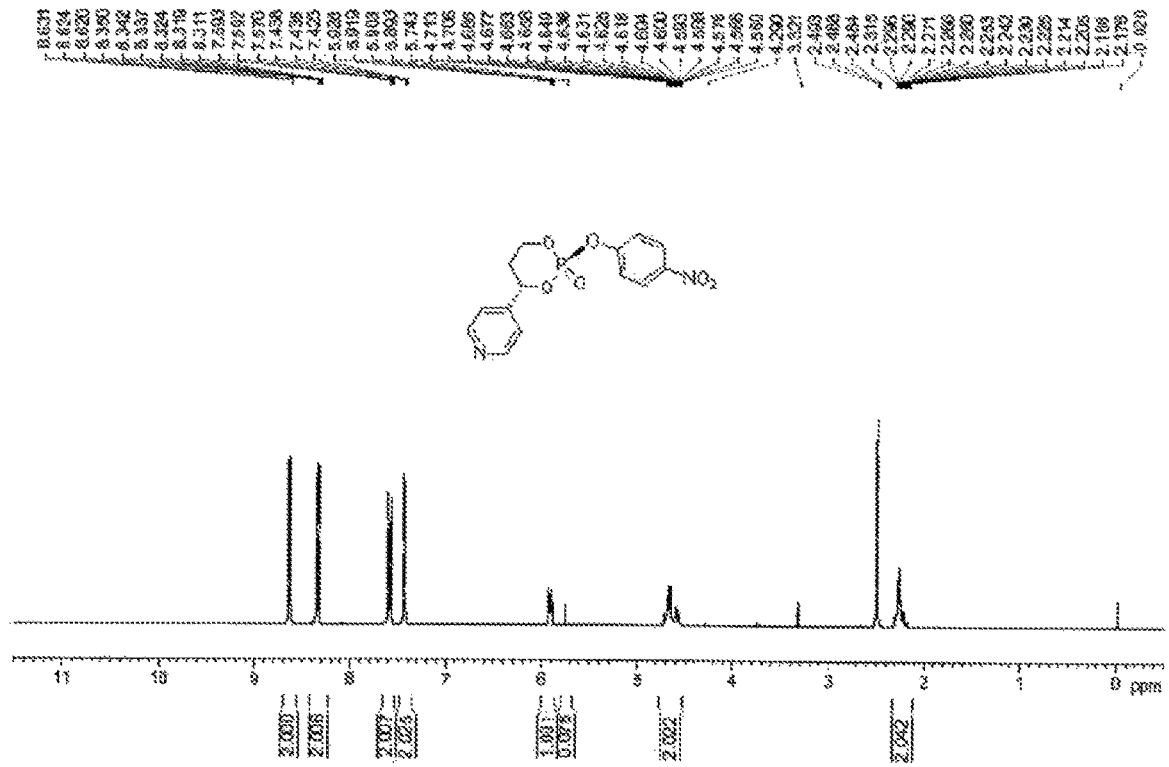
FIG. 3 is a proton nuclear magnetic resonance spectrum of Compound 16 in Example 1.

The hydrogen spectrum is as shown in FIG. 3.

16. Synthesis of Compound 1 (i.e. Compound 1-H)

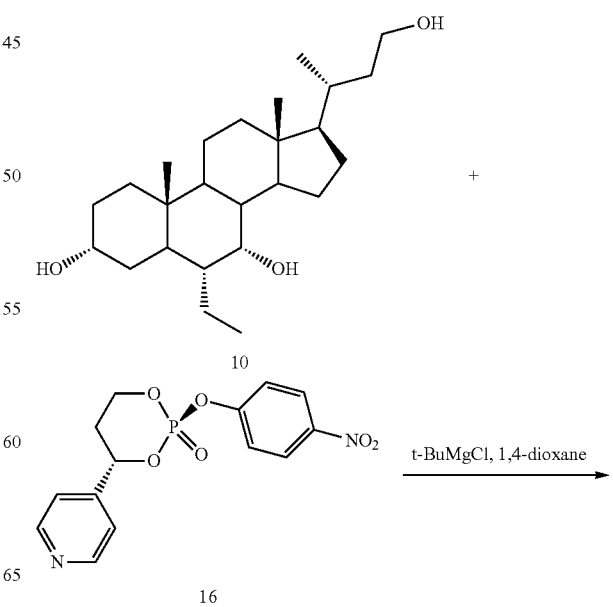

-continued

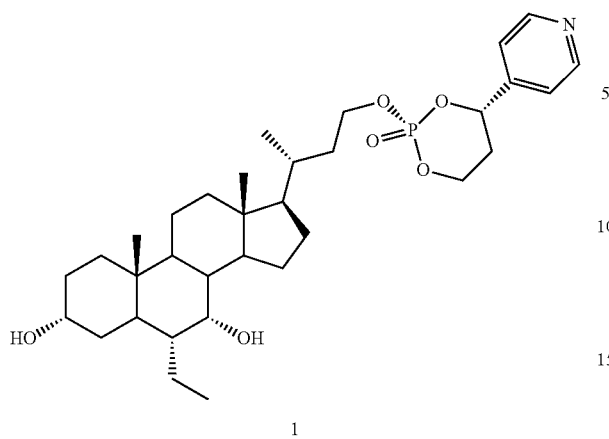

1

Under protection of argon, a mixed solution of Compound 10 (500 mg, 1.27 mmol) and 1,4-dioxane (6 mL) was added to a 25 mL three-neck flask, tert-butylmagnesium chloride (6.37 mL, 1 mol/L) was added dropwise at 20° C., stirred at 20° C. for 4 hours, Then, a mixed solution of Compound 16 (855.8 mg, 2.55 mmol) and 1,4-dioxane (15 mL) was added dropwise at 65° C., and stirred at 65° C. for 2 hours. 100 mL of saturated ammonium chloride solution was added to quench the reaction. The reaction solution was extracted twice with 100 mL dichloromethane. The organic phases were combined. The organic phase was washed once with 150 mL of saturated sodium chloride solution, dried with anhydrous sodium sulfate, filtered and concentrated. The residue was purified by silica gel column chromatography (dichloromethane:methanol=20:1). The crude product was purified by Flash-Prep-HPLC to obtain off-white solid Compound 1 (i.e. Compound 1-H, 30 mg), and the purity was 96.8%.

LC-MS: (ES, m/z): 590.2[M+H]$^+$.

$^1$H-NMR: (CD3OD, 400 MHz, ppm): 8.60-8.58 (m, 2H), 7.51-7.49 (m, 2H), 5.76 (m, 1H), 4.68 (ddt, J=15.0, 7.2, 4.4 Hz, 1H), 4.58-4.44 (m, 1H), 4.30-4.19 (m, 2H), 3.45 (tt, J=10.6, 4.5 Hz, 1H), 3.12-3.02 (m, 1H), 2.34-2.23 (m, 2H), 2.08-1.77 (m, 6H), 1.74-1.41 (m, 9H), 1.41-1.02 (m, 10H), 1.01 (d, J=6.4 Hz, 3H), 0.95 (s, 3H), 0.86 (t, J=7.4 Hz, 3H), 0.70 (s, 3H).

P-NMR: (CD3OD, 162 MHz, ppm): −4.998.

Figure 4:
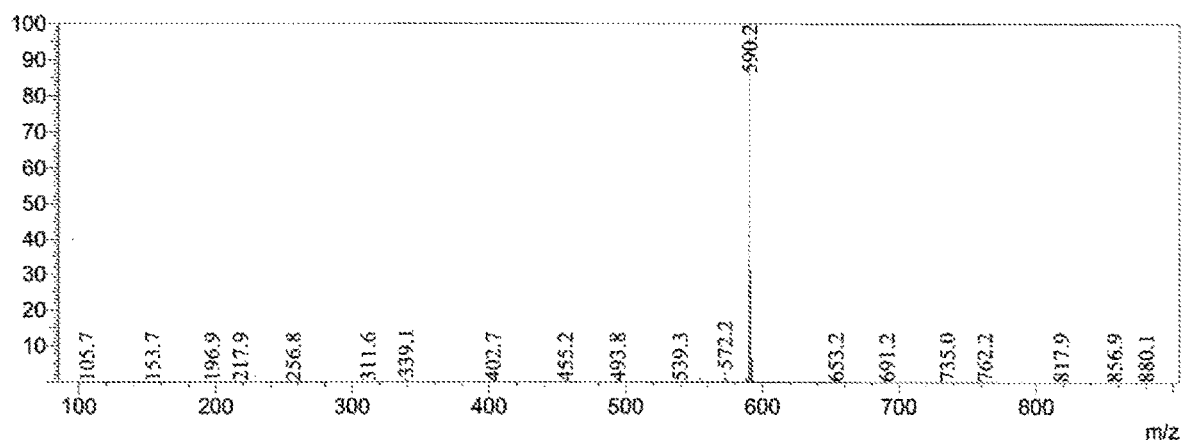
FIG. 4 is a mass spectrum of Compound 1 in Example 1.

The mass spectrum is as shown in FIG. 4.

The liquid phase data is as shown in Table 3 below:

TABLE 3

Compound 1 liquid phase data

| Peak position | Peak area |
|---|---|
| 3.722 | 285 |
| 3.819 | 249727 |

Figure 5:
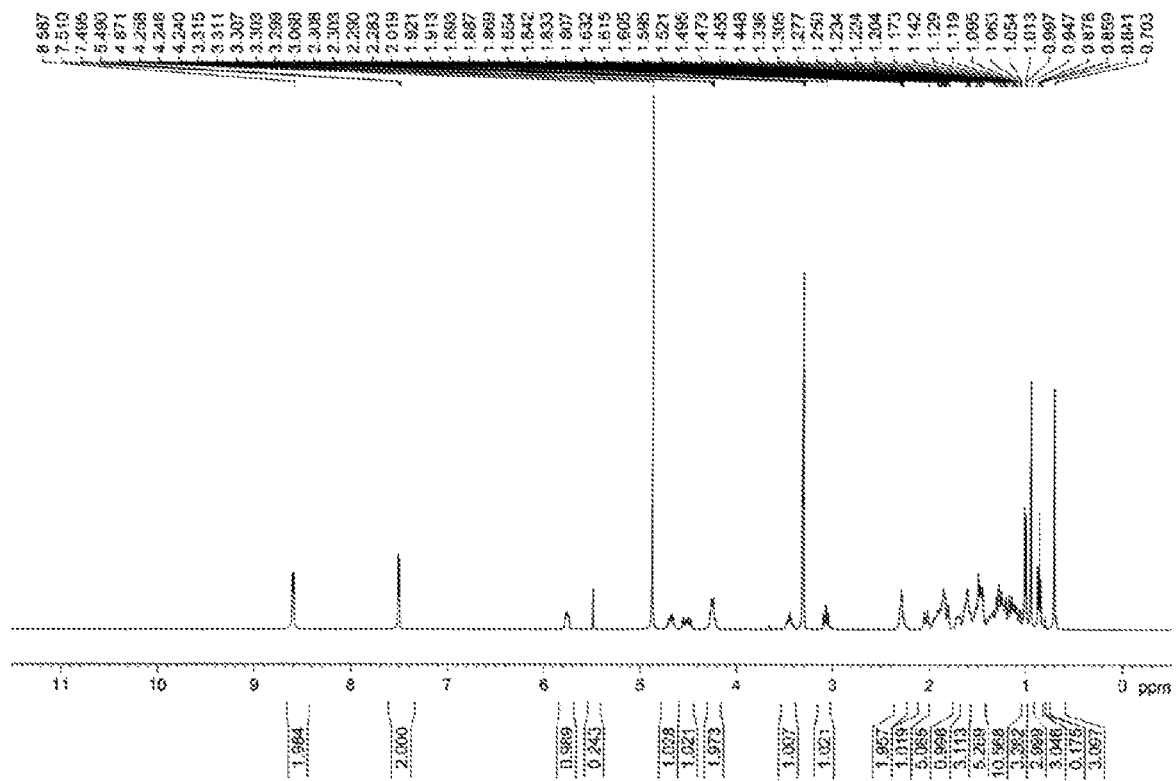
FIG. 5 is a proton nuclear magnetic resonance spectrum of Compound 1 in Example 1.

The hydrogen spectrum is as shown in FIG. 5.

Example 2 Synthesis of Compound 2-0

1. Synthesis of Compound 2-1

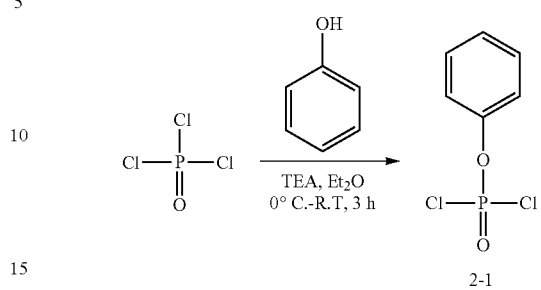

A volume of anhydrous diethyl ether was added into a three-neck flask, then phenol (1000 g, 1.0 eq) and triethylamine (1070 g, 1.0 eq) were added. Phosphoryl chloride (1600 g, 1.0 eq) was added dropwise with stirring at 0° C., and the reaction was carried out under protection of nitrogen for 3 hours. The reaction system was allowed to stand and warm back to room temperature and stay overnight. After the completion of the reaction, the triethylamine salt was quickly filtered off. The filtrate was collected and concentrated, and dried to obtain an oily product Compound 2-1, which was used directly in the next step of reaction without further purification.

2. Synthesis of Compound PH-MIK-001-21

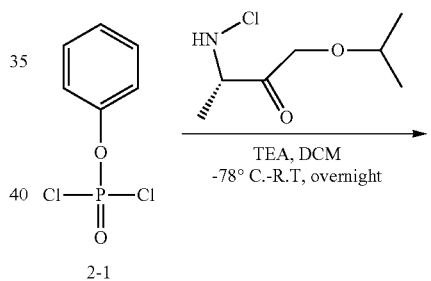

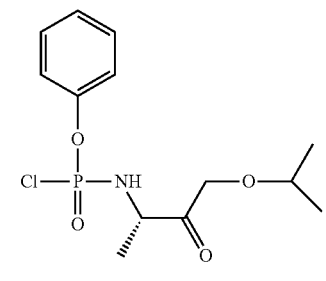

PH-MIK-001-21

A volume of anhydrous dichloromethane (20 L) was added into a three-neck flask, then triethylamine (770 g, 2.0 eq.) was added. The reaction system was placed at −78° C., a solution of Compound 2-1 (800 g, 1.0 eq) dissolved in anhydrous dichloromethane, and (S)-3-(Chloroamino)-1-isopropoxybutan-2-one (685 g, 1.0 eq) were added dropwise, and the reaction was carried out for 2 h after the addition. The reaction system was allowed to stand and warm back to room temperature for overnight. The solvent was removed. The residue was washed with ethyl acetate and then filtered. The filtrate was concentrated and dried to obtain Compound PH-MIK-001-21 (800 g), which was used directly in the next step of reaction without further purification.

3. Synthesis of Compound 2-3

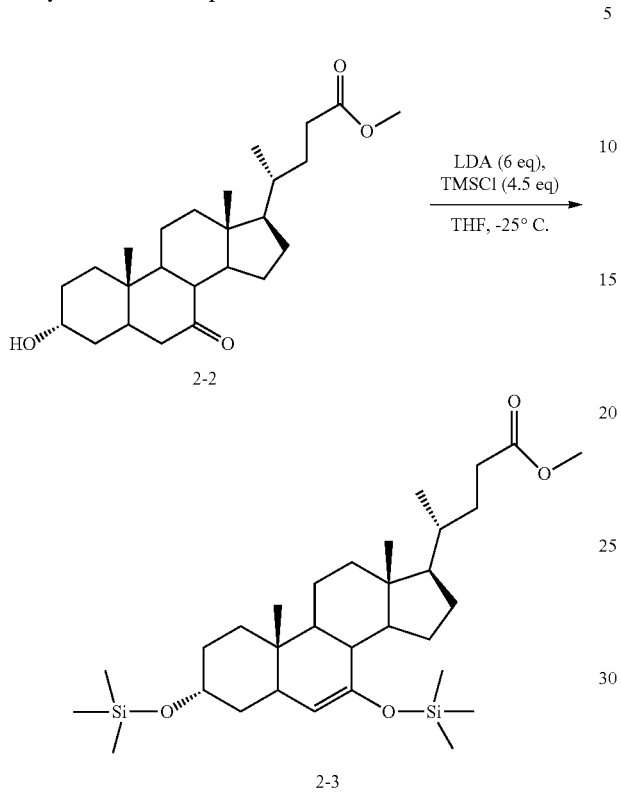

Compound 2-2 (700 g, 1.73 mol, 1.00 eq.) was added into tetrahydrofuran solvent, placed at −25° C. under protection of nitrogen and TMSCl (840 g, 7.79 mol, 4.5 eq) was added dropwise. After 1 hour of reaction, LDA (5.2 L, 2.0 M in THF, 1.00 eq.) was added dropwise for approximately 1 hour. After the completion of the addition, the reaction was carried out at the same temperature for 2 hours. After the completion of the reaction, a pre-cooled aqueous solution of citric acid was added to quench the reaction. The water phase was discarded. The organic phase was dried with anhydrous sodium sulfate and concentrated to obtain 820 g of a yellow oily crude product of Compound 2-3, which was used directly in the next step of reaction without further purification.

4. Synthesis of Compound 2-4

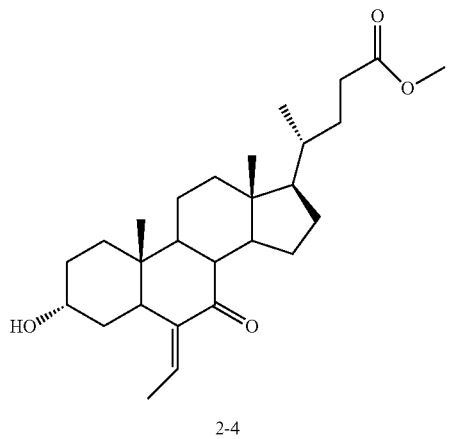

Crude compound 2-3 (820 g, 1.49 mol, 1.00 eq.) was added to 4.5 L of anhydrous dichloromethane and stirred at −60° C. Acetaldehyde (120 g, 2.72 mol, 1.8 eq.) was added dropwise for about 1 hour, and then BF3.Et2O (695 mL, 3.6 eq.) was added dropwise for about 1.5 hour. After the completion of the addition, the reaction system was allowed to react at this temperature for 2 hours, then continued to react at room temperature for 3 hours. The reaction system was cooled to lower than 0° C., a 50% aqueous solution of sodium hydroxide (320 mL) was added to quench the reaction, and stirred well for 10 minutes. Finally, the water phase was discarded. The organic phase was collected, washed with an aqueous solution of sodium chloride, dried with anhydrous sodium sulfate, and concentrated to obtain 750 g of yellow oily crude product of Compound 2-4, which was used directly in the next step of reaction without further purification.

5. Synthesis of Compound 2-5

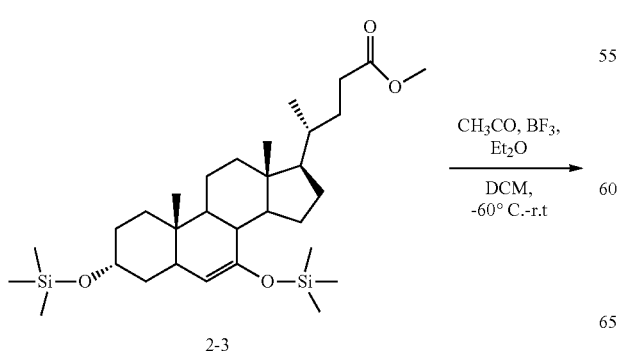

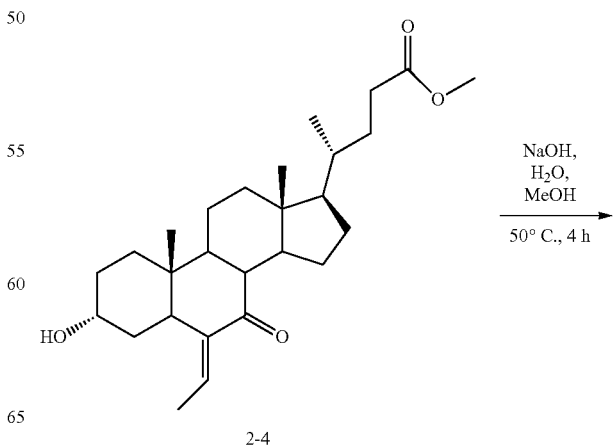

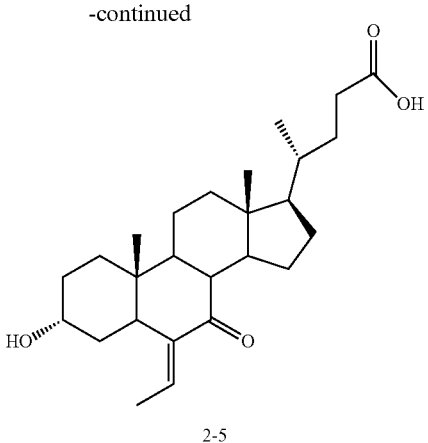

2-5

The crude product of Compound 2-4 was dissolved in a mixed solution of methanol/water (2.5/0.5 L), and added to a sodium hydroxide solution (a 50% aqueous solution of sodium hydroxide, 180 mL) with stirring at room temperature. The reaction system was allowed to react at 50° C. for 4 hours. After the completion of the reaction, the methanol solution was concentrated, and acidified with citric acid and extracted twice with ethyl acetate. The organic phase was collected and washed with a saturated aqueous solution of sodium chloride, dried with anhydrous sodium sulfate and concentrated. Finally, recrystallization was performed in ethyl acetate to obtain 440 g of yellow solid Compound 2-5. The total yield of three steps was 60%.

LC-MS: (ES, m/z): 415 [M–H]⁻.

6. Synthesis of Compound 2-6

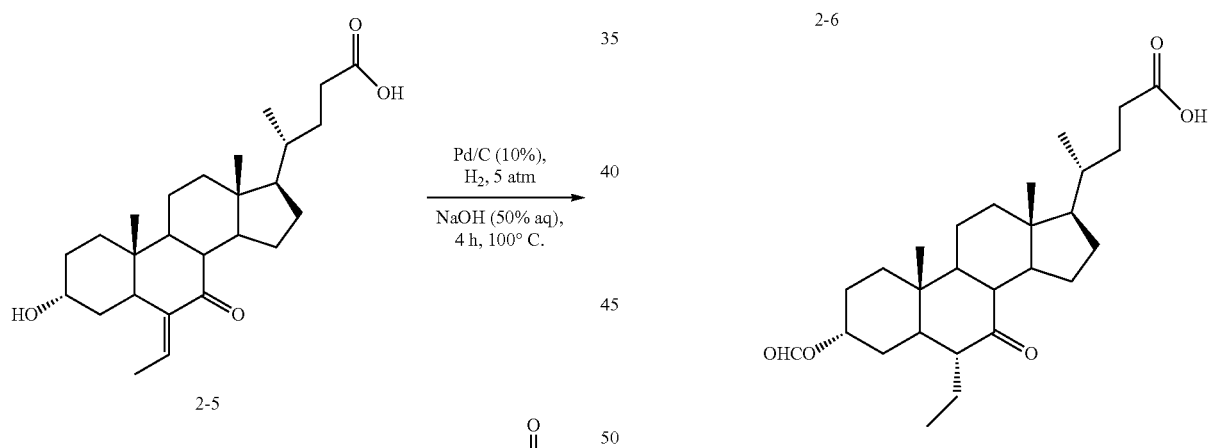

Compound 2-5 (100 g, 0.24 mol, 1.00 eq.) was dissolved in water (1000 mL), and sodium hydroxide (18 g, 0.45 mol, 1.88 eq.) was added with stirring. After it was dissolve completely, Pd/C (10%, 10 g, 0.1 eq.) was added under protection of nitrogen. After the completion of the addition, it was displaced with hydrogen and maintained at a hydrogen pressure of 5 atm, and reacted at 100° C. for 4 hours. After the completion of the reaction, the solid was filtered off, and the filtrate was acidified with hydrochloric acid, and extracted twice with ethyl acetate, washed with a saturated aqueous solution of sodium chloride, dried with anhydrous sodium sulfate and concentrated. Finally, recrystallization was performed in methyl tert-butyl ether:n-hexane=1:2 to obtain 75 g of white solid Compound 2-6 (a yield of 70%).

LC-MS: (ES, m/z): 417 [M–H]⁻.

7. Synthesis of Compound 2-7

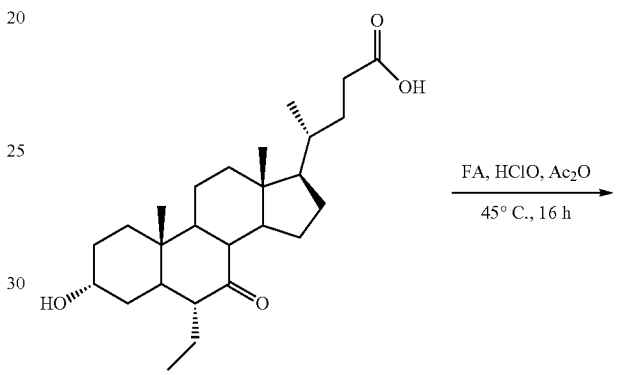

Compound 2-6 (215 g, 0.514 mol, 1.0 eq.) was dissolved in formic acid (2 L), and 15 mL of perchloric acid was added dropwise with stirring. The reaction was carried out at 45° C. for 16 hours. After the completion of the reaction, the reaction system was allowed to cool to room temperature. 1.5 L of acetic anhydride was added dropwise during 1.0 hour. After the completion of the addition, the solution was stirred well for 30 minutes. The mixture was poured into an ice bath, extracted twice with diethyl ether. The collected organic phase was washed with water, dried with anhydrous sodium sulfate, and concentrated to obtain yellow solid Compound 2-7, which was used directly in the next step of reaction without further purification.

LC-MS: (ES, m/z): 445 [M–H]⁻.

8. Synthesis of Compound 2-8

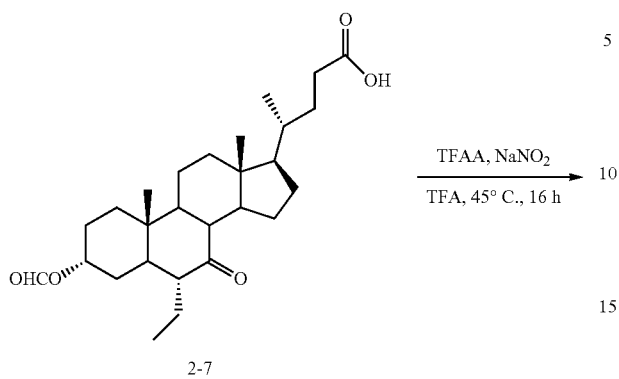

2-7

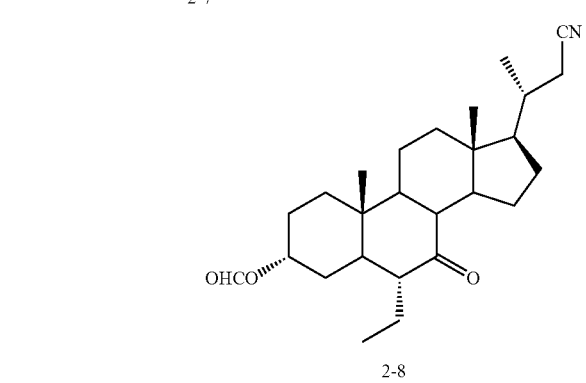

2-8

The crude product Compound 2-7 (220 g, 0.49 mol, 1.0 eq.) was dissolved in 1.5 L of trifluorineacetic acid, trifluorineacetic anhydride (425 mL, 3.67 mol, 7.5 eq.) was added with stirring. The reaction was carried out at 0 to 5° C. for 1.5 hours and then sodium nitrite (103 g, 1.48 mmol, 3.0 eq.) was added portionwise. After the completion of the addition, the reaction mixture was reacted at 0 to 5° C. for 1.5 hours, and then at 40° C. overnight. After the completion of the reaction, the reaction mixture was neutralized with a 2M sodium hydroxide aqueous solution, extracted twice with ethyl acetate. The collected organic phase was washed twice with a saturated aqueous solution of sodium chloride, dried with anhydrous sodium sulfate and concentrated to obtain 160 g of Compound 2-8, a yellow solid.

9. Synthesis of Compound 2-9

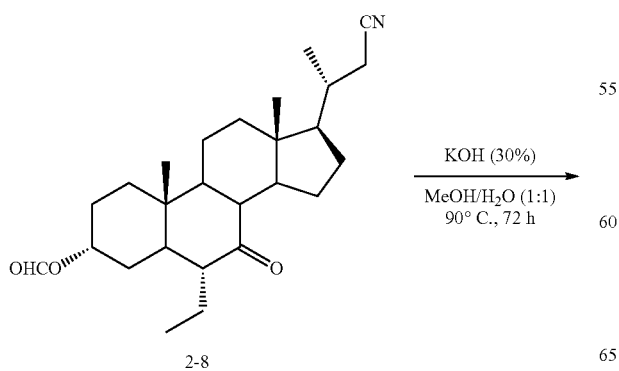

2-8

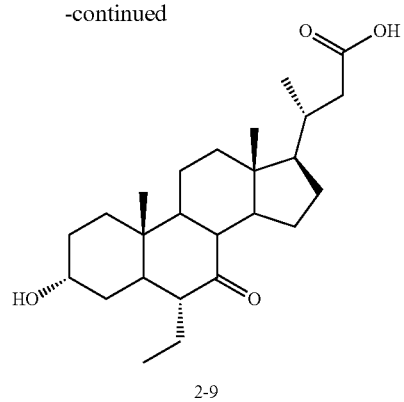

2-9

The crude product Compound 2-8 (160 g, 0.39 mol, 1.0 eq.) was dissolved in a solution of methanol:water=1:1, 40% aqueous solution of potassium hydroxide was added dropwise. After the completion of the addition, the reaction system was allowed to react at 90° C. for 72 hours. After the completion of the reaction, the reaction system was neutralized with a 6 N aqueous solution of hydrochloric acid. Methanol was removed by concentration under reduced pressure. The residue was extracted three times with ethyl acetate. The collected organic phase was washed with a saturated aqueous solution of sodium chloride, dried with anhydrous sodium sulfate and concentrated to obtain 150 g of off-white crude product of solid Compound 2-9, which was used directly in the next step of reaction without further purification.

LC-MS: (ES, m/z): 403 [M−H]⁻.

10. Synthesis of Compound 2-10

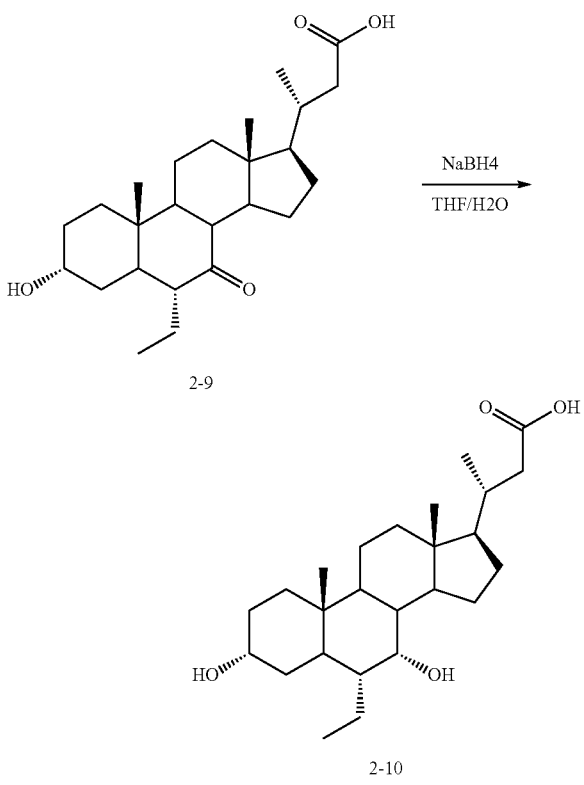

2-9

2-10

The crude product Compound 2-9 (150 g, 0.38 mol, 1.0 eq.) was dissolved in tetrahydrofuran/water (2.5 L, v/v=4/1). Sodium borohydride (72 g, 1.90 mol, 5.0 eq.) was added portionwise at 0° C. After the completion of the addition, the reaction system was allowed to react at room temperature for 2 hours. After the completion of the reaction, water and methanol was added at 0° C. to quench the reaction system. The solvent was concentrated, washed with water, acidified with 1N hydrochloric acid and extracted three times with ethyl acetate. The organic phase was collected, washed three times with a saturated aqueous solution of sodium chloride, dried with anhydrous sodium sulfate and concentrated to obtain 135 g of yellow solid crude product of Compound 2-10, which was used directly in the next step of reaction without further purification.

LC-MS: (ES, m/z): 405 [M−H]⁻.

11. Synthesis of Compound 2-11

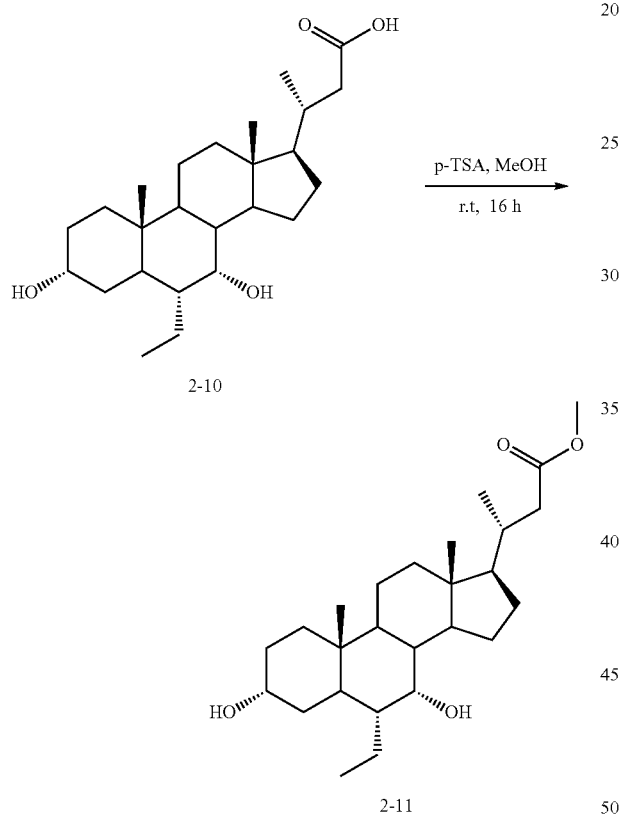

12. Synthesis of Compound 2-12

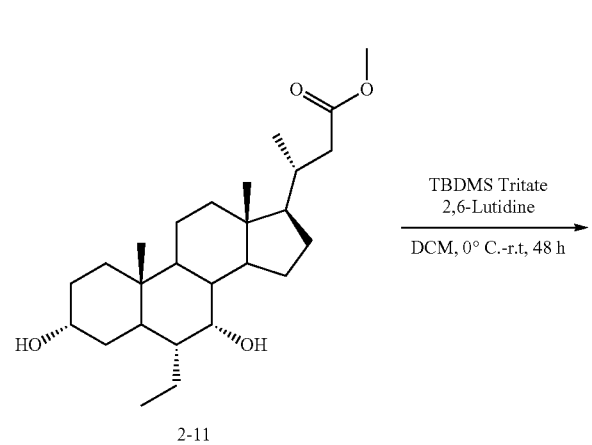

The crude product Compound 2-10 (135 g, 0.33 mol, 1.0 eq.) was added to dried methanol (2.5 L), and then p-toluenesulfonic acid (227 g, 1.32 mol, 4.0 eq.) was added. The reaction mixture was stirred well overnight. After the completion of the reaction, the reaction was neutralized with an aqueous solution of sodium bicarbonate. The solvent was concentrated. The residue was extracted twice with ethyl acetate. The organic phase was collected, washed with an aqueous solution of sodium bicarbonate and a saturated aqueous solution of sodium chloride, dried with anhydrous sodium sulfate and concentrated to obtain 120 g of yellow crude sticky product Compound 2-11, which was used directly in the next step of reaction without further purification.

LC-MS: (ES, m/z): 421 [M+H]⁺.

The crude product Compound 2-11 (120 g, 0.286 mol, 1.0 eq.) was dissolved in dichloromethane (2 L). 2,6-Lutidine (160 mL, 1.43 mol, 5.0 eq.) and trifluorinemethanesulfonic acid tert-butyldimethylsilyl ester (190 mL, 0.86 mol, 3.0 eq.) was added respectively at 0° C. The reaction system was stirred at room temperature for 24 hours. After the completion of the reaction, it was quenched with an aqueous solution of sodium bisulfate until neutral. The aqueous phase was separated and extracted twice with dichloromethane. The organic phase was washed with an aqueous solution of sodium bisulfate, a saturated aqueous solution of sodium carbonate and a saturated aqueous solution of sodium chloride, dried with anhydrous sodium sulfate and concentrated to obtain 135 g of yellow crude sticky product Compound 2-12.

13. Synthesis of Compound 2-13

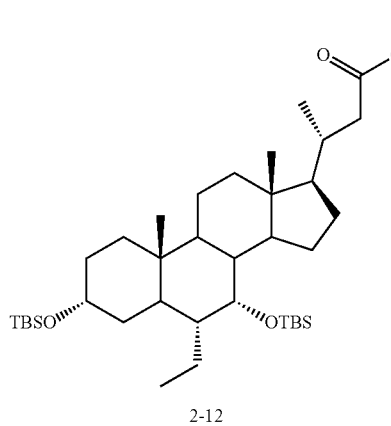

2-12

14. Synthesis of Compound 2-14

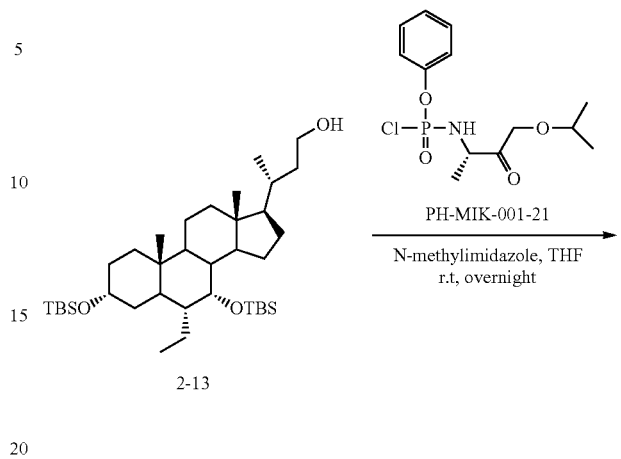

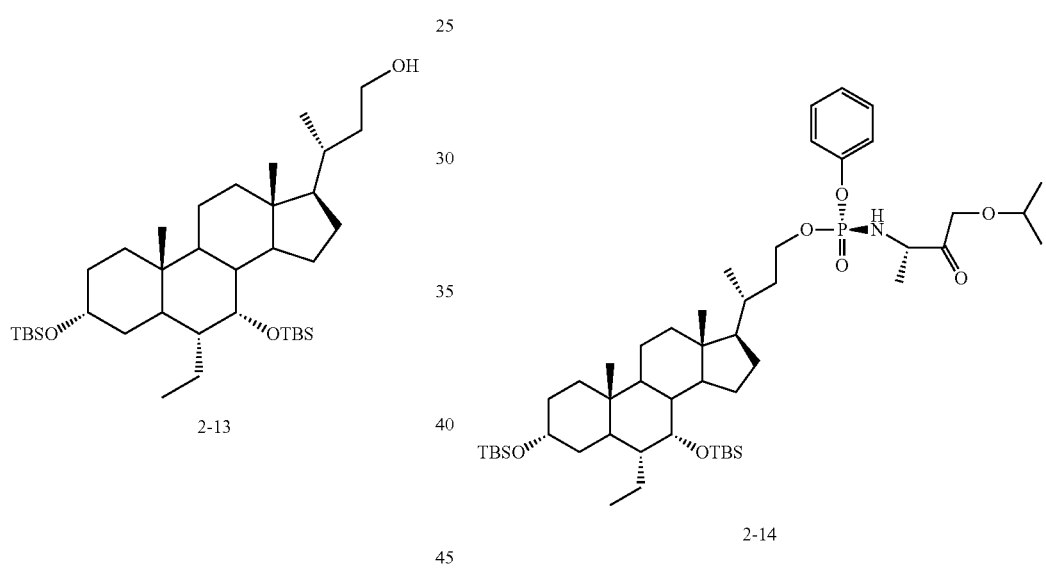

2-14

The crude product Compound 2-12 (135 g, 0.2 mol, 1.0 eq.) was dissolved in dried tetrahydrofuran (1.2 L), and dried methanol (24 mL) was added under protection of nitrogen at 0° C. Then lithium borohydride (290 mL, 2 M in THF, 0.6 mol, 3 eq.) was added portionwise. The mixed reagent was allowed to react at room temperature overnight. After the completion of the reaction, the reaction system was quenched with 1 M aqueous solution of sodium hydroxide and extracted three times with ethyl acetate. The organic phase was collected, washed with a saturated aqueous solution of sodium chloride, dried with anhydrous sodium sulfate and concentrated to obtain 120 g of yellow oily crude product Compound 2-13, which was used directly in the next step of reaction without further purification.

The crude product Compound 2-13 (120 g, 193 mmol, 1.0 eq.) and N-methylimidazole (126 g, 8.0 eq) were added to anhydrous tetrahydrofuran (1400 mL). The compound PH-MIK-001-21 (382.5 g, 6.5 eq) dissolved in anhydrous tetrahydrofuran was added dropwise with thorough stirring. After the completion of the addition, the reaction system was stirred at room temperature overnight. After the completion of the reaction, the solvent was removed by concentration under reduced pressure, purified with by silica gel column to obtain 80 g of yellow oily Compound 2-14.

16. Synthesis of Compound 2-0

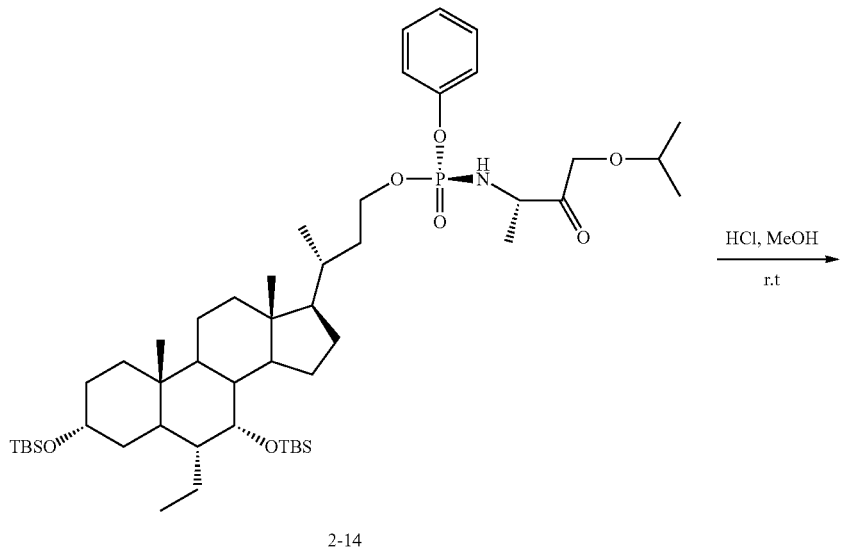

2-14

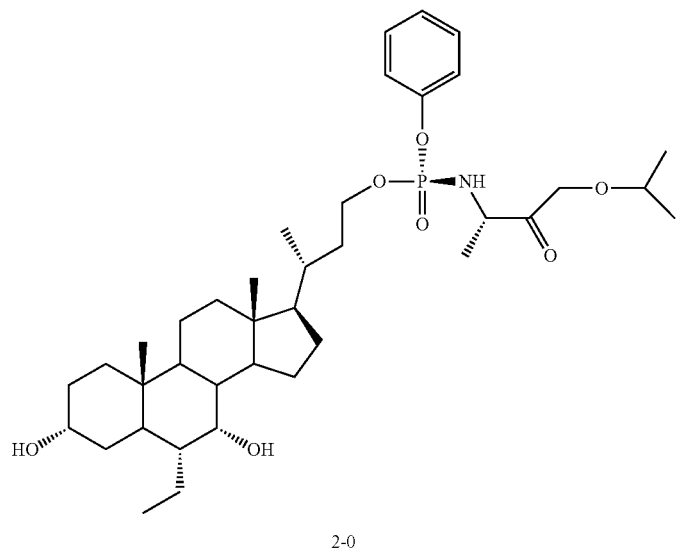

2-0

Compound 2-14 (80 g, 88 mmol, 1.0 eq.) was dissolved in dried methanol (1200 mL), and concentrated hydrochloric acid (242 mL, 2.9 mol, 20 eq.) was added dropwise to the above-mentioned reaction system. After the completion of the addition, the mixture was allowed to react at room temperature for 4 days. After the completion of the reaction, methanol was removed by concentration under reduced pressure. The remaining system was neutralized with water and sodium bicarbonate, extracted three times with dichloromethane. The organic phase was collected, washed with a saturated aqueous solution of sodium chloride, dried with anhydrous sodium sulfate and concentrated. The residue was purified by Flash-Prep-HPLC to obtain Compound 2-0, which is an off-white solid (a yield of 97.3%).

Example 3

1. Synthesis of Compound PH-MIK-001-22

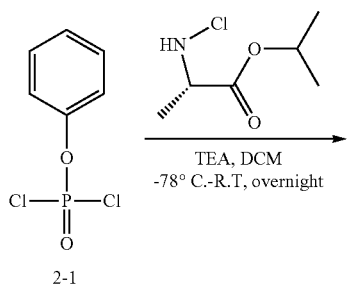

2-1

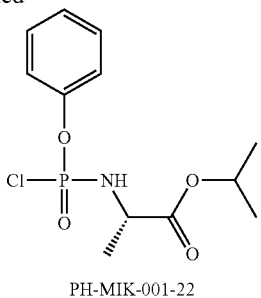

PH-MIK-001-22

20 L anhydrous dichloromethane was added into a three-neck flask, and then triethylamine (770 g, 2.0 eq.) was added. The reaction system was placed at −78° C., and a solution of Compound 2-1 (prepared according to the preparation method of Example 2, 800 g, 1.0 eq.) dissolved in anhydrous dichloromethane and (S)-3-(Chloroamino)-1-isopropoxybutan-2-one (631 g, 1.0 eq.) were added dropwise. After the completion of the reaction, the reaction was carried out for 2 hours. Then the reaction system was allowed to stand and warm back to room temperature for overnight. The solvent was removed. The residue was washed with ethyl acetate and then filtered. The filtrate was concentrated and dried to obtain Compound PH-MIK-001-22 (760 g), which was used directly in the next step of reaction.

2. Synthesis of Compound 3-1

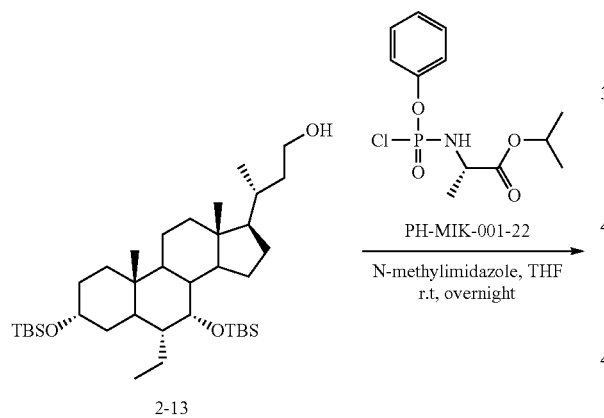

2-13

3-1

The crude product Compound 2-13 (120 g, 1.0 eq.) and N-methylimidazole (126 g, 8.0 eq.) were added to anhydrous tetrahydrofuran. A solution of compound PH-MIK-001-22 (401 g, 6.5 eq.) dissolved in anhydrous tetrahydrofuran was added dropwise with thorough stirring. After the completion of the addition, the reaction system was stirred at room temperature overnight. After the completion of the reaction, the solvent was removed by concentration under reduced pressure, purified with silica gel column to obtain 75 g of yellow oily Compound 3-1.

3. Synthesis of Compound 3-0

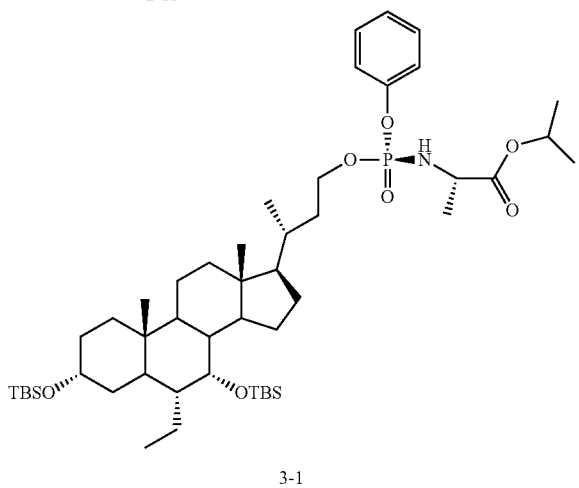

3-1

3-0

Compound 3-1 (75 g, 88 mmol, 1.0 eq.) was dissolved in dried methanol (1200 mL), concentrated hydrochloric acid (242 mL, 2.9 mol, 20 eq.) was added dropwise to the above-mentioned reaction system. After the completion of the dropwise addition, the solution was allowed to react at room temperature for 4 days. After the completion of the reaction, methanol was removed by concentration under reduced pressure. The remaining system was neutralized with water and sodium bicarbonate, and extracted three times with dichloromethane. The organic phase was collected, and washed with a saturated aqueous solution of sodium chloride, dried with anhydrous sodium sulfate and concentrated. The residue was purified by Flash-Prep-HPLC to obtain Compound 3-0, which was a 35 g off-white solid (a yield of 96.9%).

LC-MS: (ES, m/z): 662.21 [M+H]$^+$.

In addition to the compounds of which the preparation methods were specifically given, the compounds in Table 4 below were also prepared according to the preparation methods of Examples 1 to 3. Specific experimental steps were omitted, and the raw materials and reagents were all commercially available.

TABLE 4

| Compound numbers | Compound structures | LC-MS (m/z) [M + H]+ |
|---|---|---|
| Compound 1-IP | 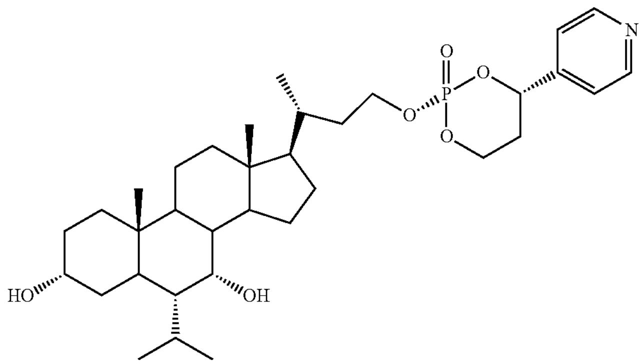 | 604.32 |
| Compound 1-Cl | 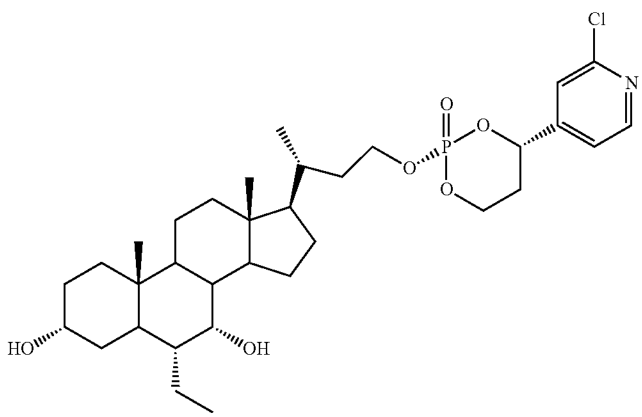 | 624.10 |
| Compound 1-Me1 | 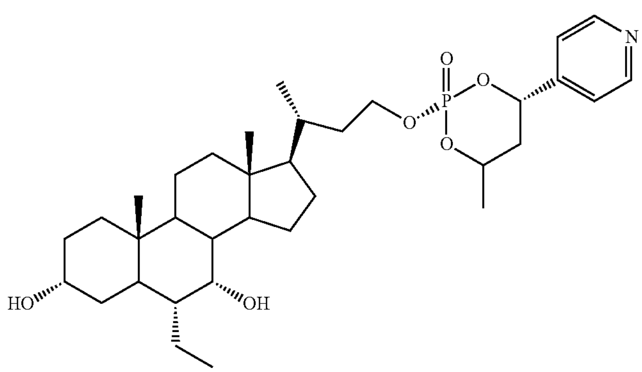 | 604.45 |
| Compound 1-F | 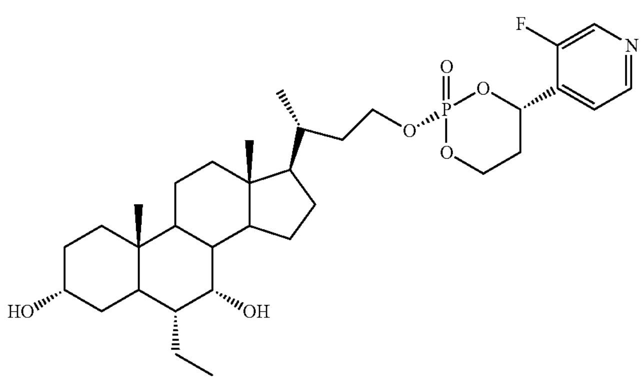 | 608.76 |

TABLE 4-continued

| Compound numbers | Compound structures | LC-MS (m/z) [M + H]+ |
| --- | --- | --- |
| Compound 1-Cl2 | 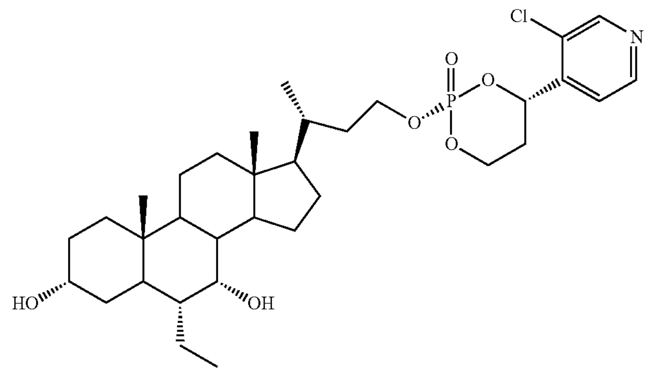 | 624.81 |
| Compound 1-Me2 | 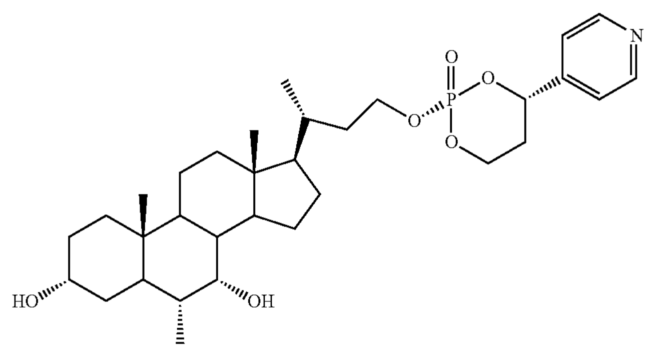 | 575.72 |
| Compound 1-Me3 | 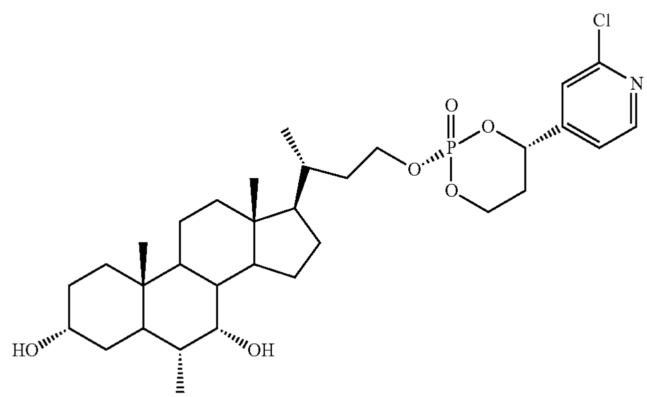 | 610.96 |
| Compound 4-0 | 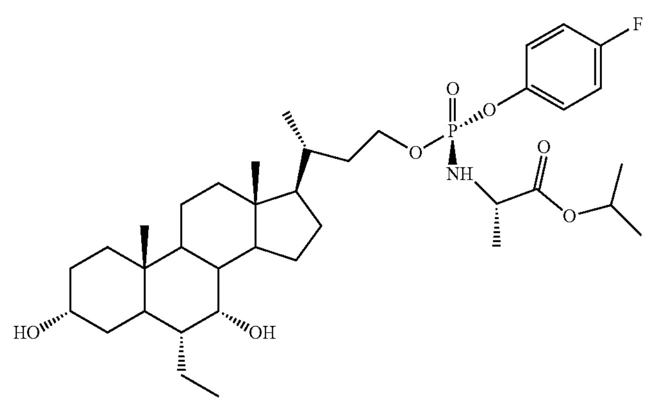 [SMILES: CC[C@@H]1C2C[C@H](O)CC[C@]2(C)C2CC[C@@]3(C)C(CC[C@@H]3[C@H](C)CCO[P@@](=O)(N[C@@H](C)C(=O)OC(C)C)Oc3ccc(F)cc3)C2[C@@H]1O] | 680.10 |

TABLE 4-continued
| Compound numbers | Compound structures | LC-MS (m/z) [M + H]+ |
|---|---|---|
| Compound 5-0 | 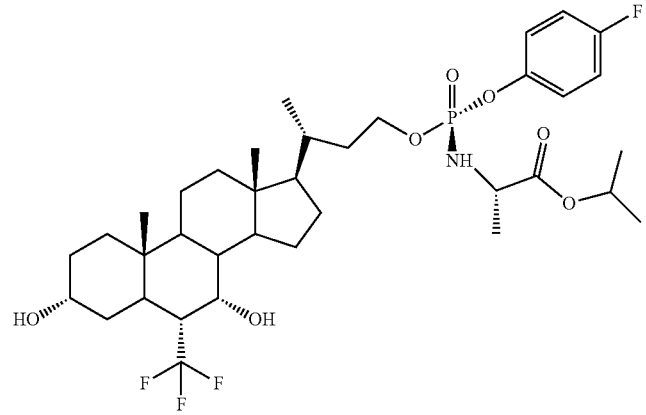 [SMILES: CC(C)OC(=O)[C@H](C)N[P@](=O)(OCC[C@@H](C)[C@H]1CCC2C3C(CC[C@@]21C)[C@@]1(C)CC[C@@H](O)CC1[C@@H](C(F)(F)F)[C@H]3O)Oc1ccc(F)cc1] | 720.94 |
| Compound 6-0 | 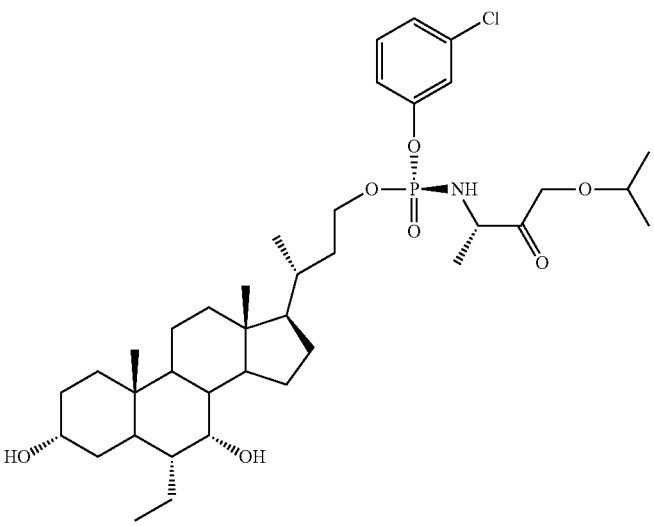 | 711.12 |
| Compound 7-0 | 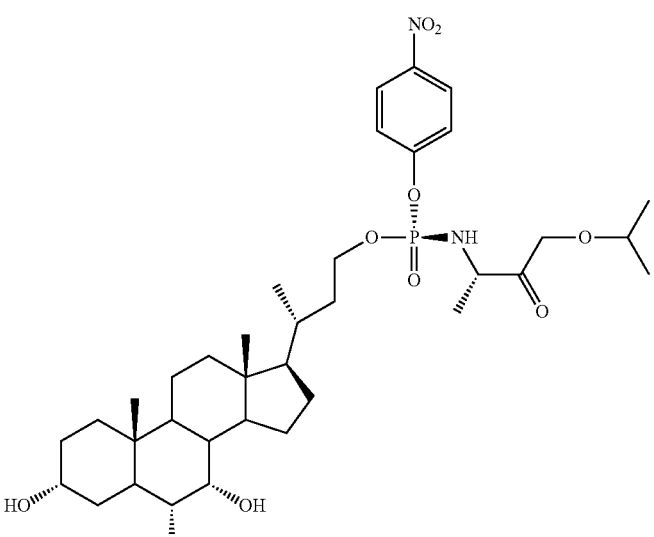 | 707.96 |

TABLE 4-continued

| Compound numbers | Compound structures | LC-MS (m/z) [M + H]+ |
|---|---|---|
| Compound 8-0 | *(structure)* | 697.45 |
| Compound 9-0 | *(structure)* | 762.20 |

Example 4 Application Example (A) the Effect of the Compounds of the Present Disclosure on 17α-Ethinylestradiol (E2-17α) Induced Cholestasis in Rats 1. Preparation of Test Solutions and Reagents Preparation of 1.0% CMC-Na solution: 1 p CMC-Na powder was weighed and added to 100 mL (50° C.) of distilled water, the mixture was rapidly stirred with a stirrer for 1 hour to fully swell, thereby to obtain a 1% CMC-Na solution.

Preparation of E2-17α solution in propylene glycol: 54/0.98=56 mp of E2-17α was weighed, dissolved in 9 mL of propane-1,2-diol, shaked by a vortexer for 1 hour, thereby to obtain a 7 mp/mL suspension of E2-17α.

2. Grouping and Administration Method

Sprague Dawley rats, weighing 250 to 350 g, were randomly grouped into: blank control group, E2-17α group (model group) and test compound groups, including E2-17α+Compound 1-H (5 mg/Kg) group, E2-17α+Compound 1-IP (5.1 mg/Kg) group, E2-17α+Compound 1-Cl (5.3 mg/Kg), E2-17α+Compound 1-Me 1 (5.1 mg/Kg) group, E2-17α+Compound 2-0 (5.1 mg/Kg) group, E2-17α+Compound 6-0 (5.9 mg/Kg) group, and positive control E2-17α+UDCA (15 mg/kg) group and obeticholic acid (OCA, 6 mg/kg+10 mg/kg) group. UDCA, i.e. ursodeoxycholic acid, is a bile acid derivative drug that has been marketed for the treatment of gallstones, cholestatic liver disease, fatty liver, and various types of hepatitis.

17α-Ethinylestradiol (E2-17α) was administered by subcutaneous injection into the neck for model establishment for 7 days. Meantime, the test compounds were suspended in a 1% CMC-Na solution and administered by intragastric administration for 7 days during the E2-17α modeling. The grouping is as shown in Table 5 below.

TABLE 5

Grouping and Administration Method

| Grouping | Numbers of Animals | Drugs | Administration Methods | Volumes of Administration |
|---|---|---|---|---|
| Control | 14 | Equal volume CMC-Na solution | s.c. + i.g. | 0.1 mL/100 g |
| E2-17α (7 mg/kg) | 14 | E2-17α (in propane-1,2-diol) + equal volume CMC-Na solution | s.c. | 0.1 mL/100 g |
| E2-17α + Compound 1-H (5 mg/kg) | 14 | E2-17α (in propane-1,2-diol) + Compound 1-H CMC-Na solution | s.c. + i.g. | 0.5 mL/100 g |
| E2-17α + Compound 1-IP (5.1 mg/kg) | 14 | E2-17α (in propane-1,2-diol) + Compound 1-IP-CMC-Na solution | s.c. + i.g. | 0.5 mL/100 g |
| E2-17α + Compound 1-Cl (5.3 mg/kg) | 14 | E2-17α (in propane-1,2-diol) + Compound 1-Cl-CMC-Na solution | s.c. + i.g. | 0.5 mL/100 g |
| E2-17α + Compound 1-Me1 (5.1 mg/kg) | 14 | E2-17α (in propane-1,2-diol) + Compound 1-Me1-CMC-Na solution | s.c. + i.g. | 0.5 mL/100 g |
| E2-17α + Compound 2-0 (5.6 mg/kg) | 14 | E2-17α (in propane-1,2-diol) + Compound 2-0-CMC-Na solution | s.c. + i.g. | 0.5 mL/100 g |
| E2-17α + Compound 6-0 (5.9 mg/Kg) | 14 | E2-17α (in propane-1,2-diol) + Compound 6-0-CMC-Na solution | s.c. + i.g. | 0.5 mL/100 g |
| E2-17α + UDCA (15 mg/kg) | 14 | E2-17α (in propane-1,2-diol) + UDCA pure aqueous solution | s.c. + i.g. | Calculated based on the actual drug dosage |
| E2-17α + OCA (10 mg/kg) | 14 | E2-17α (in propane-1,2-diol) + OCA-CMC-Na solution | s.c. + o.p. | Calculated based on the actual drug dosage |

(Note: s.c, subcutaneous injection; i.g, intragastric)

Note:
each administration group was given 17α-ethinylestradiol (E2-17α) at the same time.

3. Experimental Steps:

E2-17α in propylene glycol was administered to rats for 7 days to establish the model, and different test samples in CMC-Na solution were administered by intragastric administration. On the $8^{th}$ day, 1 mL of rat fasting blood sample was collected for detection of serum biochemical indicators, and E2-17α in propylene glycol was continuously administered to establish the model, and different test samples CMC-Na solution were administered by intragastric administration. After 0.5 hours of administration on the $9^{th}$ day, the rats were weighed and anesthetized with 10% urethane (10 mL/kg) via intraperitoneal injection. After anesthesia, the rat was fixed on a board. A midline abdominal incision was made from the upper acetabular area, and the incision was about 2 to 3 cm. The indoor temperature should be maintained during the experiment, the body temperature of the rats was maintained and bile outflow was promoted. Handle of ophthalmic forceps was used to turn the liver up and find the duodenum and stomach junction. A suture (size 0) was placed at the junction to reserve. On the duodenum, about 2 cm away from the pylorus, a thin tube with a yellow transparent tube perpendicular to the duodenum could be found passing through the pancreas, that is, the common bile duct. At the junction of the common bile duct and the duodenum, the common bile duct was separated by an ophthalmic curved forceps, but was careful not to break the small blood vessels around the bile duct and avoided stimulating the pancreatic tissue by hand. After the separation, two sutures were place, and the suture close to the intestine end was ligated, as a traction suture, ophthalmic scissors were used to obliquely cut a small opening in the wall of the tube, a prepared pancreatic juice collection tube was inserted into the small opening. A mixture of yellow bile and pancreatic juice flowed out immediately after the insertion. The tube was ligated and fixed, and this tube was used to collect bile. After completion of the intubation, the skin was sutured. The other end of the bile duct intubation was taken out, flowing out to a fixed 0.5 mL centrifuge tube. Bile was continuously collected 8 times once every 15 minutes, until 120 minutes.

4. Measurement of Indicators:

1) Collection of Bile

After completion of the intubation, the skin was sutured to prevent water evaporation of the abdominal cavity. The other end of the bile duct intubation was taken out, and the bile flowed out to a fixed 0.5 mL collection tube. Bile was continuously collected 8 times once every 15 minutes for a total of 120 minutes. Before the experiment, the collection tube was accurately weighed using an analytical balance. After the bile was collected in the experiment, the total weight of the bile and the collection tube was weighed, and the weight of the bile in the tube was calculated by subtraction and converted to a volume based on 1 g/mL. After collection of the bile, blood was taken from the inferior vena cava, and serum biochemical indicators were measured.

2) Detection of Indicators in Serum and Liver Samples

The blood sample was allowed to stand in a 37° C. water bath for 10 minutes, centrifuged at 3000 rpm (1368 g)×10 min, the serum was separated conventionally, dispensed and frozen at −20° C. for storage. The indicators to be detected in serum included ALT, AST, and ALP. The detection methods of the above indicators were all carried out in accordance with the relevant instructions of the kit.

5. Statistical Analysis

The data were analyzed using SPSS18.0 statistics software. Measurement data were compared between the two groups using the t test. Multiple groups of means were compared using one-way analysis of variance (ANOVA) and multiple comparisons between groups. Data mean±standard error (Mean±SEM.) or mean±standard deviation (Mean±SD.).

6. Test Results

The bile excretion rates at different time points in each rat group are shown in Table 6.

disclosure was still higher than that of the model group (the E2-17α group) 120 minutes after administration. The intensity of promoting bile excretion, i.e. amount of bile discharge, of the compounds of the present disclosure was better than those of obeticholic acid and ursodesoxycholic acid; the action time promoting bile excretion of the compounds of the present disclosure was also longer than those of obeticholic acid and ursodesoxycholic acid.

The serum ALT, AST, and ALP levels of each group of rats after intragastric administration are shown in Table 7.

TABLE 6

Bile discharge amount at different time points in different rat groups ($\bar{x} \pm s$, mg/kg/min)

| Time | Control (n = 12) | E2-17α (n = 11) | UDCA (n = 12) | Compound 1-H (n = 12) | Compound 1-IP (n = 12) | Compound 1-Cl (n = 11) | Compound 1-Mel (n = 11) | Compound 2-0 (n = 11) | Compound 6-0 (n = 11) | OCA (n = 11) |
|---|---|---|---|---|---|---|---|---|---|---|
| 15 min | 63.39 ± 16.75 | 49.85 ± 15.13 | 52.36 ± 13.30 | 62.24 ± 14.36 | 53.48 ± 13.30 | 57.80 ± 11.47 | 54.43 ± 12.13 | 52.89 ± 10.87 | 51.32 ± 9.43 | 51.23 ± 11.45 |
| 30 min | 60.51 ± 11.21 | 47.08 ± 10.53 | 47.70 ± 11.01 | 58.68 ± 12.90 | 51.73 ± 11.01 | 54.80 ± 12.37 | 48.85 ± 10.54 | 53.29 ± 8.76 | 52.04 ± 7.38 | 49.73 ± 10.22 |
| 45 min | 58.82 ± 10.62 | 44.81 ± 11.72 | 45.14 ± 10.63 | 55.89 ± 11.65 | 50.34 ± 10.63 | 48.17 ± 14.50 | 46.34 ± 14.76 | 47.13 ± 12.34 | 48.31 ± 11.45 | 47.97 ± 9.98 |
| 60 min | 55.56 ± 7.98 | 42.74 ± 10.55 | 44.58 ± 10.99 | 52.06 ± 10.46 | 47.63 ± 10.99 | 46.64 ± 11.80 | 45.74 ± 11.67 | 46.64 ± 11.78 | 45.96 ± 10.87 | 44.84 ± 6.6 |
| 75 min | 53.23 ± 9.84 | 42.02 ± 9.93 | 43.09 ± 10.63 | 51.47 ± 10.06 | 44.27 ± 10.63 | 45.83 ± 14.55 | 42.73 ± 13.42 | 45.06 ± 11.63 | 44.06 ± 12.75 | 43.77 ± 7.39 |
| 90 min | 50.76 ± 9.73 | 41.33 ± 12.68 | 40.08 ± 12.08 | 48.30 ± 11.81 | 43.56 ± 12.08 | 45.65 ± 15.01 | 42.12 ± 14.83 | 43.01 ± 15.25 | 43.11 ± 12.52 | 41.42 ± 8.05 |
| 105 min | 46.39 ± 10.82 | 39.85 ± 12.08 | 43.72 ± 11.41 | 45.36 ± 11.46 | 43.72 ± 11.41 | 43.37 ± 14.34 | 41.53 ± 12.28 | 43.26 ± 10.76 | 42.34 ± 11.63 | 38.56 ± 8.68 |
| 120 min | 45.70 ± 9.37 | 38.02 ± 10.54 | 41.11 ± 11.24 | 44.73 ± 13.20 | 42.36 ± 13.30 | 44.21 ± 16.91 | 40.25 ± 15.74 | 41.38 ± 10.58 | 40.21 ± 13.17 | 37.33 ± 9.62 |

Note:
17α-ethinylestradiol (E2-17α) was also administered to each of the above administration groups.

Figure 6:
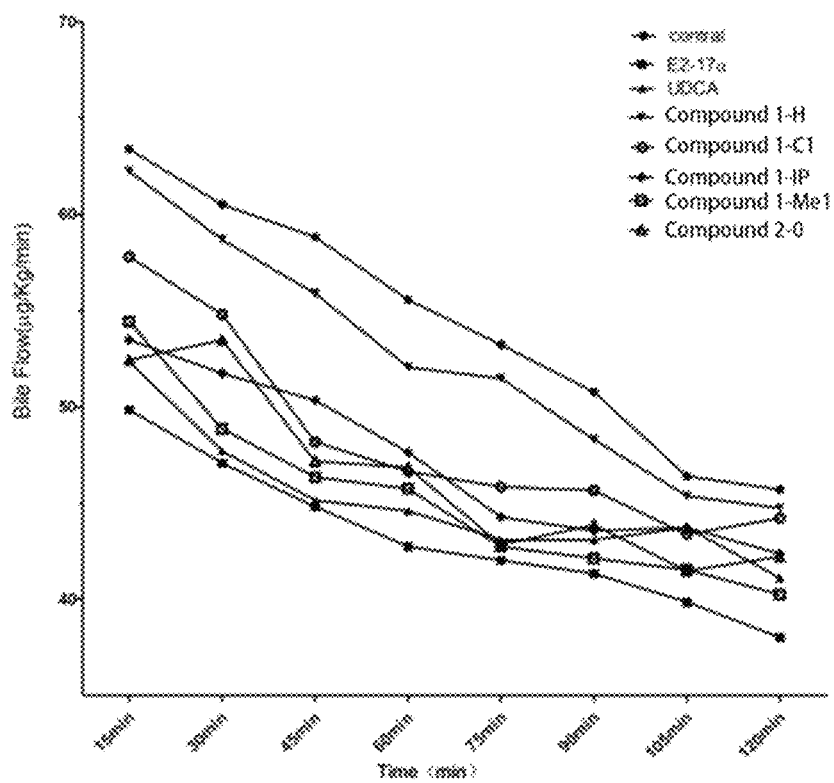
FIG. 6 is the bile discharge amount at different time points in different groups of rats.

Bile discharge amounts at different time points in rats in different dose groups of test Compound 1-H are compared in FIG. 6. As can be seen from Table 6 and FIG. 6, compared with the control group, the bile flow rate in the model group decreased; compared with the E2-17α group, the bile flow rate of the Compound 1-H, Compound 1-IP, Compound 1-Cl, Compound 1-Mel, Compound 2-0 and Compound 6-0 groups significantly increased (compared with E2-17α, *$P<0.05$).

According to the data in Table 6, comparing the effect of promoting bile excretion of the compounds in the present disclosure with the currently marketed ursodesoxycholic acid (UDCA): the bile discharge amounts of the test compounds of the present disclosure at a dose of 5 mg/kg to 5.6 mg/kg were equivalent to that of ursodesoxycholic acid at a dose of 15 mg/kg; 105 minutes after administration, the bile discharge amounts of the test Compound 1-H group and Compound 1-Cl group were significantly higher than that of the ursodeoxycholic acid group. Comparing the effect of promoting bile excretion of the compounds in the present disclosure with the currently marketed obeticholic acid (OCA): the bile discharge amounts of the test compounds of the present disclosure at a dose of 5 mg/kg to 5.6 mg/kg were higher than the bile discharge amounts of obeticholic acid at a dose of 10 mg/kg, and with the prolongation of the time after administration, the effect of promoting bile excretion of obeticholic acid gradually reduced, while the effect of promoting bile excretion of the compounds of the present

TABLE 7

Serum biochemical properties of rats in each group after intragastric administration (n = 12, $\bar{x} \pm s$)

| Grouping | n | ALT (U/L) | AST (U/L) | ALP (U/L) |
|---|---|---|---|---|
| Control | 12 | 64.17 ± 13.42 | 196.67 ± 11.14 | 191.75 ± 18.59 |
| E2-17α | 12 | 95.67 ± 10.03 | 280.58 ± 20.95 | 257.42 ± 18.22 |
| UDCA | 11 | 85.55 ± 13.80 | 263.36 ± 15.35 | 242.18 ± 12.10 |
| E2-17α + Compound 1-H | 11 | 72.36 ± 14.74 | 228.82 ± 17.74 | 218.64 ± 18.94 |
| E2-17α + Compound 1-IP | 12 | 87.42 ± 11.72 | 258.83 ± 10.82 | 230.92 ± 14.00 |
| E2-17α + Compound 1-Cl | 11 | 77.36 ± 11.42 | 230.89 ± 12.38 | 226.65 ± 12.38 |
| E2-17α + Compound 1-Mel | 12 | 80.64 ± 13.22 | 252.18 ± 16.59 | 235.64 ± 16.26 |
| E2-17α + Compound 2-0 | 12 | 78.64 ± 10.65 | 236.59 ± 13.06 | 220.35 ± 12.92 |

As can be seen from Table 7, Compound 1-H, Compound 1-IP, Compound 1-Cl, Compound 1-Mel, and Compound 2-0 could respectively lower the values of ALT, AST, and ALP.

7. Conclusion: Compound 1-H, Compound 1-IP, Compound 1-Cl, Compound 1-Mel, Compound 2-0 and Compound 6-0 in the examples of the present disclosure have a significant effect on ameliorating intrahepatic cholestasis, promoting bile excretion, and thus has a therapeutic effect on diseases associated with bile excretion disorders. The compounds in the examples of the present disclosure can also correspondingly reduce the levels of ALT, AST and ALP, indicating that the compounds in the examples of the present disclosure have certain effects on liver damage repair.

(B) The Effect of the Compound of the Present Disclosure on Cirrhotic Portal Hypertension

1. Preparation of Test Samples And Solutions

1) Preparation of saline solution of TAA: 10 g of thioacetamide (TAA) was weighed and dissolved in 100 mL of saline solution, and then filtered through a 0.22 μm sterile membrane filter into a sterile bottle.

2) Preparation of 0.5% CMC-Na suspension of test compound: 400 mg of Compound 1-H, Compound 1-IP, Compound 1-Cl, Compound 1-Mel or Compound 2-0 were weighed and dissolved in 100 mL of 0.5% CMC-Na solution, and shaken by a vortexer for 30 minutes, thereby to obtain 20 mg/Kg (high dose) groups. That is, CMC-Na suspension of 4 mg/mL of Compounds 1-H, 1-IP, 1-Cl, 1-Mel or 2-0. For the middle and low dose groups, drug preparation methods were the same.

2. Grouping and Administration Method

1) Modeling Method

A rat model of cirrhotic portal hypertension was established by intraperitoneal injection of TAA. Except that the blank control group was intraperitoneally injected with saline, remaining animals were intraperitoneally injected (i.p.) with 10% thioacetamide (TAA) in saline solution to establish the model. The dose was 200 mg/Kg, and the administration volume was 2 mL/Kg. All experimental animals were intraperitoneally injected with TAA or an equal volume of saline once every three days. Before each dose, the rat shaving beddings should be replaced by clean ones in advance. The body weight was measured once every two modeling administration. The body weight of the rats increased or decreased by 10% compared with the previous one, the dose of TAA increased or decreased by 50% correspondingly. The administration was individualized to strictly control body weight change of each rat, which could effectively improve the success rate and uniformity of modeling.

2) Animal Grouping

The successfully modeled animals were randomly grouped, 12 rats per group, and 20 rats in the blank control group. The groupings are shown in the table below. Portal hypertension was induced by TAA in rats, and a portal hypertension model was established after 13 days. The test compound was administered once a day for 10 days. The specific groupings are shown as follows:

TABLE 8

Experimental animal groups and administration doses

| Grouping | n | Administration Methods | Administration Doses (mg/Kg) | Volumes of Administration |
|---|---|---|---|---|
| Control | 20 | i.v. + i.g. | N.S. | — |
| TAA | 12 | i.v. + i.g. | N.S. | — |
| TAA + 1-H 5 mg/Kg | 12 | i.g. | 5 | 0.5 mL/100 g |
| TAA + 1-H 10 mg/Kg | 12 | i.g. | 10 | 0.5 mL/100 g |
| TAA + 1-H 20 mg/Kg | 12 | i.g. | 20 | 0.5 mL/100 g |
| TAA + 1-IP 5 mg/Kg | 12 | i.g. | 5 | 0.5 mL/100 g |
| TAA + 1-IP 10 mg/Kg | 12 | i.g. | 10 | 0.5 mL/100 g |
| TAA + 1-IP 20 mg/Kg | 12 | i.g. | 20 | 0.5 mL/100 g |
| TAA + 1-Cl 5 mg/Kg | 12 | i.g. | 5 | 0.5 mL/100 g |
| TAA + 1-Cl 10 mg/Kg | 12 | i.g. | 10 | 0.5 mL/100 g |
| TAA + 1-Cl 20 mg/Kg | 12 | i.g. | 20 | 0.5 mL/100 g |
| TAA + 1-Mel 5 mg/Kg | 12 | i.g. | 5 | 0.5 mL/100 g |
| TAA + 1-Mel 10 mg/Kg | 12 | i.g. | 10 | 0.5 mL/100 g |
| TAA + 1-Mel 20 mg/Kg | 12 | i.g. | 20 | 0.5 mL/100 g |
| TAA + 2-0 5 mg/Kg | 12 | i.g. | 5 | 0.5 mL/100 g |
| TAA + 2-0 10 mg/Kg | 12 | i.g. | 10 | 0.5 mL/100 g |
| TAA + 2-0 20 mg/Kg | 12 | i.g. | 20 | 0.5 mL/100 g |

(Note: i.v., intravenous; i.g., intragastric; N.S., saline)

3) Administration Method

Intragastric administration was adopted. Specific operation was the same as that of the intragastric operation in the examples of cholestasis.

3. Experimental Steps

Animal vital signs and behavioral activities, gastrointestinal reactions, etc. were observed daily during the test to observe the general state of the animal for abnormalities. The injection site was observed every day for signs of erythema, edema, hemorrhage or mass development. All animals were weighed once before administration, and the overall changes in rat constitution during modeling and administration were observed.

At the end of the administration, orbital blood was collected from the rats. The blood sample was placed in a 37° C. water bath for 10 minutes, centrifuged for 10 minutes at 3000 r/min (1370 g). Upper layer of the serum was taken and detected directly, or temporarily stored at −80° C., for serologic indicator measurement. After the blood samples were collected, the rats were fed with foods and water for 3 days. The blood volume was gradually restored for subsequent pressure measurement.

1) Measurement of Portal Vein Pressure

Rats were fasted for 12 hours before the experiment, and were anesthetized with 10% chloral hydrate via intraperitoneal injection. The dose of anesthetic was 2.5 mL/Kg. After the animal was anesthetized, it was immobilized on an operating table. The abdomen was opened about 3 cm along the abdominal white line. After laparotomy, the duodenum was flipped, the portal vein was found. No. 4 intravenous needle was used to connect to the pressure transformer. All the valves of the transformer were opened. The needle was inserted into the portal vein, after blood flowing back, continued to insert about 1cm. After the pressure was stable, all valves were closed. Stable portal vein pressure was measured. The pressure transformer was connected to a biological function test system (BL-420F).

2) Mean Arterial Pressure Measurement.

The skin along the midline was incised using scissors. One side of the common carotid artery was separated. The common carotid artery was cannulated to measure the mean arterial pressure. The measurement method was the same as that of the portal vein.

4. Indicator Detection 1) 1.5 mL of orbital blood was collected before the experiment, of which the steps were the same as the aforesaid steps, to measure serum ALT, AST, ALP, γ-GT and TBA contents.

2) A small piece at same part of the liver of the rat was cut and fixed in a 10% formaldehyde solution for tissue section pathology observation. An appropriate size of the liver was cut off, and the blood on the surface was washed off quickly with saline, put into a sterile EP tube, cryopreserved in liquid nitrogen for subsequent experiments.

5. Test Results

1) Portal vein pressure: Compared with the blank control group, the portal vein pressure in the TAA group (model group) increased ($\nabla P<0.01$), indicating that cirrhotic portal hypertension had occurred; compared with the TAA group, the portal vein pressure in the 5 mg/Kg group, the 10 mg/Kg group, and the 20 mg/Kg group of each test compound significantly decreased (#$P<0.05$, $\Delta P<0.01$).

Figure 7:
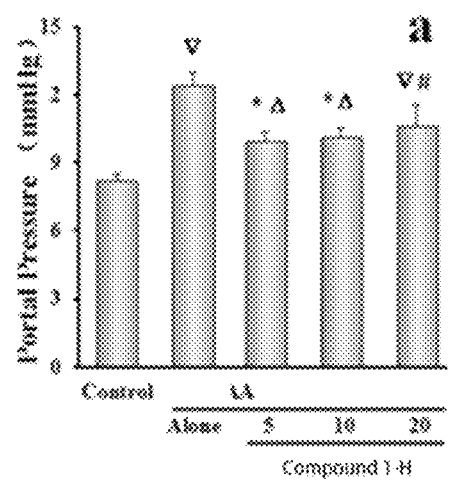
FIG. 7 is the effect on portal vein pressure in rats of each dose group of tested Compound 1-H.

FIG. 7 shows the effect of each dose group of test compound 1-H on portal vein pressure.

Figure 8:
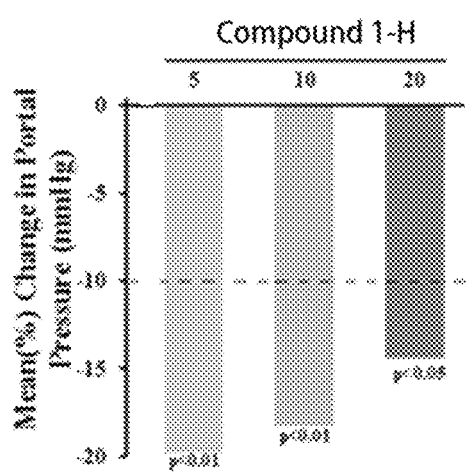
FIG. 8 is the average percentage change of portal vein pressure in rats of each dose group of tested Compound 1-H.

Percentage difference from the mean value of portal vein pressure of the TAA group, the mean percentage change (%) of each component of the administration group was obtained. Wherein, the percentage of portal vein pressure reduction was >10%, which can be considered clinically meaningful and related to the risk of portal hypertension. As can been seen from the figure, treated by administering Compound 1-H, the mean percentage changes of portal vein pressure of TAA+Compound 1-H 5 mg/Kg group, TAA+Compound 1-H 10 mg/Kg group, TAA+Compound 1-H 20 mg/Kg group were all greater than 10%. Therefore, it can be considered that using the Compound 1-H to reduce portal hypertension is clinically meaningful ($P<0.01$, $P<0.05$). FIG. 8 shows the mean percentage changes of portal vein pressure in rats in each dose group of test compound 1-H.

Figure 9:
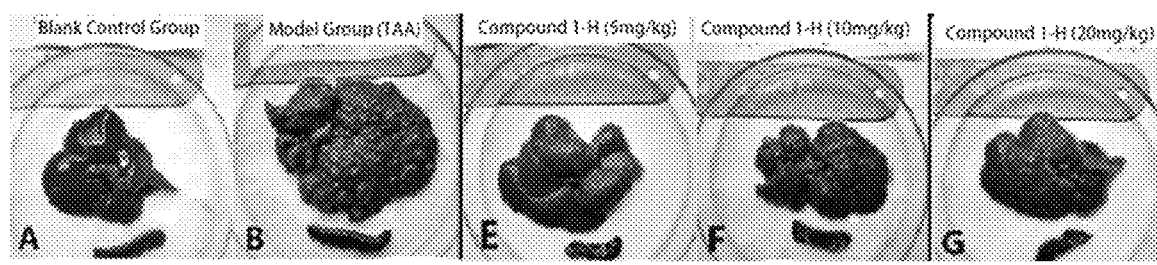
FIG. 9 is the appearance of liver and spleen of rats in each dose group of tested Compound 1-H.

2) Appearance of the liver: The appearance of the liver and spleen of rats in each dose group of test Compound 1-H is shown in FIG. 9. FIG. 9 (A) shows the control (blank control) group. The liver of the rats in the blank control group was bright red, the surface was smooth and shiny, the boundary was clear, and the size and liver wet weight were normal. FIG. 9 (B) shows the TAA (model) group. The liver of the rats in the TAA group was reddish-brown, the boundary was unclear, and the liver surface was coarse and heterogeneous. Nodular hyperplasia formed more spherical protrusions on some rat liver surface. Hepatic lobe size of some rats with cirrhosis was abnormal, and the main manifestations were: left lateral segment, central hepatic segments and two discoid papillary segments increased in volume, while left middle segment and caudate lobe showed different degree of atrophy, but the overall volume increased and the wet weight increased; the size of the spleen of most rats was normal or slightly atrophic. FIG. 9 (E) shows the TAA+5 mg/Kg Compound 1-H group. After administration of compound 1-H, compared with the TAA group, the liver cirrhosis nodules of rats in the TAA+5 mg/Kg Compound 1-H group was milder, the bulge significantly reduced, the atrophy or hyperplasia changes of the liver lobe was lighter, but the surface was still heterogeneous compared with the blank control group. FIG. 9 (F) shows the TAA+10 mg/Kg Compound 1-H, and FIG. 9 (G) shows the TAA+20 mg/Kg Compound 1-H group, the liver and spleen appearance was similar to that of the TAA+5 mg/Kg Compound 1-H group.

Figure 10:
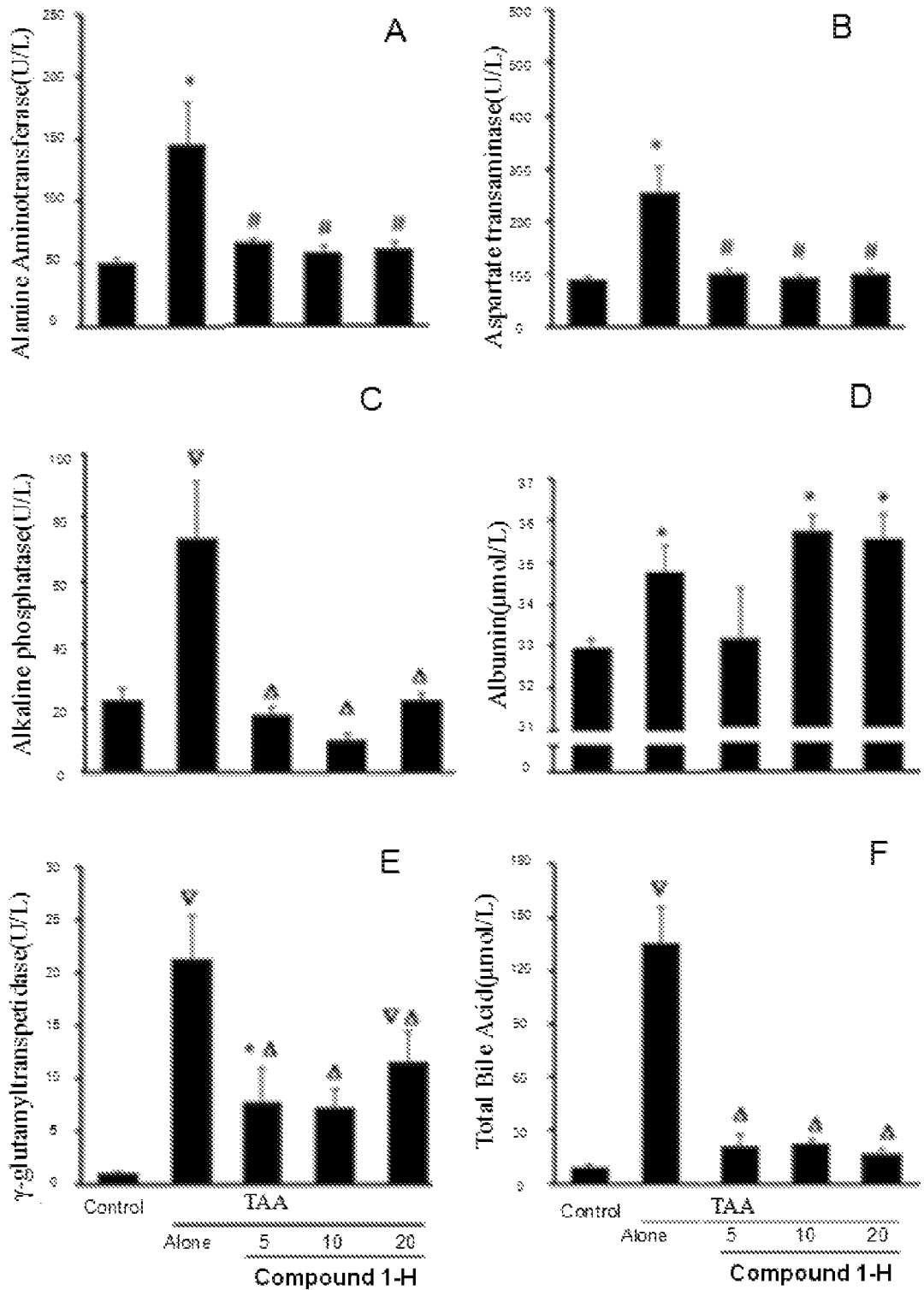
FIG. 10 is serologic indicators of rats in each dose group of test compound 1-H.

3) Blood biochemical indicators: Serum indicators of rats in each dose group of test compound 1-H are shown in Figure. 10. FIG. 10 (A) shows the serum ALT levels of rats in each group (Mean±SEM, n=12). Compared with the blank control group, ALT level in the TAA group increased (*$P<0.05$); ALT levels of the Compound 1-H 5 mg/Kg group, Compound 1-H 10 mg/Kg group, and Compound 1-20 mg/Kg group decreased (#$P<0.05$). FIG. 10 (B) shows serum AST levels (Mean±SEM, n=12) of rats in each group. Compared with the blank control group, AST level of the TAA group increased (*$P<0.05$); AST levels of the Compound 1-H 5 mg/Kg group, Compound 1-H 10 mg/Kg group, and Compound 1-H 20 mg/Kg group decreased (#$P<0.05$). FIG. 10 (C) shows serum ALP levels (Mean±SEM, n=12) of rats in each group. Compared with the blank control group, ALP level of the TAA group increased ($\nabla P<0.01$); ALT levels in all administration groups decreased (#$P<0.05$, $\Delta P<0.01$). FIG. 10 (D) is serum ALB contents (Mean±SEM, n=12) of rats in each group. FIG. 10 (E) shows serum γ-GT levels (Mean±SEM, n=12) of rats in each group. Compared with the blank control group, γ-GT level of the TAA group increased ($\nabla P<0.01$), γ-GT levels in all administration groups decreased (#$P<0.05$, $\Delta P<0.01$). FIG. 10 (F) shows serum TBA contents (Mean±SEM, n=12) of rats in each group. Compared with the blank control group, TBA level in the TAA group increased ($\nabla P<0.01$), TBA levels in all administration groups decreased ($\Delta P<0.01$).

Figure 11:
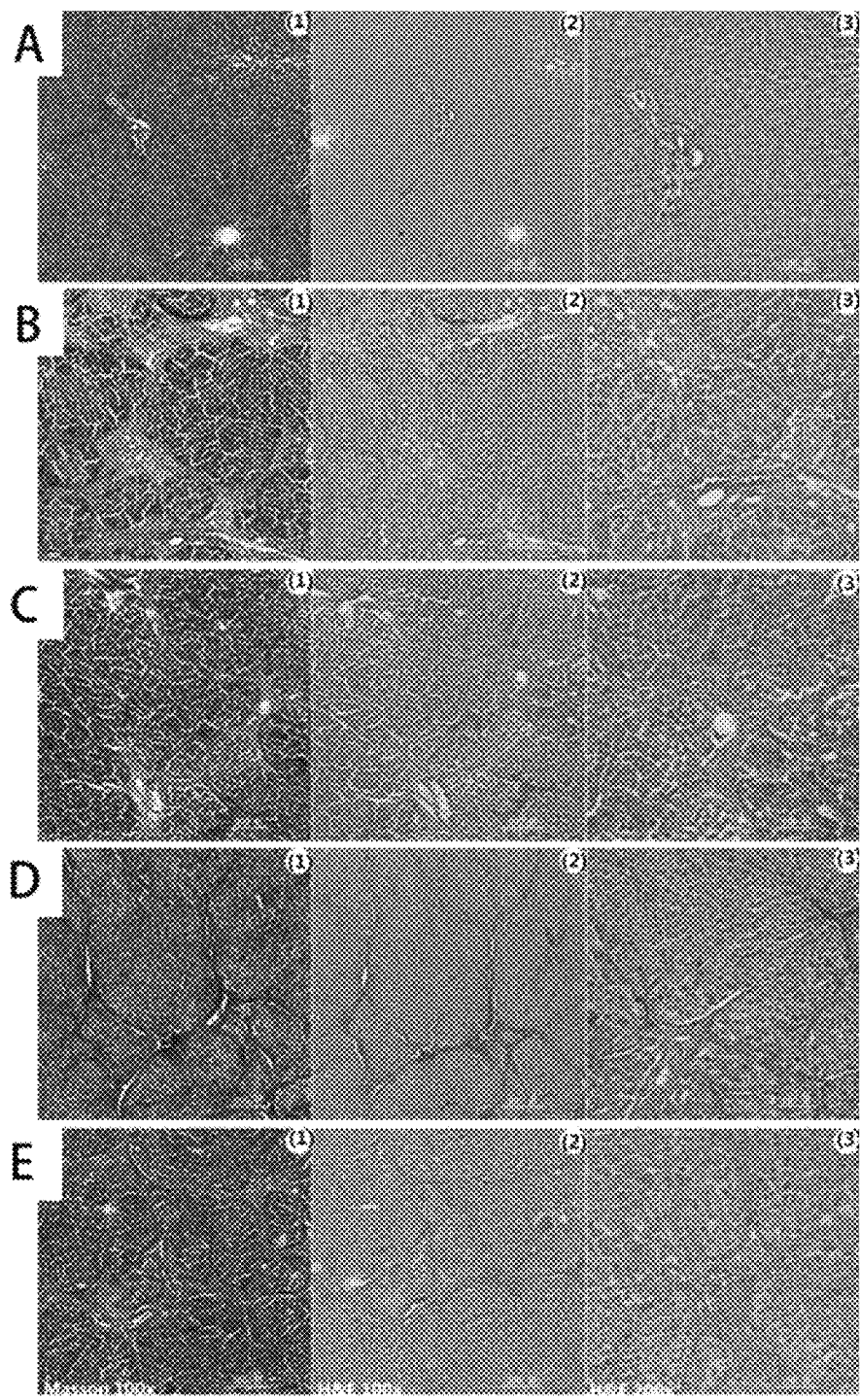
FIG. 11 is Masson's trichrome stain and HE stain of liver pathological sections of rats in each dose group of tested Compound 1-H.

4) Liver tissue section: The Masson staining and HE staining images of liver pathological sections of rats in each dose group of test compound 1-H are shown in FIG. 11. FIGS. (1) to (3) are respectively Masson stained (100× field of view), HE stained (100× field of view) and HE stained (200× field of view) of the same sample. Wherein FIG. 11(A) is microscopic photographs of the control (blank control) group. In the blank control group, there was no obvious hyperplasia of liver fibrous tissue, the morphology of the portal tube area was normal, and there was no hyperplasia of the bile duct. The morphological structure of hepatocytes was normal, and no cell necrosis or inflammatory cell infiltration was observed. FIG. 11 (B) is microscopic photographs of the TAA (model) group. Compared with the blank control group, the fibrous tissue of the TAA group was hyperplastic and formed pseudolobules, there was hyperplasia of the bile ducts in the portal tube area accompanied by round lymphocytic infiltration, and symptoms of liver fibrosis were developed. FIG. 11 (C) is microscopic photographs of the TAA+5 mg/Kg Compound 1-H group. The group mainly showed that the interstitial space of the fibrous tissue was thinner, the cell morphologic structure was basically normal, the inflammatory cell infiltration was milder, and there was no lots of hyperplasia of the bile duct in the portal tube area, which proved that the symptoms of liver fibrosis were ameliorated. FIG. 11 (D) is microscopic photographs of the TAA+10 mg/Kg Compound 1-H group. The morphopathologic structure of the group was similar to that of the TAA+5 mg/Kg Compound 1-H group. FIG. 11 (E) is microscopic photographs of the TAA+20 mg/Kg Compound 1-H group. The morphopathologic structure of the group was similar to that of the TAA+5 mg/Kg Compound 1-H group. Pathological indicators shows that compound 1-H had certain improvement effects on the hyperplasia of liver fibrous tissue and pseudolobule formation, which was mainly characterized by thinning of fibrous septa.

6. Conclusion

Rat cirrhotic portal hypertension was successfully induced by intraperitoneal injection of TAA, and the test compounds prepared in the examples of the present disclosure were administered after the model was established. The experimental results show that using 5 mg/Kg, 10 mg/Kg and 20 mg/Kg three doses of the test compounds can (1) reduce the portal vein pressure in rats, the percentage of portal vein pressure reduction was >10%; (2) improve liver cirrhosis nodular hyperplasia, lobar atrophy or hyperplasia of the liver; (3) improve the levels of various blood indicators in rats, ALT, AST, ALP, ALB, γ-GT and TBA all decreased; (4) improve tissue morphology, alleviate liver fibrosis lesions.

The above-mentioned results can be explained by that the test compounds of the present disclosure improves the intrahepatic high blood flow resistance in the function of relieving hepatic vasoconstriction by activating the FXR and TGR5 receptors, and at the same time has certain effects on ameliorating organic lesions such as liver fibrosis, and promoting the decrease of blood flow resistance in the liver. In addition, due to its own effect of increasing bile secretion and discharge, serum TBA, ALP and γ-GT levels decrease, reducing further damage to liver cells by toxic substances after cholestatic, and reducing levels of ALT and AST.

In summary, the compounds of the present disclosure can better reduce rat cirrhotic portal hypertension, and also has certain effects on ameliorating organic lesions such as liver fibrosis.

The above description of the examples is merely to assist in understanding the method and its core idea of the present invention. It should be pointed out that a person having ordinary skill in the art can make various modifications and changes to the present invention without departing from the spirit and scope of the invention, and these modifications and changes also fall in the protection scope of the present invention.

What is claimed is:

1. A compound as shown in Formula (I), or a racemate, a stereoisomer, a geometric isomer, a tautomer, or a pharmaceutically acceptable salt thereof:

wherein, $R_1$ is hydrogen, substituted or unsubstituted alkyl or halogen;

each of the $R_2$ is independently selected from the group consisting of substituted or unsubstituted alkyl, halogen, hydroxyl, nitro, cyano, sulphonic acid group and carboxyl;

m is 0, 1, 2, 3 or 4;

each of the $R_3$ is independently selected from the group consisting of substituted or unsubstituted alkyl, halogen, hydroxyl and aryl; and n is 0, 1, 2, 3 or 4.

2. The compound according to claim 1, wherein $R_1$ is hydrogen, substituted or unsubstituted $C_{1-5}$ alkyl or halogen.

3. The compound according to claim 1, wherein $R_1$ is hydrogen, fluorine, chlorine, bromine, substituted or unsubstituted methyl, substituted or unsubstituted ethyl, substituted or unsubstituted propyl, or substituted or unsubstituted isopropyl.

4. The compound according to claim 1, wherein each of the $R_2$ is independently selected from the group consisting of fluorine, chlorine, bromine, nitro, substituted or unsubstituted methyl, substituted or unsubstituted ethyl, and substituted or unsubstituted isopropyl;

m is 0 or 1;

each of the $R_3$ is independently selected from the group consisting of fluorine, chlorine, bromine, substituted or unsubstituted methyl, and substituted or unsubstituted ethyl; and n is 0 or 1.

5. The compound according to claim 1, which is selected from the group consisting of:

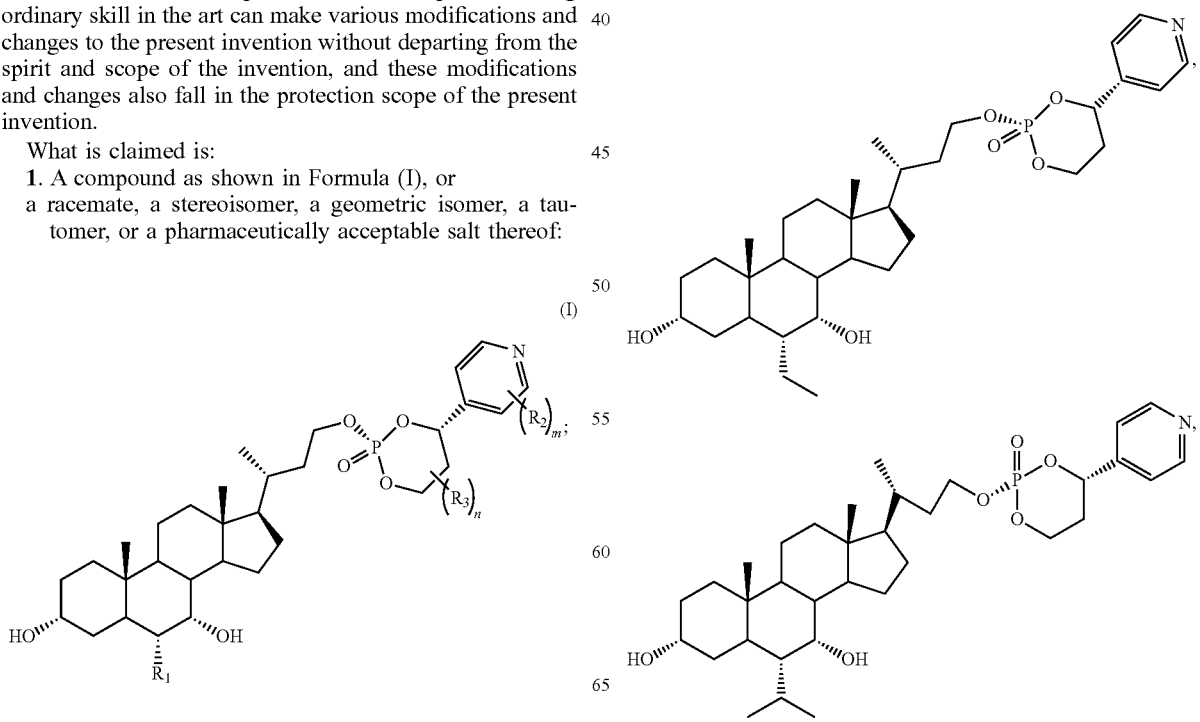

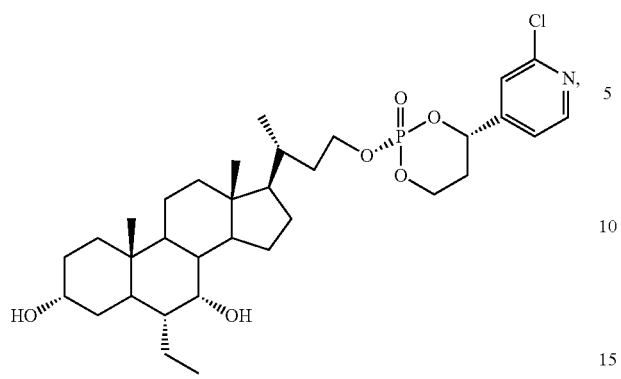
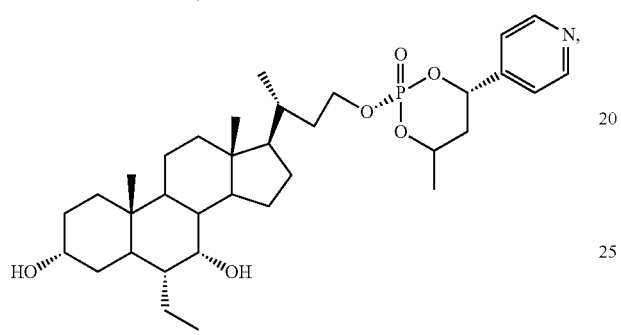
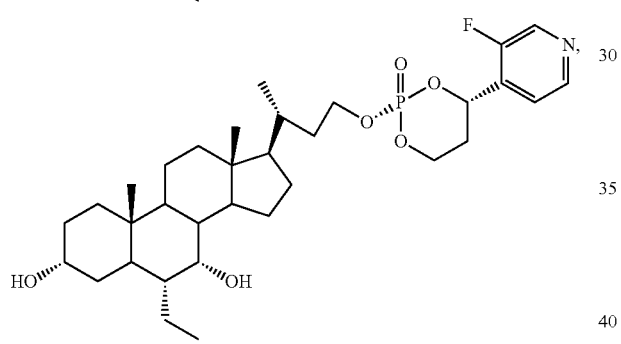
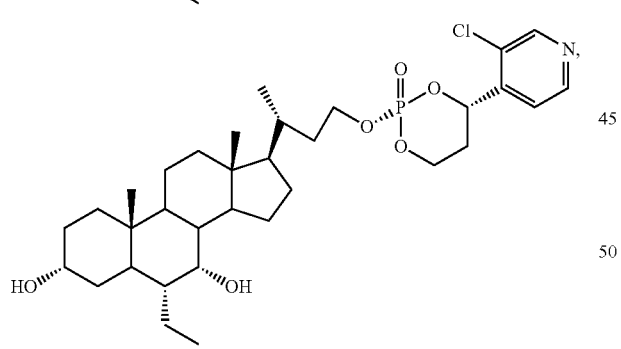
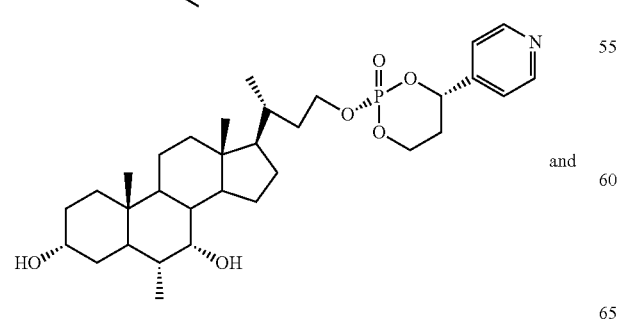
and
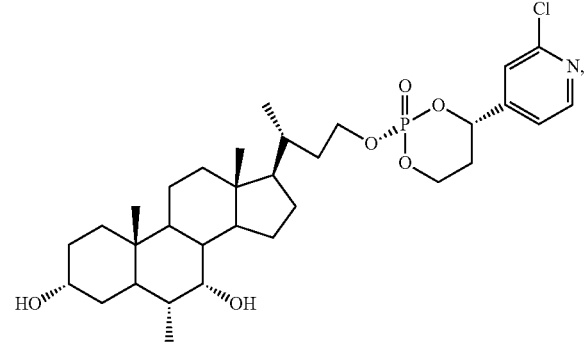
or a stereoisomer, a tautomer, or a pharmaceutically acceptable salt thereof.
6. A method of producing the compound according to claim 1, comprising:
reacting Compound (10) with Compound (16) to obtain a compound as shown in Formula (I),
(10)
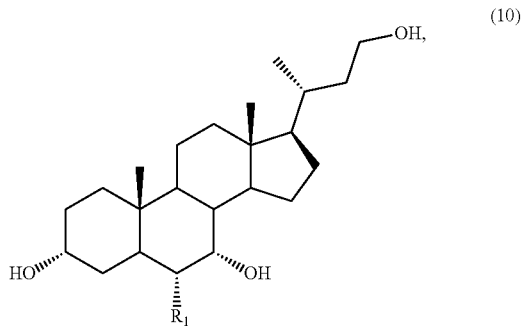
(16)
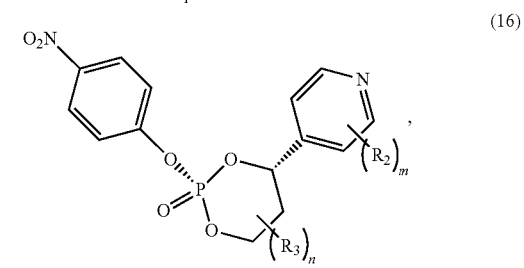
(I)
wherein,
$R_1$ is hydrogen, substituted or unsubstituted alkyl, and halogen;

each of the $R_2$ is independently selected from the group consisting of substituted or unsubstituted alkyl, halogen, hydroxyl, nitro, sulfonyl hydroxide and carboxyl;

m is 0, 1, 2, 3 or 4;

each of the $R_3$ is independently selected from the group consisting of substituted or unsubstituted alkyl, halogen, hydroxyl and aryl; and n is 0, 1, 2, 3 or 4.

7. The method according to claim 6, wherein the reaction is performed under the catalysis of tert-butylmagnesium chloride and with 1,4-dioxane as the solvent.

8. A method for activating receptor FXR and/or TGR5 comprising administering to a subject or sample in need thereof a therapeutically effective amount of the compound according to claim 1.

9. A method for treating or ameliorating receptor FXR and/or TGR5 mediated disease, comprising administering to a subject in need thereof a therapeutically effective amount of the compound according to claim 1.

10. The method according to claim 9, wherein the receptor FXR and/or TGR5 mediated disease is selected from chronic liver disease, metabolic disease and portal hypertension.

11. The method according to claim 10, wherein the chronic liver disease is selected from primary biliary cholestatic cirrhosis, primary sclerosing cholangitis, liver fibrosis-related disease, drug-induced cholestasis, progressive familial intrahepatic cholestasis, cholestasis of pregnancy, alcoholic liver disease and non-alcoholic fatty liver disease; the portal hypertension is a portal hypertension with increased portal pressure caused by liver fibrosis, cirrhosis, splenomegaly or another reason; and the metabolic disease is selected from hypercholesterolemia, dyslipidemia, cholesterol gallstones and hypertriglyceridemia.

12. A compound as shown in Formula (II), or a racemate, a stereoisomer, a geometric isomer, a tautomer, or a pharmaceutically acceptable salt thereof:

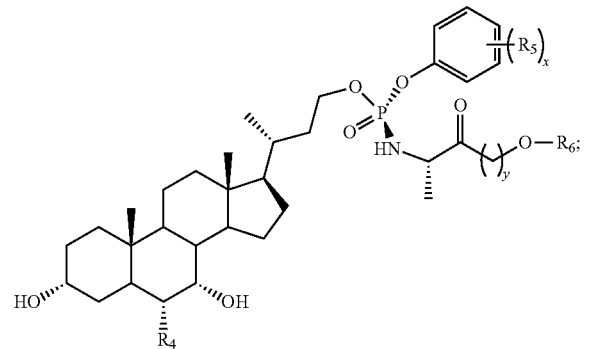

(II)

wherein, $R_4$ is hydrogen, substituted or unsubstituted alkyl or halogen;

each of the $R_5$ is independently selected from the group consisting of substituted or unsubstituted alkyl, halogen, hydroxyl, cyano, nitro, sulphonic acid group, and carboxyl;

$R_6$ is selected from the group consisting of substituted or unsubstituted $C_{1-5}$ alkyl, aryl, heteroaryl, and cyclohexyl;

x is 0, 1, 2, 3 or 4; and y is 0 or 1.

13. The compound according to claim 12, wherein $R_4$ is hydrogen, substituted or unsubstituted $C_{1-6}$ alkyl or halogen.

14. The compound according to claim 12, wherein $R_4$ is hydrogen, fluorine, chlorine, bromine, substituted or unsubstituted methyl, substituted or unsubstituted ethyl, substituted or unsubstituted propyl or substituted or unsubstituted isopropyl;

each of the $R_5$ is independently selected from the group consisting of hydrogen, fluorine, chlorine, bromine, hydroxyl, cyano, substituted or unsubstituted methyl, substituted or unsubstituted ethyl, and substituted or unsubstituted isopropyl; and $R_6$ is selected from the group consisting of substituted or unsubstituted methyl, substituted or unsubstituted ethyl, substituted or unsubstituted propyl, substituted or unsubstituted isopropyl, phenyl, pyridyl and cyclohexyl.

15. The compound according to claim 12, which is selected from the group consisting of:

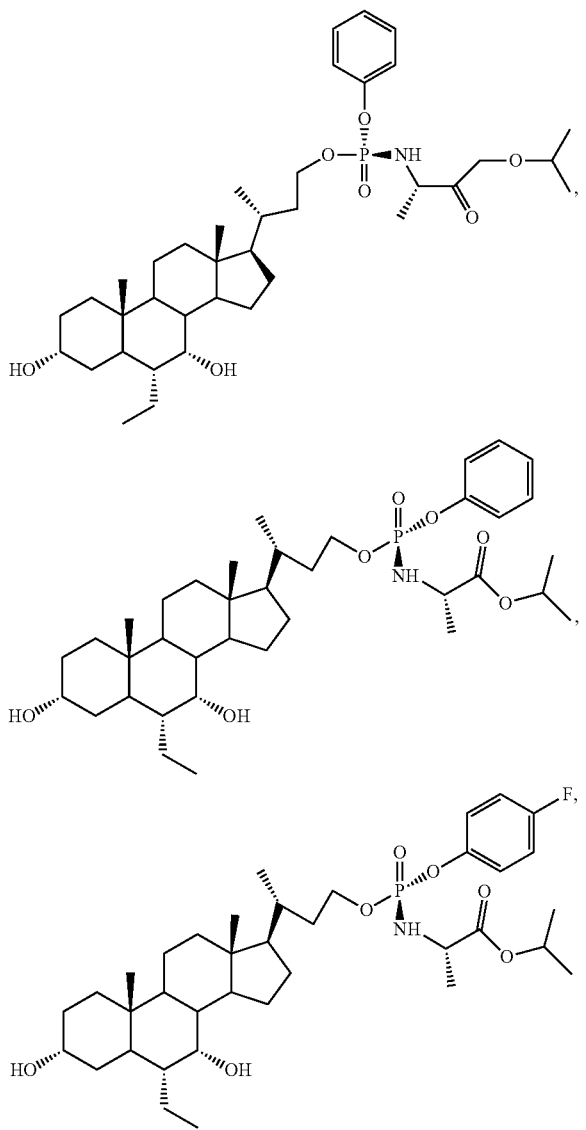

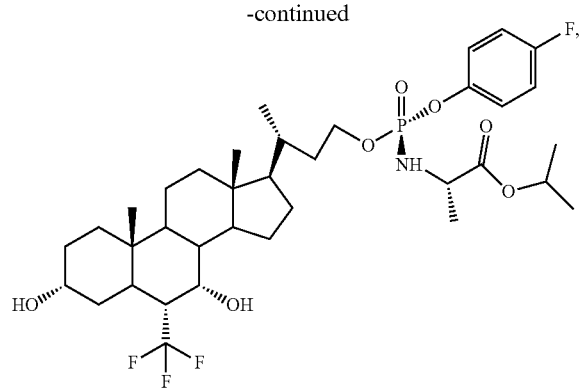
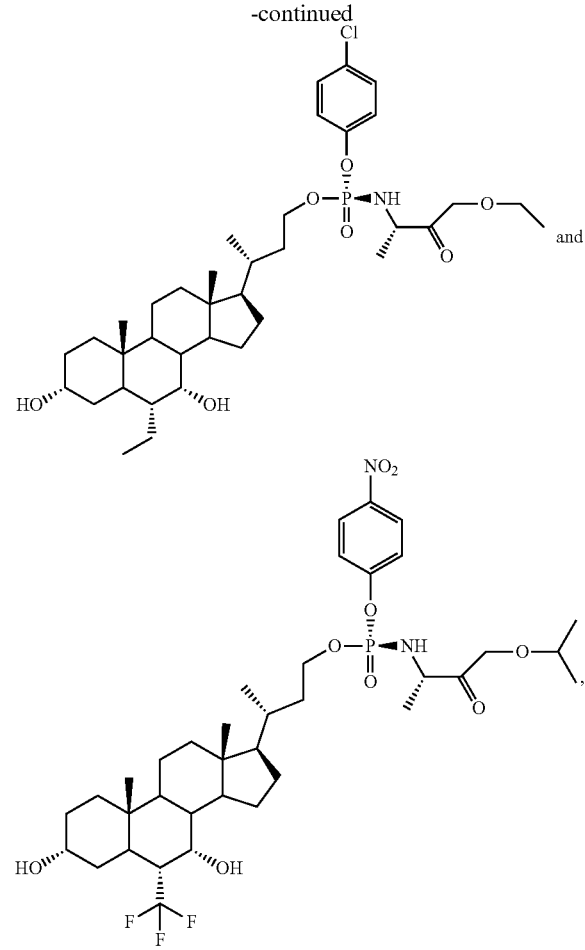
or a stereoisomer, a tautomer, or a pharmaceutically acceptable salt thereof.
16. The compound according to claim 1, wherein
each of the $R_2$ is independently cyano;
m is 0 or 1;
each of the $R_3$ is independently selected from the group consisting of fluorine, chlorine, bromine, substituted or unsubstituted methyl, and substituted or unsubstituted ethyl; and
n is 0 or 1.
* * * * *